United States Patent

Lohray et al.

[11] Patent Number: 6,114,526
[45] Date of Patent: Sep. 5, 2000

[54] HETEROCYCLIC COMPOUNDS, PROCESS FOR THEIR PREPARATION AND PHARMACEUTICAL COMPOSITIONS CONTAINING THEM AND THEIR USE IN THE TREATMENT OF DIABETES AND RELATED DISEASES

[75] Inventors: Vidya Bhushan Lohray; Braj Bhushan Lohray; Rao Bheema Paraselli; Ranga Madhavan Gurram; Rajagopalan Ramanujam; Ranjan Chakrabarti; Sarma K.S. Pakala, all of Hyderabad, India

[73] Assignees: Dr. Reddy's Research Foundation, Hyderabad, India; Reddy-Cheminor Inc., Ridgewood, N.J.

[21] Appl. No.: 09/353,286

[22] Filed: Jul. 14, 1999

Related U.S. Application Data

[63] Continuation of application No. 08/777,627, Dec. 31, 1996, Pat. No. 5,885,997, and a division of application No. 08/884,816, Jun. 30, 1997.

[30] Foreign Application Priority Data

Jul. 1, 1996 [IN] India .............................. 1150/MAS/96

[51] Int. Cl.[7] ...................... C07D 417/12; C07D 239/02; C07D 241/00
[52] U.S. Cl. ......................... 544/284; 544/316; 544/284; 544/311; 544/298; 544/253
[58] Field of Search ..................................... 544/316, 284

[56] References Cited

U.S. PATENT DOCUMENTS

| | | | |
|---|---|---|---|
| 4,342,771 | 8/1982 | Schnur | 424/263 |
| 4,367,234 | 1/1983 | Schnur | 424/272 |
| 4,725,610 | 2/1988 | Meguro | 514/369 |
| 4,873,255 | 10/1989 | Yoshioka | 514/369 |
| 5,002,953 | 3/1991 | Hindley | 513/275 |
| 5,036,079 | 7/1991 | Clark | 514/333 |
| 5,037,842 | 8/1991 | Goldstein | 514/375 |
| 5,130,379 | 7/1992 | Clark | 514/333 |
| 5,153,210 | 10/1992 | Ainsworth | 514/369 |
| 5,296,605 | 3/1994 | De Nanteuil | 540/369 |
| 5,330,999 | 7/1994 | De Nanteuil | 514/170 |
| 5,420,146 | 5/1995 | Malamas | 514/364 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,480,896 | 1/1996 | Malamas | 514/364 |
| 5,498,621 | 3/1996 | Dow | 514/369 |
| 5,521,201 | 5/1996 | Hindley | 514/369 |
| 5,521,202 | 5/1996 | Yano | 514/369 |
| 5,710,152 | 1/1998 | Nagao et al. | 514/225.2 |

FOREIGN PATENT DOCUMENTS 570067 of 0000 Australia .

| | | |
|---|---|---|
| 008203A | 2/1980 | European Pat. Off. . |
| 0139421 | 5/1985 | European Pat. Off. . |
| 155845A | 9/1985 | European Pat. Off. . |
| 0207581 | 1/1987 | European Pat. Off. . |
| 236624 | 9/1987 | European Pat. Off. . |

(List continued on next page.)

OTHER PUBLICATIONS

G. De Nanteuil, "Euglygaemic and Biological Activities of Novel Thiazolidine–2,4–dione Derivatives" Arzneittol Forschung/Drug Design, vol. 45, No. II, 1995, p. 1176–1181.

Whitcomb, R. W., "Thiazolidinediones", Expert Opinion on Investigational Drugs, vol. 4, No. 12, Dec. 1995, p. 1200–1309.

English Translation of JP–A–0912575.

Behavioral Brain Research, 75 (1996) p. 1–11, Messier, et al.

Chemical Pharmaceutical Bulletin, vol. 30 No. 10, 1982 p.3580–3600, Taskasi Sohda, et al.

D.A. Clark et al., "Substituted Dihydrobenzeopran . . . ", J. Med Chem. 1991, 34, 319–325.

R.L. Dow et al., "Benzyloxolidine–2, 4–diones . . . ", J. Med. Chem. 1991, 34, 1538–1544.

S.W. Goldstein et al. "Hydroxyorea Derivatives . . . ", J. Med. Chem. 1993, 36, 2238–2240.

B. Hullin et al., "Novel Thiazolidine . . . ", J. Med. Chem. 1992, vol. 35 No. 10, 1853–1861.

Journal of Medicinal Chemistry, vol. 37, No. 23, 1994, Barrie, CC. Et al., p. 3977–3985.

T. Sohda et al., "Studies on Antidiabetic . . . ", J. Med. Chem., 1992, vol. 35, No. 14, 2617–2626.

*Primary Examiner*—Jose' G. Dees
*Assistant Examiner*—Sabiha N. Qazi
*Attorney, Agent, or Firm*—Ladas & Parry

[57] ABSTRACT

The present invention relates to novel antidiabetic compounds, their tautomeric forms, their derivatives, their stereoisomers, their polymorphs, their pharmaceutically acceptable salts, their pharmaceutically acceptable solvates and pharmaceutically acceptable compositions containing them. This invention particularly relates to novel azolidinedione derivatives of the general formula (I), and their pharmaceutically acceptable salts, pharmaceutically acceptable solvates and pharmaceutical compositions containing them

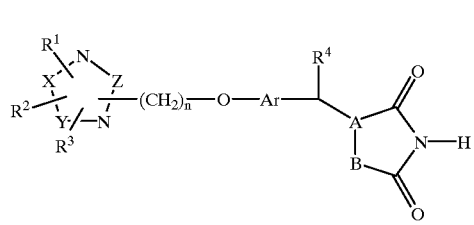

5 Claims, No Drawings

FOREIGN PATENT DOCUMENTS

| | | |
|---|---|---|
| 0306228 | 3/1989 | European Pat. Off. . |
| 0332331 | 9/1989 | European Pat. Off. . |
| 0332332 | 9/1989 | European Pat. Off. . |
| 0337819 | 10/1989 | European Pat. Off. . |
| 0356214 | 2/1990 | European Pat. Off. . |
| 0381371 | 8/1990 | European Pat. Off. . |
| 03974531 | 11/1990 | European Pat. Off. . |
| 0415605 | 3/1991 | European Pat. Off. . |
| 0419035 | 3/1991 | European Pat. Off. . |
| 0428312 | 5/1991 | European Pat. Off. . |
| 0439321 | 7/1991 | European Pat. Off. . |
| 0441605 | 8/1991 | European Pat. Off. . |
| 0454501 | 10/1991 | European Pat. Off. . |
| 0528734 | 2/1993 | European Pat. Off. . |
| 0543662 | 5/1993 | European Pat. Off. . |
| 0236624 | 10/1993 | European Pat. Off. . |
| 590793A | 4/1994 | European Pat. Off. . |
| 0604983 | 7/1994 | European Pat. Off. . |
| 605228A | 7/1994 | European Pat. Off. . |
| 0612743 | 8/1994 | European Pat. Off. . |
| 0643050 | 3/1995 | European Pat. Off. . |
| 645387A | 3/1995 | European Pat. Off. . |
| 0676308 | 10/1995 | European Pat. Off. . |
| 0678511 | 10/1995 | European Pat. Off. . |
| 0708098 | 4/1996 | European Pat. Off. . |
| 0733631 | 9/1996 | European Pat. Off. . |
| 745600A | 12/1996 | European Pat. Off. . |
| 0783888 | 7/1997 | European Pat. Off. . |
| 0787727 | 8/1997 | European Pat. Off. . |
| 62-175158 | 8/1987 | Japan . |
| 64-52765 | 2/1989 | Japan . |
| 7-138258 | 5/1995 | Japan . |
| 2558473 | 11/1996 | Japan . |
| 0912575 | 1/1997 | Japan . |
| 5355524 | 8/1984 | Spain . |
| 8528633 | of 0000 | United Kingdom . |
| 9112003 | 8/1991 | WIPO . |
| 9207838 | 5/1992 | WIPO . |
| 9207850 | 5/1992 | WIPO . |
| 9405659 | 3/1994 | WIPO . |
| 9425026 | 11/1994 | WIPO . |
| 9426720 | 11/1994 | WIPO . |
| 9507697 | 3/1995 | WIPO . |
| 9521608 | 8/1995 | WIPO . |
| 9526347 | 10/1995 | WIPO . |
| 9535108 | 12/1995 | WIPO . |
| 9605186 | 2/1996 | WIPO . |
| 9611196 | 4/1996 | WIPO . |
| 9626207 | 8/1996 | WIPO . |

HETEROCYCLIC COMPOUNDS, PROCESS FOR THEIR PREPARATION AND PHARMACEUTICAL COMPOSITIONS CONTAINING THEM AND THEIR USE IN THE TREATMENT OF DIABETES AND RELATED DISEASES

This application is a continuation of Ser. No. 08/777,627 filed Dec. 31, 1996 now U.S. Pat. No. 5,885,997, and a division of Ser. No. 08/884,816 filed Jun. 30, 1997.

FIELD OF THE INVENTION

The present invention relates to novel antidiabetic compounds, their tautomeric forms, their derivatives, their stereoisomers, their polymorphs, their pharmaceutically acceptable salts, their pharmaceutically acceptable solvates and pharmaceutically acceptable compositions containing them. This invention particularly relates to novel azolidinedione derivatives of the general formula (I), and their pharmaceutically acceptable salts, pharmaceutically acceptable solvates and pharmaceutical compositions containing them.

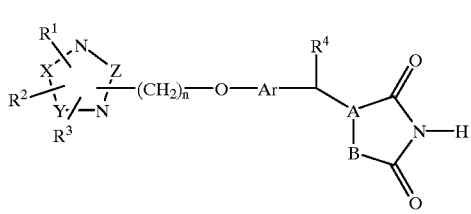

(I)

The present invention also relates to a process for the preparation of the above said novel, azolidinedione derivatives, their tautomeric forms, their stereoisomers, their polymorphs, their pharmaceutically acceptable salts, pharmaceutically acceptable solvates, novel intermediates and pharmaceutical compositions containing them.

The azolidinedione derivatives of the general formula (I) defined above of the present invention are useful for the treatment and/or prophylaxis of diseases Or conditions in which insulin resistance is the underlying pathophysiological mechanism. Examples of these diseases and conditions are type II diabetes, impaired glucose tolerance, dyslipidaemia, hypertension, coronary heart disease and other cardiovascular disorders including atherosclerosis. The azolidinedione derivatives of the formula (I) are useful for the treatment of insulin resistance associated with obesity and psoriasis. The azolidinedione derivatives of the formula (I) can also be used to treat diabetic complications and can be used for treatment and/or prophylaxis of other diseases and conditions such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

BACKGROUND OF THE INVENTION

Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817: N. Engl. J. Med.; (1987) 317: 350–357; J. Clin. Endocrinol. Metab., (1988) 66: 580–583; J. Clin. Invest., (1975) 68: 957–969) and other renal complications. (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X. In addition, polycystic ovarian syndrome (Patent Application No. WO 95/07697), psoriasis (Patent Application No. WO 95/35108). dementia (Behavioral Brain Research (1996) 75: 1–11) etc. may also have insulin resistance as a central pathogenic feature.

A number of molecular defects have been associated with insulin resistance. These include reduced expression of insulin receptors on the plasma membrane of insulin responsive cells and alterations in the signal transduction pathways that become activated after insulin binds to its receptor including glucose transport and glycogen synthesis.

Since defective insulin action is thought to be more important than failure of insulin secretion in the development of non-insulin dependent diabetes mellitus and other related complications, this raises doubts about the intrinsic suitability of antidiabetic treatment that is based entirely upon stimulation of insulin release. Recently, Takeda has developed a new class of compounds which are the derivatives of 5-(4-alkoxybenzyl)-2,4-thiazolidinediones of the formula (II) (Ref Chem. Pharm. Bull. 1982, 30, 3580–3600). In the formula (II), V represents substituted or unsubstituted divalent aromatic group and U represents various groups which have been reported in various patent documents.

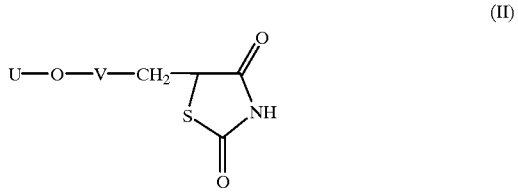

(II)

By way of examples, U may represent the following groups:

(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3. These compounds have been disclosed in the European Patent Application No. 0 177 353

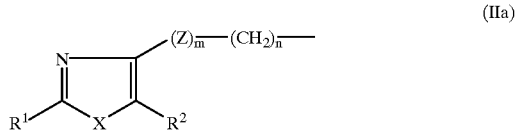

(IIa)

An example of these compounds is shown in formula (IIb)

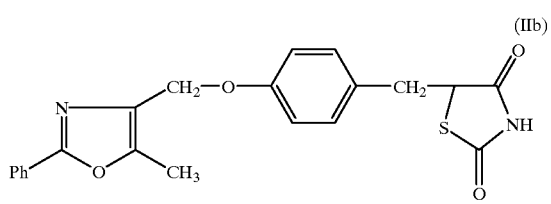

(ii) a group of the formula (IIc) wherein $R^1$ and $R^2$ are the same or different and each represents hydrogen or $C_1$–$C_5$ alkyl, $R^3$ represents hydrogen, acyl group, a ($C_1$–$C_6$) alkoxycarbonyl group or aralkyloxycarbonyl group, $R^4$–$R^5$ are same or different and each represent hydrogen. $C_1$–$C_5$ alkyl or $C_1$–$C_5$ alkoxy or $R^4$, $R^5$ together represent $C_1$–$C_4$ alkenedioxy group, n is 1, 2, or 3, W represents $CH_2$, CO, $CHOR^6$ group in which $R^6$ represents any one of the items or groups defined for $R^3$ and may be the same or different from $R^3$. These compounds are disclosed in the European Patent Application No. 0 139 421.

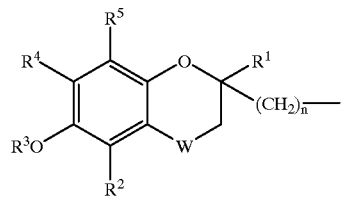

An example of these compounds is shown in (IId)

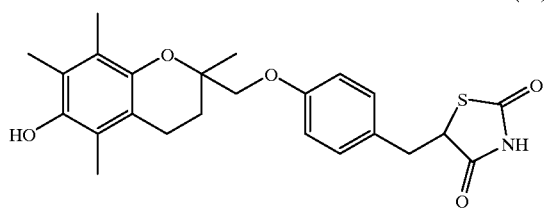

iii) A group of formula (IIe) where $A^1$ represents substituted or unsubstituted aromatic heterocyclic group. $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

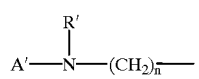

An example of this compound is shown in formula (IIf)

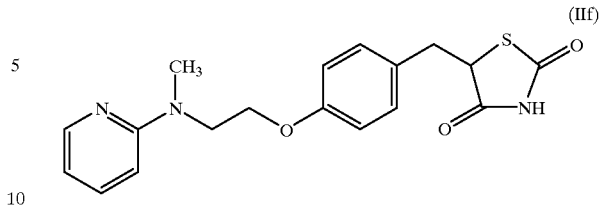

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application No. 0 604 983.

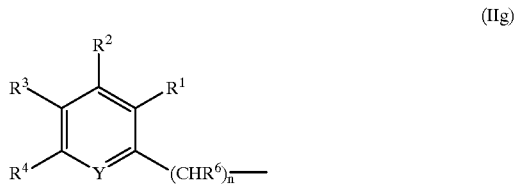

An example of this compound is shown in formula (IIh)

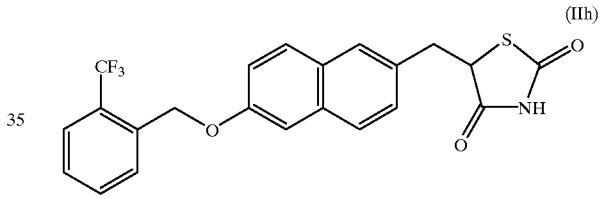

Still another class of antihyperglycemic agents are 5-substituted oxazolidine-2,4-diones and 2-substituted-1,2,4-oxadiazolidine-3,5-diones which can be represented in the formula (IIi),

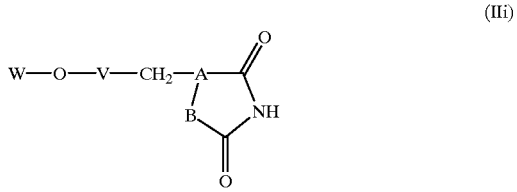

where V represents substituted or unsubstituted divalent aryl or hetero aryl group, W represents various groups which have been reported in various patent documents, A represents nitrogen atom or a CH group and B is an oxygen atom.

By way of examples, W may represent the following groups:

v) a group of formula (IIj), where R is ($C_1$–$C_6$) alkyl groups, cycloalkyl group, furyl, thienyl, substituted or unsubstituted phenyl group, X is hydrogen, methyl methoxy, chloro or fluoro. These compounds have been disclosed in the U.S. Pat. No. 5 037 842.

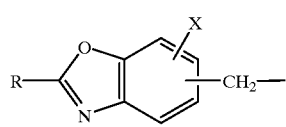
(IIj)

An example of these compounds is shown in formula (IIk).

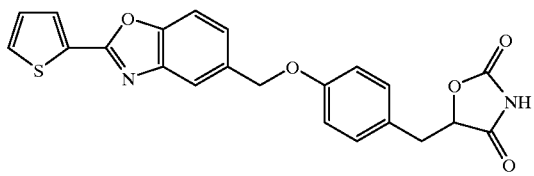
(IIk)

(vi) A group of formula (III) wherein $A^1$ represents a substituted or unsubstituted aromatic heterocyclyl group; $R^1$ represents a hydrogen atom, an alkyl group, an acyl group, an aralkyl group, wherein the aryl moiety may be substituted or unsubstituted or a substituted or unsubstituted aryl group, n represents an integer in the range of from 2 to 6. These compounds have been disclosed in the patent application No. WO 92/02520.

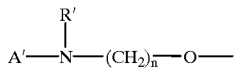
(III)

An example of these compounds is shown in formula (IIm).

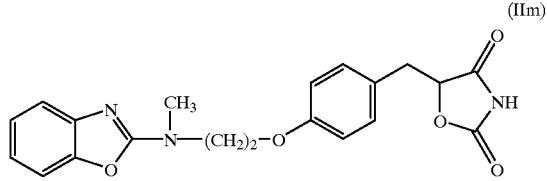
(IIm)

(vii) A group of formulae (IIn) and (IIo), where $R^1$ is hydrogen, $(C_1-C_8)$alkyl, $(C_1-C_8)$alkoxy, trifluoroalkoxy, halogen or trifluoromethyl group, $R^2$ is hydrogen or methyl and X is oxygen or sulfur. These compounds have been described in U.S. Pat. No. 5,480,486.

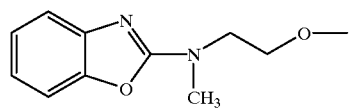
(IIn)

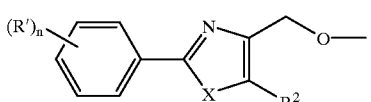
(IIo)

An example of these compounds is shown in formula (IIp)

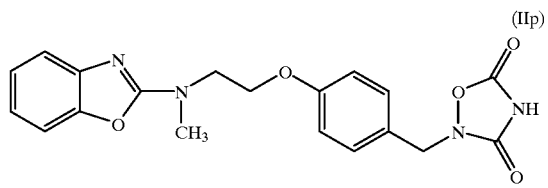
(IIp)

Some of the above referenced hitherto known antidiabetic compounds seem to possess bone marrow depression, liver and cardiac toxicities and modest potency and consequently their regular use for the treatment and control of diabetes is becoming limited and restricted.

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and to have better efficacy, which has resulted in the development of novel azolidinedione derivatives having the general formula (I) as defined above.

The main objective of the present invention is therefore, to provide novel azolidinedione derivatives, their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel azolidinedione derivatives, their tautomeric forms, their stereoisomers, their polymorphs, their pharmaceutically acceptable salts, their pharmaceutically acceptable solvates and pharmaceutical compositions containing them or their mixtures having enhanced activities, no toxic effect or reduced toxic effect.

Yet another objective of the present invention is to produce a process for the preparation of novel azolidinediones of the formula (I) as defined above, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their tautomers, their stereoisomers, their polymorphs, their salts, solvates or their mixtures in combination with suitable carriers, solvents diluents and other media normally employed in preparing such compositions.

Yet another objective of the present invention is to provide a process for the preparation of the novel intermediate of the formula (III)

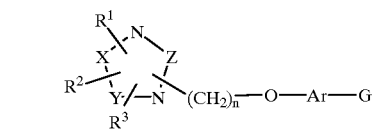
(III)

where G represents $-CHO$, $-NO_2$, $-NH_2$, $-CH=NHOH$, $-CH_2NHOH$, $-CH_2N(OH)CONH_2$ or $-CH_2CH(J)\text{-}COOR$, where J represents hydroxy group, halogen atom such as chlorine, bromine or iodine and R represents H or lower alkyl group such as methyl, ethyl, or propyl, X, Y, Z, $R^1$, $R^2$, $R^3$, n, and Ar are defined as in formula (I).

DETAILED DESCRIPTION OF THE INVENTION

Azolidinedione derivatives of the present invention have the general formula (I)

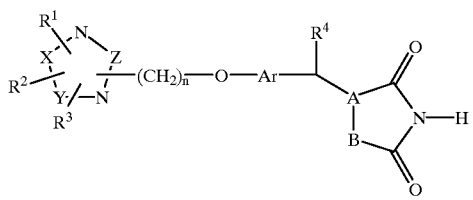

(I)

In the above formula (I), one of X, Y or Z represents C=O or C=S and the remaining of X, Y and Z represent a group C= or C=C, $R^1$, $R^2$ and $R^3$ are groups either on X, Y or Z or on a nitrogen atom $R^1$, $R^2$ and $R^3$ may be same or different and represent hydrogen, halogen, hydroxy, or nitro, or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives with the provision that when $R^1$, $R^2$ or $R^3$ is on a nitrogen atom it does not represent hydrogen, halogen, nitro, carboxylic acid or sulfonic acid groups, or any two of $R^1$, $R^2$ and $R^3$ along with the adjacent atoms to which they are attached may also form a substituted or unsubstituted cyclic structure of from 4 to 7 atoms with one or more double bonds, the cyclic structure may be carbocyclic or may contain one or more heteroatoms selected from oxygen nitrogen and sulfur. When the groups representing $R^1$, $R^2$ or $R^3$ are substituted, the substituents are selected from the same groups that may represent $R^1$, $R^2$, and $R^3$ such as hydroxy, halogen, or nitro, or optionally substituted groups selected from alkyl, cycloalkyl alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives. The linking group represented by —$(CH_2)_n$—O— in formula (I) may be attached either through nitrogen atom or through X, Y or Z where n is an integer ranging from 1–4. Ar represents an optionally substituted divalent aromatic or heterocyclic group, $R^4$ represents hydrogen atom, halogen or lower alkyl group or forms a bond together with the adjacent group A. A represents a nitrogen atom or a group $CR^5$ where $R^5$ represents hydrogen, halogen or lower alkyl group such as methyl ethyl, propyl or the like or $R^5$ forms a bond together with $R^4$; B represents an oxygen atom or a sulfur atom when A is $CR^5$ and B represents an oxygen atom when A is a nitrogen atom.

Suitable combinations of X, Y and Z that form the ring structure containing X, Y and Z in the formula (I) are represented in the following Table:

| S. No. | X | Y | Z |
|---|---|---|---|
| 1. | C=O or C=S | =C | C=C |
| 2. | C=O or C=S | C=C | =C |
| 3. | =C | C=O or C=S | C=C |
| 4. | =C | C=C | C=O or C=S |
| 5. | C=C | C=O or C=S | =C |
| 6. | C=C | =C | C=O or C=S |

It is preferred that at least one of X, Y or Z be C=C.

It is preferred that one of X or Y be C=O. Suitable ring structures containing X, Y and Z include

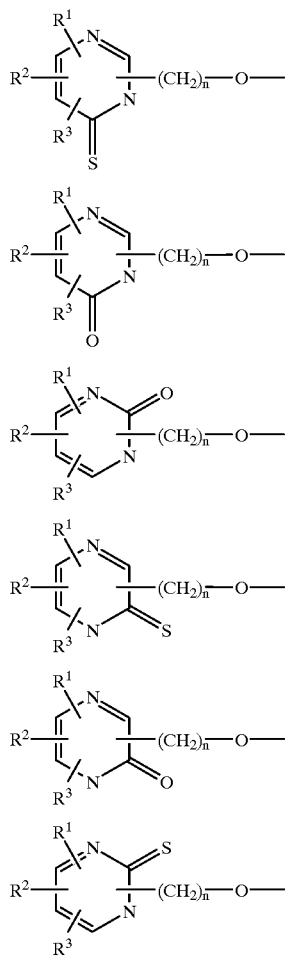

A preferred ring structure is

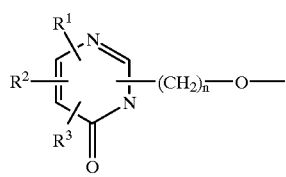

When $R^1$, $R^2$ and $R^3$ groups are attached to X, Y, and Z it is preferred that $R^1$, $R^2$ and $R^3$ are selected from hydrogen, halogen atom such as fluorine, chlorine, bromine, or iodine; hydroxy, nitro; substituted or unsubstituted $(C_1-C_{12})$alkyl group, especially, linear or branched $(C_1-C_6)$alkyl group, such as methyl, ethyl, n-propyl, isopropyl, n-butyl, isobutyl, t-butyl and the like; cycloalkyl group such as cyclopropyl, cyclobutyl, cyclopentyl, cyclohexyl and the like; cycloalkyloxy group such as cyclopropyloxy, cyclobutyloxy, cyclopentyloxy, cyclohexyloxy and the like; aryl group such as phenyl or naphthyl, the aryl group may be substituted; aralkyl such as benzyl or phenethyl, the aralkyl group may be substituted; heteroaryl group such as pyridyl, thienyl, furyl, pyrrolyl, oxazolyl, thiazolyl, oxadiazolyl, tetrazolyl, benzopyranyl, benzofuranyl and the like, the heteroaryl group may be substituted; heterocyclyl groups such as aziridinyl, pyrrolidinyl, morpholinyl, piperidinyl and the like, the heterocyclyl group may be substituted; aryloxy such as phenoxy, naphthyloxy, the aryloxy group may be substituted; alkoxycarbonyl such as methoxycarbonyl or ethoxycarbonyl; aryloxycarbonyl group such as optionally substituted phenoxycarbonyl; arylamino group such as $HNC_6H_5$; amino group; amino$(C_1-C_6)$alkyl; hydroxy$(C_1-C_6)$alkyl; $(C_1-C_6)$alkoxy; thio$(C_1-C_6)$alkyl; $(C_1-C_6)$alkylthio; acyl group such as acetyl, propionyl or benzoyl, the acyl group may be substituted; acylamino groups such as $NHCOCH_3$, $NHCOC_2H_5$, $NHCOC_3H_7$, $NHCOC_6H_5$, aralkoxycarbonylamino group such as $NHCOOCH_2C_6H_5$, alkoxycarbonylamino group such as $NHCOOC_2H_5$, $NHCOOCH_3$ and the like; carboxylic acid or its derivatives such as amides, like $CONH_2$, $CONHMe$, $CONMe_2$, $CONHEt$, $CONEt_2$, $CONHPh$ and the like, the carboxylic acid derivatives may be substituted; acyloxy group such as $OCOMe$, $OCOEt$, $OCOPh$ and the like which may optionally be substituted; sulfonic acid or its derivatives such as $SO_2NH_2$, $SO_2NHMe$, $SO_2NMe_2$, $SO_2NHCF_3$ and the like; the sulfonic acid derivatives may be substituted.

All of the preferred groups that may represent $R^1$, $R^2$ and $R^3$ may be substituted or unsubstituted.

When $R^1$, $R^2$ or $R^3$ are attached to nitrogen atom, it is preferred that $R^1$, $R^2$ and $R^3$ are selected from $(C_1-C_{12})$alkyl group, especially linear or branched $(C_1-C_6)$alkyl group, such as methyl, ethyl, n-propyl, isopropyl, n-butyl, isobutyl, t-butyl groups and the like; cycloalkyl group such as cyclopropyl, cyclobutyl, cyclopentyl, cyclohexyl and the like; aryl group such as phenyl or naphthyl; aralkyl such as benzyl or phenethyl; heteroaryl group such as pyridyl, thienyl, furyl, pyrrolyl, oxazolyl, thiazolyl, oxadiazolyl, tetrazolyl and the like; heterocyclyl groups such as aziridinyl, pyrrolidinyl, morpholinyl, piperidinyl and the like; alkoxycarbonyl such as methoxycarbonyl or ethoxycarbonyl; aryloxycarbonyl group such as phenoxycarbonyl; amino$(C_1-C_6)$alkyl; hydroxy$(C_1-C_6)$alkyl; thio$(C_1-C_6)$alkyl; or acyl group such as acetyl, propionyl, benzoyl, and the like.

All of the preferred groups that may represent $R^1$, $R^2$ and $R^3$ may be substituted or unsubstituted.

When the groups represented by $R^1$, $R^2$ and $R^3$ are substituted, the substituents selected are from the same groups as those groups that represent $R^1$, $R^2$ and $R^3$ and may be selected from halogen, hydroxy, or nitro, or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives.

Suitable ring structure formed by any two of $R^1$, $R^2$ and $R^3$ along with the adjacent atoms to which they are attached, include substituted or unsubstituted 4–7 membered cyclic structure which may contain one or more double bonds, the cyclic structure may be carbocyclic or optionally contains one or more hetero atoms selected from nitrogen, oxygen and sulfur. Examples of the cyclic structures are phenyl, naphthyl, thienyl, furyl, pyrrolyl, oxazolyl, oxadiazolyl, thiazolyl, imidazolyl, azacyclobutenyl, isoxazolyl, azepinyl, pyridyl, pyridazyl, pyrimidinyl, dihydrofuryl, dihydrothienyl, tetrahydropyridyl, tetrahydrophenyl, tetrahydronaphthyl and the like. The substituents on the cyclic structure may be selected from the same groups as that of $R^1$, $R^2$ and $R^3$. Examples of possible substituents are halogen, alkyl, cycloalkyl, alkoxy, cycloalkoxy, aryl, aralkyl, heterocyclyl, heteroaryl, heteroaralkyl, hydroxy, acyl, acyloxy, hydroxyalkyl, amino, acylamino, arylamino, aminoalkyl, aryloxy, alkoxycarbonyl, alkylamino, alkoxyalkyl, carboxylic acid or its derivatives, or sulfonic acid or its derivatives.

It is more preferred that $R^1$, $R^2$ and $R^3$ groups represent hydrogen; halogen atom such as fluorine, chlorine, bromine, or iodine; alkyl group such as methyl, ethyl, n-propyl or n-butyl; cycloalkyl group such as cyclopropyl; aryl group such as phenyl; or aralkyl group such as benzyl.

When the groups represented by $R^1$, $R^2$ and $R^3$ are substituted it is preferred that the substituents are selected from halogen, haloalkyl, haloalkoxy, and halocycloalkoxy wherein the halogen atom is preferably a fluorine atom.

The ring structure formed by any two of $R^1$, $R^2$ and $R^3$ along with the adjacent atoms to which they are attached, may be substituted or unsubstituted. Preferred ring structures are phenyl, thienyl, furyl or pyridyl groups. When these ring structures are substituted it is preferred that the substituents are selected from halogen, lower alkyl group such as methyl or ethyl; trifluoromethyl; fluoromethyl; difluoromethyl; and alkoxy groups such as methoxy, trifluoromethoxy, fluoromethoxy and difluoromethoxy.

The linking group $—(CH_2)_n—O—$ may be linked either through a nitrogen atom or through X, Y or Z. The integer n may range from 1 to 4, preferably n is 1 to 2. It is preferred that the king group be linked either through nitrogen or through Z when Z represents $=C$.

It is preferred that the group represented by Ar be substituted or unsubstituted divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl, benzoxazolyl and the like. The substituents on the group represented by Ar may be selected from linear or branched $(C_1-C_6)$alkyl, $(C_1-C_3)$alkoxy, halogen, acyl, amino, acylamino, thio, or carboxylic or sulfonic acids or their derivatives.

It is more preferred that Ar represents substituted or unsubstituted divalent phenylene, naphthylene, benzofuryl, indolinyl, quinolinyl, azaindolyl, azaindolinyl, benzothiazolyl or benzoxazolyl.

It is still more preferred that Ar is represented by divalent phenylene or naphthylene, which may be optionally substituted by methyl, halomethyl, methoxy or halomethoxy groups.

Suitable $R^4$ includes hydrogen; lower alkyl group such as methyl ethyl or propyl; halogen atom such as fluorine, chlorine, bromine or iodine, or $R^4$ together with A represents a bond.

Suitable A group may be nitrogen or $CR^5$ where $R^5$ may be a hydrogen atom, halogen, lower alkyl group or together with $R^4$ forms a bond.

Suitable B group includes a hetero atom selected from O or S, with the provision that when A is $CR^5$, B is selected from sulfur or oxygen, and when A is nitrogen, B represents oxygen Suitable ring structure comprising A and B include 2,4-dioxooxazolidin-5-yl, 2,4-dioxooxazolidin-5-yl, 3,5-dioxol, 2,4-oxadiazolidin-2-yl groups. Preferred ring structures comprising, A and B include 2,4-dioxooxazolidine-5-yl and 2,4-dioxothiazolidin-5-yl groups.

It is more preferred that the ring structure comprising A and B is a 2,4-dioxothiazolidin-5-yl group.

Pharmaceutically acceptable salts forming part of this invention include salts of the azolidinedione moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts; alkaline earth metal salts, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention includes:

5-[4-[2-[2,4-dimethyl-6-oxo-1,6-dihydro-1-pyrimidinyl] ethoxy]phenyl methyl]thiazolidine-2,4-dione and its salts, 5-[4-[2-[2-ethyl-4-methyl-6-oxo-1,6-dihydro-1-pyrimidinyl]ethoxy]phenyl methyl]thiazolidine-2,4-dione and its salts, 5-[4-[2-[4-methyl-2-propyl-6-oxo-1,6-dihydro-1-pyrimidinyl]ethoxy]phenyl methyl]thiazolidine-2,4-dione and its salts, 5-[4-[2-[2-butyl-4-methyl-6-oxo-1,6-dihydro-1-pyrimidinyl]ethoxy]phenyl methyl]thiazolidine-2,4 dione and its salts, 5-[4-[2-[2-ethyl-4-phenyl-6-oxo-1,6-dihydro-1-pyrimidinyl]ethoxy]phenyl methyl]thiazolidine-2,4-dione and its salts, 5-[4-[[3-methyl-4-oxo-3,4-dihydro-2-quinazolinyl] methoxy]phenyl methyl]thiazolidine-2,4-dione and its salts and its polymorphs, 5-[4-[[3-ethyl-4-oxo-3,4-dihydro-2-quinazolinyl]methoxy] phenyl methyl]thiazolidine-2,4-dione and its salts, 5-[4-[2-[2-methyl-4-oxo-3,4-dihydro-3-quinazolinyl] ethoxy]phenyl methyl]thiazolidine-2,4-dione and its salts, 5-[4-[2-[2-ethyl-4-oxo-3,4-dihydro-3-quinazolinyl]ethoxy] phenyl methyl]thiazolidine-2,4-dione and its salts, 5-[4-[2-[6,7-dimethoxy-2-ethyl-4-oxo-3,4-dihydro-3-quinazolinyl]ethoxy]phenyl methyl]thiazolidine-2,4-dione and its salts, 5-[4-[2-[2-ethyl-4-methyl-6-oxo-1,6-dihydro-1-pyrimidinyl]ethoxy]phenyl methyl]oxazolidine-2,4-dione and its salts, 5-[4-[2-[4-methyl-2-propyl-6-oxo-1,6-dihydro-1-pyrimidinyl]ethoxy]phenyl methyl]oxazolidine-2,4-dione and its salts, 5-[4-[[3-methyl-4-oxo-3,4-dihydro-2-quinazolinyl] methoxy]phenyl methyl]oxazolidine-2,4-dione and its salts, 2-[4-[2-[2-ethyl-4-methyl-6-oxo-1,6-dihydro-1-pyrimidinyl]ethoxy]phenyl methyl]-1,2,4 oxadiazolidine-3,5-dione and its salts, 2-[4-[2-[4-methyl-2-propyl-6-oxo-1,6-dihydro-1-pyrimidinyl]ethoxy]phenyl methyl]-1,2,4-oxadiazolidine-3,5-dione and its salts, 2-[4-[[3-methyl-4-oxo-3,4-dihydro-2-quinazolinyl] methoxy]phenyl methyl]-1,2,4-oxadiazolidine-3,5-dione and its salts, 5-[4-[2-[2,4-dimethyl-6-oxo-1,6-dihydro-1-pyrimidinyl] ethoxy]phenyl methylene]thiazolidine-2,4-dione and its salts, 5-[4-[2-[2-ethyl-4-methyl-6-oxo-1,6-dihydro-1-pyrimidinyl]ethoxy]phenyl methylene]thiazolidine-2,4-dione and its salts, 5-[4-[2-[4-methyl-2-propyl-6-oxo-1,6-dihydro-1-pyrimidinyl]ethoxy]phenyl methylene]thiazolidine-2,4-dione and its salts, 5-[4-[2-[2-ethyl-4-phenyl-6-oxo-1,6-dihydro-1-pyrimidinyl]ethoxy]phenyl methylene]thiazolidine-2,4-dione and its salts, 5-[4-[[3-methyl-4-oxo-3,4-dihydro-2-quinazolinyl] methoxy]phenyl methylene]thiazolidine-2,4-dione and its salts, 5-[4-[[3-ethyl-4-oxo-3,4-dihydro-2-quinazolinyl]methoxy] phenyl methylene]thiazolidine-2,4-dione and its salts, 5-[4-[2-[2-methyl-4-oxo-3,4-dihydro-3-quinazolinyl] ethoxy]phenyl methylene]thiazolidine-2,4-dione and its salts, 5-[4-[2-[2-ethyl-4-oxo-3,4-dihydro-3-quinazolinyl]ethoxy] phenyl methylene]thiazolidine-2,4-dione and its salts, 5-[4-[[3-methyl-4-oxo-3,4-dihydro-2-quinazolinyl] methoxy]-3-methoxyphenyl methylene]thiazolidine-2,4-dione and its salts, More preferred compounds according to the present invention include 5-[4-[2-[2-ethyl-4-methyl-6-oxo-1,6-dihydro-1-pyrimidinyl]ethoxy]phenyl methyl]thiazolidine-2,4-dione, 5-[4-[2-[4-methyl-2-propyl-6-oxo-1,6-dihydro-1-pyrimidinyl]ethoxy]phenyl methyl]thiazolidine 2,4-dione, 5-[4-[2-[2-methyl-4-oxo-3,4-dihydro-3-quinazolinyl] ethoxy]phenyl methyl]thiazolidine-2,4-dione, sodium salt, 5-[4-[2-[2-ethyl-4-oxo-3,4-dihydro-3-quinazolinyl]ethoxy] phenyl methyl]thiazolidine-2,4-dione, sodium salt.

5-[4-[[3-methyl-4-oxo-3,4-dihydro-2-quinazolinyl] methoxy]phenyl methyl]thiazolidine-2,4-dione and its polymorphs, 5-[4-[[3-methyl-4-oxo-3,4-dihydro-2-quinazolinyl] methoxy]phenyl methyl]thiazolidine-2,4-dione sodium salt and its polymorphs, 5-[4-[[3-methyl-4-oxo-3,4-dihydro-2-quinazolinyl] methoxy]phenyl methyl]thiazolidine-2,4-dione, potassium salt, 5-[4-[[3-methyl-4-oxo-3,4-dihydro-2-quinazolinyl] methoxy]phenyl methylene]thiazolidine-2,4-dione, sodium salt.

According to a feature of the present invention, there is provided a process for the preparation of novel intermediate of the general formula (III)

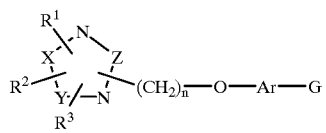
(III)

where X, Y, Z, R$^1$, R$^2$, R$^3$ and n are as defined earlier, -(CH$_2$)$_n$—O— linker is attached to nitrogen atom, G represents —CHO or —NO$_2$ group which comprises, reacting a compound of the general formula (IV)

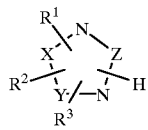
(IV)

where X, Y, Z, R$^1$, R$^2$ and R$^3$ are as defined earlier and H atom is attached to one of the nitrogen atoms of the ring, with a compound of general formula (V)

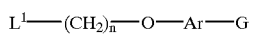
(V)

where Ar and n are as defined earlier and L$^1$ may be a halogen atom such as Cl, Br, I or a leaving group such as methanesulfonate, trifluoromethanesulfonate, p-toluenesulfonate etc, and G represents CHO, or NO$_2$ group.

The reaction of a compound of general formula (IV) with a compound of general formula (V) to produce a compound of general formula (III) may be carried Out in the presence of solvents such as DMSO, DMF, DME, THF, dioxane, ether and the like or a combination thereof The reaction may be carried out in an inert atmosphere which may be maintained by using inert gases such as N$_2$, Ar, He. The reaction may be effected in the presence of a base such as alkalis like sodium hydroxide, potassium hydroxide, alkali metal carbonates like sodium carbonate potassium carbonate; alkali metal hydrides such as sodium hydride or potassium hydride; organometallic bases like n-butyl lithium, alkali metal amides like sodamide or mixtures thereof The amount of base may range from 1 to 5 equivalents, based on the amount of the compound of formula (IV). preferably the amount of base ranges from 1 to 3 equivalents. 1 to 3 equivalents of alkali metal halides based on the amount of compound of formula (IV) such as lithium bromide may be added as an additive. The reaction may be carried out at a temperature in the range of 0° C. to 150° C., preferably at a temperature in the range of 15° C. to 100° C. The duration of the reaction may range from 0.25 to 24 hours, preferably from 0.25 to 6 hours.

In another embodiment of the invention, the novel intermediate of the general formula (III) defined and obtained above where G is CHO or NO$_2$ group, can be prepared by reacting the compound of the general formula (VI).

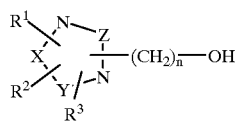
(VI)

wherein, X, Y, Z, R$^1$, R$^2$, R$^3$ and n are as defined earlier, with a compound of general formula (VII)

(VII)

where L$^2$ is a halogen atom. G is a CHO or a NO$_2$ group and Ar is as defined earlier.

The reaction of compound of formula (VI) with the compound of formula (VII) to produce a compound of formula (III) may be carried out in the presence of solvents such as THF, DMF, DMSO, DME and the like. The inert atmosphere may be maintained by using inert gases such as N$_2$, Ar or He. The reaction may be effected in the presence of a base such as K$_2$CO$_3$, Na$_2$CO$_3$, NaH. The reaction temperature may range from 20° C. to 150° C., preferably at a temperature in the range of 30° C. to 100° C. The duration of the reaction may range from 1 to 24 hours, preferably from 2 to 6 hours.

In another embodiment of the present invention, the novel intermediate of general formula (III), where G is a CHO or NO$_2$ group, can also be prepared by the reaction of compound of general formula (VIII)

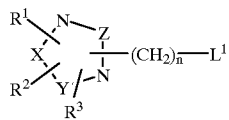
(VIII)

where X, Y, Z, R$^1$, R$^2$, R$^3$, n and L$^1$ are as defined earlier with a compound of general formula (IX)

(IX)

where G is a CHO or NO$_2$ group and Ar is as defined earlier.

The reaction of compound of formula (VIII) with compound of formula (IX) to produce a compound of the formula (III) may be carried out in the presence of solvents such as THF. DMF DMSO, DME and the like or mixtures thereof The reaction may be carried out in an inert atmosphere which may be maintained by using inert gases such as N$_2$, Ar, or He. The reaction may be effected in the presence of a base such as K$_2$CO$_3$, Na$_2$CO$_3$ or NaH or mixtures thereof The reaction temperature may range from 20° C.–120° C., preferably at a temperature in the range of 30° C.–100° C. The duration of the reaction may range from 1 to 12 hours, preferably from 2 to 6 hours.

The present invention provides a process for the preparation of novel azolidinedione derivatives of general formula (I), their tautomeric forms, their stereoisomers, their polymorphs, their pharmaceutically acceptable salts and their pharmaceutically acceptable solvates wherein R$^1$, R$^2$, R$^3$, X, Y, Z, n and Ar are as defined earlier and A represents CR$^5$ where R$^5$ together with R$^4$ represent a bond and B represents a sulfur or a oxygen atom, and further to a compound of formula (I) wherein $R^4$ and $R^5$ represent hydrogen and all symbols are as defined above, which comprises:

reacting the novel intermediate of the general formula (III) obtained above where G represents CHO group with 2,4-thiazolidinedione or 2,4-oxazolidinedione and removing the water formed during the reaction by conventional methods to yield a compound of general formula (X)

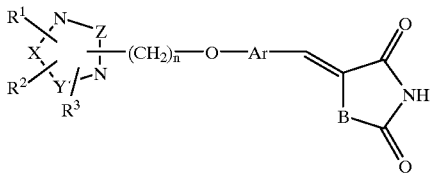

(X)

where $R^1$, $R^2$, $R^3$, X, Y, Z, n and Ar are as defined earlier and B represents sulfur or oxygen.

The reaction between the compound of the general formula (III) where G is a CHO group with 2,4-thiazolidinedione or 2,4-oxazolidinedione, to yield compound of general formula (X) wherein B represents a sulfur or an oxygen atom respectively, may be carried out neat in the presence of sodium acetate or in the presence of a solvent such as benzene, toluene, methoxyethanol or mixtures thereof The reaction temperature may range from 80° C. to 140° C. depending upon the solvents employed and in the range from 80° C. to 180° C. when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular seives. Oxazolidine-2-oxo-4-thione may be used instead of 2,4-oxazolidinedione. However, the thio group needs to be converted to oxo group by oxidation using agents such as hydrogen peroxide or peroxyacids like mCPBA.

The compound of the general formula (X) obtained in the manner described above is reduced by known method to obtain the compound of general formula (XI)

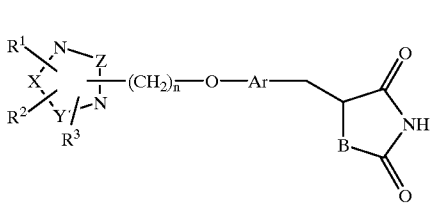

(XI)

wherein $R^1$, $R^2$, $R^3$, X, Y, Z, n and Ar are as defined earlier and B represents a sulfur atom or an oxygen atom. The compound of general formula (XI) represents the compound of general formula (I). wherein $R^4$ is hydrogen, A is $CR^5$ where $R^5$ is hydrogen and other symbols are as defined earlier.

The reduction of compound of the formula (X) to yield a compound of the general formula (XI) may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate and the like. A pressure between atmospheric pressure and 80 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol.

The compound of the general formula (XI) obtained above is converted into its pharmaceutically acceptable salts, or its pharmaceutically acceptable solvates by conventional methods.

In another embodiment of the present invention, the compound of the general formula (I) can also be prepared by reacting a compound of the general formula (VIII) defined above with a compound of general formula (XII)

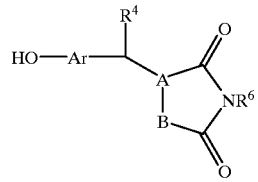

(XII)

where $R^4$, A, B and Ar are as defined earlier and $R^6$ is hydrogen or a nitrogen protecting group which is removed after the reaction.

The reaction of compound of formula (VIII) with compound of formula (XII) to produce a compound of the formula (I) may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof. The reaction temperature may range from 20° C.–120° C., preferably at a temperature in the range of 30° C.–80° C. The duration of the reaction may range from 1 to 12 hours, preferably from 2 to 6 hours.

In still another embodiment of the invention, the compound of the general formula (I), where —$(CH_2)_n$—O— linker is attached to nitrogen atom can be prepared by reacting the compound of the general formula (IV) defined above with a compound of general formula (XIII)

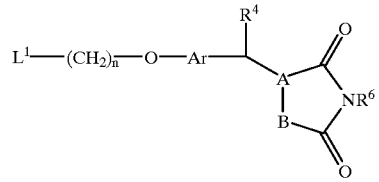

(XIII)

where $L^1$, n, Ar, A, B, $R^4$ and $R^6$ are as defined earlier and removal of the protecting group when $R^6$ is a nitrogen protecting group.

The reaction of compound of general formula (IV) with a compound of general formula (XIII) to produce a compound of general formula (I) may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as alkalis like sodium hydroxide, or potassium hydroxide; alkali metal carbonates like sodium carbonate, or potassium carbonate: alkali metal hydrides such as sodium hydride: organometallic bases like n-butyl lithium: alkali metal amides like sodamide, or mixtures thereof Multiple solvents and bases can be used. The amount of base may range from 1 to 5 equivalents, preferably 1 to 3 equivalents. 1 to 3 equivalents of alkali metal halides such as lithium bromide may be added as an additive. The reaction temperature may be in the range of 0° C. to 120° C., preferably at a temperature in the range of 20° C. to 100° C. The duration of the reaction may range from 0.5 to 24 hours, preferably from 0.5 to 6 hours.

In yet another embodiment of the present invention, the compound of general formula (I), where $R^1$, $R^2$, $R^3$, X, Y, Z, n and Ar are as defined earlier, $R^4$ represents hydrogen and A is CH and B represents S or O can be prepared by the reaction of compound of general formula (XIV)

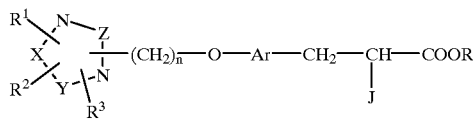

(XIV)

where $R^1$, $R^2$, $R^3$, X, Y, Z, n and Ar are as defined earlier, J is a halogen atom like chlorine, bromine or iodine or a hydroxy group and R is a lower alkyl group, with urea when J is a OH group and with thiourea when J is a halogen atom, followed by treatment with an acid.

The reaction of compound of general formula (XIV) with urea or thiourea is normally carried out in the presence of alcoholic solvent such as methanol, ethanol, propanol, isobutanol, 2-methoxybutanol, etc or DMSO or sulfolane. The reaction may be conducted at a temperature in the range between 20° C. and the reflux temperature of the solvent used. Bases such as NaOAc, KOAc, NaOMe, NaOEt etc. can be used. The reaction is normally followed by treatment with a mineral acid such as hydrochloric acid at 20° C. to 100° C.

The compound of general formula (XIV) where J is hydroxy group is prepared by the hydrolysis of compound of general formula (XIV) where J is a halogen atom using aqueous alkali at a temperature ranging from 20° C. to 100° C. followed by reesterification of the hydrolysed acid group by conventional methods.

The compound of general formula (XIV) where J is a OH group may also be prepared from compound of formula (XIV) where J is a halogen atom by reacting with formamide in the presence of water. The amount of formamide used in the reaction ranges from 0.5 to 1.5 mL and water used ranges from 20 μL to 0.1 mL for one mmol of the halo compound (XIV). The reaction is conducted at a temperature ranging from 80° C. to 180° C., preferably from 120° C. to 150° C., over a period ranging from 1 to 8 hours.

The compound of general formula (XIV) where J is a halogen atom can be prepared by the diazotization of the amino compound of the general formula (XV)

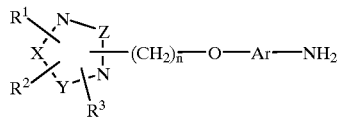

(XV)

where all symbols are as defined earlier, using alkali metal nitrites followed by treatment with acrylic acid esters in the presence of hydrohalo acids and catalytic amount of copper oxide or copper halide.

The compound of general formula (XV) can in turn be prepared by the conventional reduction of the novel intermediate (III) where G is $NO_2$ group and other symbols are as defined earlier.

In another embodiment of the present invention, the compound of general formula (I), where $R^1$, $R^2$, $R^3$, X, Y, Z, n and Ar are as defined earlier and A is nitrogen atom and B is oxygen atom can be prepared by a process which comprises: reaction of novel intermediate of formula (III) where all symbols are as defined above, and G represents a CHO group with $NH_2OH$. HCl to yield a compound of general formula (III) where G represents CH=NOH group and all symbols are as defined earlier, followed by metal borohydride reduction to yield a compound of general formula (XVI)

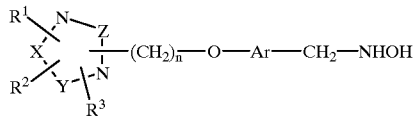

(XVI)

where all symbols are as defined earlier.

The reaction of compound of general formula (III), where G is CHO group and other symbols are as defined earlier, with hydroxylamine hydrochloride is carried out in solvents such as ethanol, methanol, THF, dioxane and the like following the conventional method to make oximes. 1 to 10 equivalents of $NH_2OH.HCl$ may be used, preferably, 2 to 5 equivalents. Bases such as alkali metal acetates or ammonium acetate may be used. Reaction may be carried out in the presence of water. Temperature in the range of 0° C. to reflux temperature of the solvent may be used. The oxime obtained in the manner described above is reduced using reducing agents such as alkali metal borohydrides like sodium borohydride or sodium cyanoborohydride or borane reagents using conventional conditions to yield the compound of general formula (XVI).

The compound of general formula (XVI) in turn is reacted with halocarbonyl isocyanate or alkoxycarbonyl isocyanate to yield a compound of general formula (I) or with KOCN to yield a compound of general formula (III) where G is $CH_2N(OH)CONH_2$, followed by treatment with carbonylating agents such as alkyl haloformate to produce the compound of general formula (I) where $R^1$, $R^2$, $R^3$, X, Y, Z, n, Ar are as defined earlier, A represents nitrogen atom and B is oxygen atom.

The reaction of compound of general formula (XVI) with halocarbonyl isocyanate such as chlorocarbonyl isocyanate or alkoxycarbonyl isocyanate such as ethoxycarbonyl isocyanate may be carried out in inert solvents such as THF, dioxane, etc at a temperature in the range −15° C. to 50° C. The reaction may be carried out for 0.5 to 12 hours depending on the substrates used for the reaction.

Alternatively, the compound of general formula (XVI) may be treated with excess of KOCN hi organic acids such as acetic acid. Water may be used in the reaction. The reaction may be carried out at a temperature in the range of 20° C. to 120° C. The product isolated in the reaction is further treated with alkyl haloformate such as ethyl chloroformate in the presence of 1 to 10 equivalents of alkali such as sodium hydroxide, potassium hydroxide and the like to obtain compound of general formula (I) where all the symbols are as defined earlier and A represents nitogen atom and B represents oxygen atom.

In yet another embodiment of the invention, the compound of general formula (I), where the linker —$(CH_2)_n$—O— is attached through Z, where Z represents =C, and all other symbols are as defined earlier can be prepared by reacting the compound of general formula (XVII)

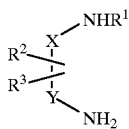

(XVII)

where $R^1$, $R^2$, and $R^3$ are as defined earlier, X represents C=O or C=S and Y represents C=C; or when $R^2$ and $R^3$ together with Y form a cyclic structure as defined earlier. X represents C=O or C=S, Y represents C=C and $R^1$ is as defined earlier, with a compound of general formula (XVIII)

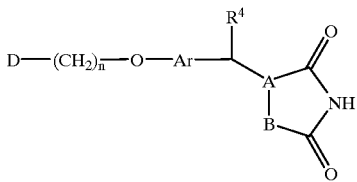

(XVIII)

where Ar, $R^4$, A, B and n are as defined earlier, D may be —CN; —$C(OR^7)_3$ where $R^7$ is $(C_1$–$C_4)$alkyl; —C(=O)—$R^8$ where $R^8$ may be selected from —OH, Cl, Br, I, —$NH_2$, —NHR, OR where R is a lower alkyl group such as methyl, ethyl, propyl and the like, or $R^8$ may be O—(C=O)—$R^9$, where $R^9$ may be a linear or branched $(C_1$–$C_5)$alkyl group such as methyl, ethyl, propyl, isopropyl, butyl, t-butyl and the like, 2,4-dichlorophenyl, 2,4,6-trichlorophenyl groups. The reaction proceeds through the intermediate formation of compound of general formula (XIX).

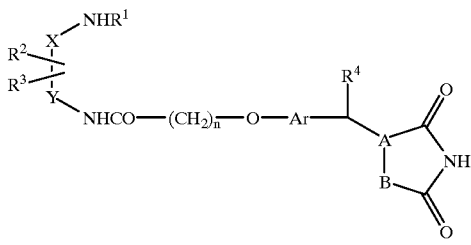

(XIX)

where all symbols $R^1$, $R^2$, $R^3$, $R^4$, X, Y, A, B, Ar and n are as defined earlier.

The group X—$NHR^1$ in formula (XIX) can also be generated by conventional methods such as amidation of an ester group (XOR) or partial hydrolysis of a CN (in a compound where CN group is present in the place of X—$NHR^1$) group.

The reaction of compound of general formula (XVII) with a compound of general formula (XVIII) to produce a compound of general formula (I) may be carried out in neat or in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar or He. The reaction may be carried out at a temperature in the range of 50° C. to 200° C., preferably at a temperature in the range of 60° C. to 180° C. The reaction may be effected in the presence or in absence of a base or an acid. The nature of the base or the acid is not critical. Example of such bases include organic bases such as pyridine, lutidine, triethyl amine, diisopropylethyl amine and the like, metal carbonates such as $K_2CO_3$, $Na_2CO_3$. Examples of acids include organic acids such as AcOH, $C_2H_5COOH$, butyric acid, p-toluenesulfonic acid, benzenesulfonic acid and the like, mineral acids such as HCl, HBr etc. The duration of the reaction may range from 0.25 to 48 hours, preferably from 0.50 to 18 hours.

Alternatively, the novel intermediate of formula (XIX) may be isolated and then cyclised to yield a compound of formula (I).

The reaction of compound of the formula (XVII) with a compound of formula (XVIII) to yield a compound of the formula (XIX) may be carried out neat or in presence of solvent such as xylene, toluene, dioxane, DMF, DMSO, halogenated hydrocarbons such as $CH_2Cl_2$, $CHCl_3$, $ClCH_2CH_2Cl$ and the like or mixtures thereof. The reaction may be effected hi the presence or absence of a base or an acid. The nature of the base or acid is not critical. Examples of such bases include organic bases such as pyridine, lutidine, triethyl amine, diisopropylethyl amine and the like. Examples of acids used for this reaction includes $CH_3COOH$, $C_2H_5COOH$, butyric acid, benzenesulfonic acid, p-toluenesulfonic acid and the like. The reaction may be carried out in au inert atmosphere which may be maintained by using inert gases such as $N_2$, Ar or He. The reaction may be carried out at a temperature in the range of 25° C. to 180° C., preferably in the range of 25° C. to 100° C. The reaction is generally instantaneous and the duration of the reaction may range from 0.25 to 24 h, preferably 0.25 to 2 h.

The cyclisation of the compound of formula (XIX) to yield a compound of the formula (I) may be carried out neat or in the presence of solvents such as THF, toluene, xylene, 1,4-dioxane and the like or mixtures thereof The reaction temperature may range from 60° C. to 150° C. depending upon the solvent employed and in the range from 100° C. to 200° C. when the reaction is carried out neat. The reaction may be effected in presence or absence of acids. The acids normally used include acetic acid, propionic acid, butyric acid, pTsOH and the like. The amount of acid used may range from 0.1 to 100 equivalents, preferably 0.1 to 10 equivalents. The reaction can also be carried out in neat acid. The reaction is preferably carried out in solvents such as THF, toluene, xylene, 1,4-dioxane or mixtures thereof in the presence of ail acid such as acetic acid, propionic acid, p-TsOH and the like. The duration of the reaction may range from 3 to 48 h preferably from 4 to 18 h.

The process described in the above embodiment is novel and unique since the heterocycle has been built in the final step of the process. In the present process no side products are observed. The yields are high and no purification is required for any intermediate involved. The process described in the above embodiment does not involve any stringent conditions This process works well for both small scale and large scale reactions. The process described in the above embodiment is preferably used for compounds of formula (I) wherein $R^2$ and $R^3$ together form a cyclic structure as defined earlier with Y, wherein Y represents C=C.

The compound of general formula (XVIII) where D represents —COOH and all other symbols are as defined earlier is prepared from the compound of general formula (XVIII) where D represents —COOR where R is a lower algal group such as $CH_3$, $C_2H_5$, $C_3H_7$ and all other symbols are as defined earlier by conventional hydrolysis procedures.

The hydrolysis of the compound of formula (XVIII) where D represents COOR group to yield a compound of the formula (XVIII) where D represents COOH group, may be carried out in the presence of solvents such as methanol, ethanol, dioxane, ether, THF, water and the like or mixtures thereof. The reaction may be effected in the presence of a base such as an alkali like NaOH, KOH or alkali metal carbonates like sodium carbonate, potassium carbonate and the like. The amount of base may range from 1 to 5 equivalents. The reaction may be carried out at a temperature in the range of 0° C. to 120° C., preferably at a temperature in the range of 15° C. to 100° C. The duration of the reaction may range from 0.25 to 24 h, preferably from 0.5 to 5 h.

The compound of general formula (XVIII) where D represents COCl or COBr and other symbols are as defined earlier may be prepared by the reaction of compound of general formula (XVIII) where D represents COOH and other symbols are as defined earlier with reagents such as $SOCl_2$, $PCl_3$, $PCl_5$, $PBr_3$ and the like. The reaction may be carried out neat or in the presence of solvents such as benzene, xylene etc. The reaction may be carried out in the range of 0° C. to 140° C. preferably in the range of 25° C. to 100° C. The duration of the reaction may range from 0.25 to 24 h, preferably 0.5 to 5 h.

The compound of general formula (XVIII) where all symbols are as defined earlier and D represents —C(=O)—O—(C=O)—$R^9$, where $R^9$ represents a linear or branched ($C_1$–$C_5$) alkyl group, dichlorophenyl, trichlorophenyl group and the like, may be prepared by the reaction of compound of general formula (XVIII) where D represents COOH and all other symbols are as defined earlier, with organic acid halides such as acetyl chloride, acetyl bromide, propanoyl chloride, butanoyl chloride, pivaloyl chloride, trichlorobenzoylchloride and the like in the presence of a base such as pyridine, N,N-dimethylaminopyridine, triethyl amine, diisopropylethyl amine, lutidine and the like or a mixture thereof. The reaction may be carried out in solvents such as $CH_2Cl_2$, $CHCl_3$, $ClCH_2CH_2Cl$, 1,4-dioxane, xylene and the like. The reaction may be carried out at a temperature in the range of 0° C. to 120° C., preferably in the range of 0° C. to 50° C. The duration of the reaction may range from 0.25 to 12 h, preferably 0.5 to 5 h.

Particularly useful compound of general formula (I) where X represents C=O, Y represents C=C, Z represents =C, n represents an integer 1, $R^1$ represents methyl group, B represents sulfur atom, $R^2$ and $R^3$ together with Y form a phenyl ring represented by formula (XX) can be prepared according to the process described in the above embodiment comprising:

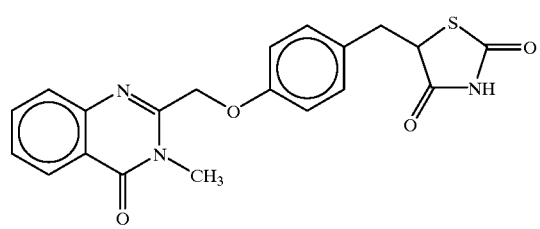

a) Reducing a compound of formula (XXI) which is disclosed in JP 2558473

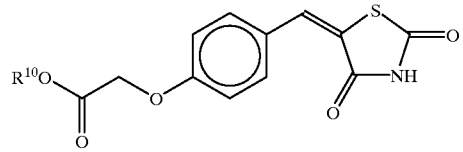

where $R^{10}$ is a lower alkyl group such as methyl, ethyl and the like using conventional reduction conditions to yield a compound of formula (XXII)

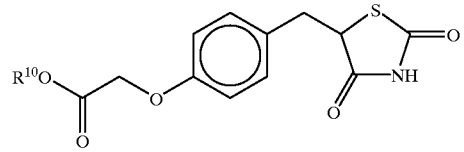

where $R^{10}$ is as defined above.

The reduction of compound of the formula (XXI) to yield a compound of the formula (XXII) may be carried out in the presence of gaseous hydrogen and a catalyst such as Pd/C or Raney nickel. Mixtures of catalysts may be used. Solvents such as dioxane, acetic acid ethyl acetate and the like may be used. A pressure between atmospheric pressure and 80 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol.

b) Hydrolysis of compound of formula (XXII) using conventional conditions to yield a compound of formula (XXIII)

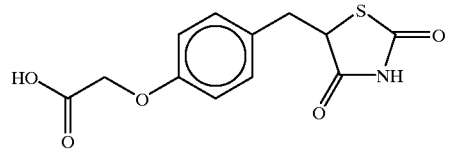

The hydrolysis of the compound of formula (XXII) to yield a compound of the formula (XXIII) may be carried out in the presence of solvents such as methanol, ethanol, dioxane, ether, THF, water and the like or mixtures thereof. The reaction may be effected in the presence of a base such as alkali like NaOH, KOH, alkali metal carbonates like sodium carbonate and potassium carbonate. The amount of base may range from 1 to 5 equivalents, based on the amount of the compound of formula (XXII). The reaction may be carried out at a temperature in the range of 0° C. to 120° C., preferably at a temperature in the range of 15° C. to 100° C. The duration of the reaction may range from 0.25 to 24 h, preferably from 0.5 to 5 h.

c) Reacting a compound of formula (XXIII) with acid halide or halogenating agent to obtain a compound of formula (XXIV),

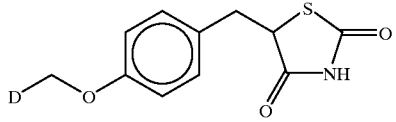

where D represents COCl or COBr or —C(=O)—O—(C=O)—R⁹, where R⁹ represents methyl or t-butyl group.

The reaction of compound of formula (XXIII) with halogenating agent such as $SOCl_2$, $PCl_5$, $PBr_3$ may be carried out neat or in presence of solvent such as benzene, xylene etc. The reaction may be carried out at 0° C. to 140° C., preferably at 25° C. to 100° C. The duration of the reaction may range from 0.25 to 24 h, preferably 0.5 to 5 h. The reaction of compound of formula (XXIII) with acid halide to yield mixed anhydride, may be carried out with acid halides such as acetyl chloride or pivaloyl chloride in the presence of a base such as pyridine, triethyl amine-N,N-dimethylamino pyridine or mixtures thereof. The amount of base may range from 1 to 5 equivalents, based on the amount of the compound of formula (XXIII). The reaction may be carried out in solvents like dichloromethane, chloroform, dichloroethane, 1,4-dioxane, xylene and the like. The reaction may be carried out at a temperature in the range of 0° C. to 120° C., preferably at a temperature in the range of 15° C. to 50° C. The duration of the reaction may range from 0.25 to 12 h preferably from 0.5 to 5 h.

d) Reaction of compound of formula (XXIV) with a compound of formula (XXV)

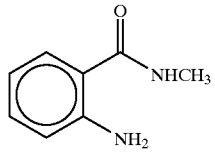

to yield a compound of formula (XX) defined above. The reaction proceeds through the intermediate formation of compound of formula (XXVI).

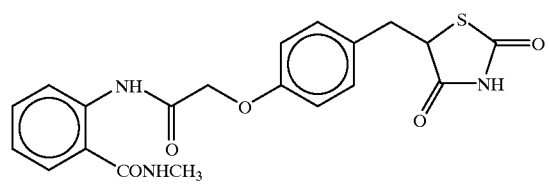

The reaction of compound of formula (XXIV) with a compound of formula (XXV) to produce a compound of general formula (XX) may be carried out in neat or in the presence of solvents such as xylene, toluene, THF, dioxane, acetic acid, DMF, DMSO and the like or mixtures thereof. The reaction may be carried out in au inert atmosphere which may be maintained by using inert gases such as $N_2$, Ar or He. The reaction may be carried out at a temperature in the range of 50° C. to 200° C., preferably at a temperature in the range of 80° C. to 180° C. The reaction may be effected in the presence of an acid. The nature of the acid is not critical. Examples of acids include organic acids such as AcOH, $C_2H_5COOH$, p-toluenesulfonic acid and the like, mineral acids such as HCl, HBr etc. The duration of the reaction may range from 0.25 to 48 hours, preferably from 0.50 to 18 hours, based on solvent, temperature and acid used.

Alternatively, the novel intermediate of formula (XXVI)) may be isolated and then cyclised to yield a compound of formula (XX).

The reaction of compound of the formula (XXIV) with a compound of formula (XXV) to yield a compound of the formula (XXVI) may be carried out neat or in presence of solvent such as xylene, toluene, dioxane, DMF, DMSO halogenated hydrocarbons such as $CH_2Cl_2$, $CHCl_3$, $ClCH_2CH_2Cl$ and the like or mixtures thereof. The reaction may be effected in the presence of an acid. The nature of the acid is not critical. Examples of acids used for this reaction includes $CH_3COOH$, $C_2H_5COOH$, butyric acid, benzenesulfonic acid, p-toluenesulfonic acid and the like. The reaction may be carried out in an inert atmosphere which may be maintained by using inert gases such as $N_2$, Ar or He. The reaction may be carried out at a temperature in the range of 25° C. to 180° C., preferably in the range of 25° C. to 60° C. The reaction is generally instantaneous and the duration of the reaction may range from 0.25 to 12 h, preferably 0.25 to 2 h.

The cyclisation of the compound of formula (XXVI) to yield a compound of the formula (XX) may be carried out neat or in the presence of solvents such as THF, toluene, xylene, 1,4-dioxane and the like or mixtures thereof The reaction temperature may range from 60° C. to 150° C. depending upon the solvent employed and in the range from 100° C. to 200° C. when the reaction is carried out neat. The reaction may be effected in the presence of acids. The acids normally used include acetic acid, propionic acid, and pTsOH. The amount of acid used may range from 0.1 to 100 equivalents, preferably 0.1 to 10 equivalents. The reaction can also be carried out in neat acid. The reaction is preferably carried out in solvents such as THF, toluene, xylene, 1,4-dioxane or mixtures thereof in the presence of an acid such as acetic acid, propionic acid, p-TsOH and the like. The duration of the reaction may range from 3 to 48 h preferably from 4 to 18 h, based on solvent, temperature and acid used.

The term neat as used herein means the reaction is carried out without the use of solvent.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol dioxane, isopropanol, ethanol etc. Mixture of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid. phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as rucine, cinchona alkaloids and their derivatives and the like.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffractogram or such other techniques.

The present invention also provides a pharmaceutical composition, containing the compounds of the general formula (I), as defined above, their tautomeric forms, their stereoisomers, their polymorphs, their pharmaceutically acceptable salts, their pharmaceutically acceptable solvates in combination with the usual pharmaceutically employed carriers, diluents and the like, useful for the treatment and/or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis, insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 20%. preferably 1 to 10% by weight of active compound, the remainder of the composition being pharmaceutically acceptable carriers, diluents or solvents.

A typical tablet production method is exemplified below:

| Tablet Production Example: | |
|---|---|
| a) 1) Active ingredient | 10 g |
| 2) Lactose | 110 g |
| 3) Corn starch | 35 g |

| -continued | |
|---|---|
| Tablet Production Example: | |
| 4) Carboxymethyl cellulose | 44 g |
| 5) Magnesium stearate | 1 g |
| | 200 g for 1000 tablets |

The ingredients 1 to 3 are uniformly blended with water and granulated after drying under reduced pressure. The ingredient 4 and 5 are mixed well with the granules and compressed by tabletting machine to prepare 1000 tablets each containing 10 mg of active ingredient.

| b) 1) Active ingredient | 10 g |
|---|---|
| 2) Calcium phosphate | 90 g |
| 3) Lactose | 50 g |
| 4) Corn starch | 45 g |
| 5) Polyvinyl pyrrolidone | 3.5 g |
| 6) Magnesium stearate | 1.5 g |
| | 200 g for 1000 tablets |

The ingredients 1 to 4 are uniformly moistened with an aqueous solution of ingredient 5 and granulated after drying under reduced pressure. Ingredient 6 is added and granules are compressed by a tabletting machine to prepare 1000 tablets containing 10 mg of active ingredient 1.

The compound of the formula (I) as defined above are clinically administered to mammals, including man, via either oral or parenteral routes. Administration by the oral route is preferred being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 200 mg/kg body weight of the subject per day or preferably about 0.10 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

4-[2-[4-Methyl-2-propyl-6-oxo-1,6-dihydro-1-pyrimidinyl]ethoxy]benzaldehyde

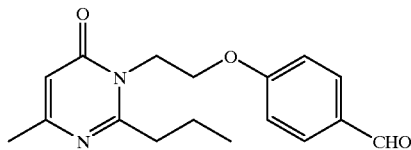

To a stirred suspension of NaH (570 mg, 22.57 mmol 95%) in dry DMF (35 ml) at 25° C. was added a solution of 4-methyl-2-propyl-1,6-dihydro-6-pyrimidone (2.64 g, 17.36 mmol) in dry DMF. After the effervescence has ceased, anhydrous LiBr (3.51 g, 40.0 mmol) was added followed by 4-[2-bromoethoxy]benzaldehyde (4.37 g, 19.08 mmol) in dry DMF at the same temperature. The reaction mixture was immersed in a preheated oil bath at 70° C. and stirred for 2 h. The reaction mixture was cooled to room temperature, poured into water and extracted with EtOAc. The combined EtOAc layers were washed with brine, dried over anhydrous $Na_2SO_4$ and concentrated. The crude compound was chromatographed over silica gel using 3 7 EtOAc—pet. ether as eluent to obtain the title compound (1.61 g, 31%).

$^1$H NMR(CDCl$_3$): δ9.80 (s, 1H), 7.82 (d, J=8.72 Hz, 2H), 6.95 (d, J 8.72 Hz, 2H), 6.20 (s, 1H) 4.45 (t, J=5.30 Hz, 2H), 4.35 (t, J=5.30 Hz, 2H), 2.92 (t, J=7.50 Hz, 2H), 2.25 (s, 3H), 1.92–1.70 (m, 2H), 1.20 (t, J=7.50 Hz, 3H).

Preparation 2

4-[2-[2,4-Dimethyl-6-oxo-1,6-dihydro-1-pyrimidinyl]ethoxy]benzaldehyde

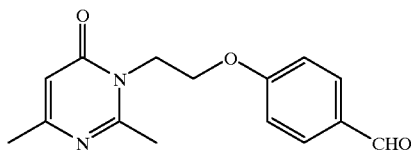

The title compound (0.8 g, 30%) was prepared from 2,4-dimethyl-1,6-dihydro-6-pyrimidone (1.3 g, 10.48 mmol) and 4-[2-bromoethoxy]benzaldehyde (2,4 g, 10.48 mmol) in the presence of a base $K_2CO_3$ (2.89 g, 20.96 mmol) by a similar procedure as described in preparation 1.

$^1$H NMR (CDCl$_3$) δ9.90 (s, 1H), 7.80 (d, J=8.70 Hz, 2H), 7.02 (d, J=8.70 Hz, 2H), 6.20 (s, 1H), 4.50–4.30 (m, 4H), 2.70 (s, 3H), 2.20 (s, 3H).

Preparation 3

4-[2-[2-Ethyl-4-methyl-6-oxo-1,6-dihydro-1-pyrimidinyl]ethoxy]benzaldehyde

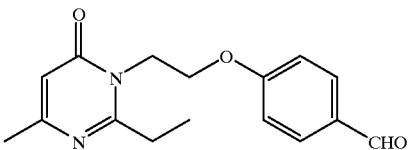

The title compound (1.7 g, 42%) was prepared from 2-ethyl-4-methyl-1,6-dihydro-6-pyrimidone (2.0 g, 14.49 mmol) 4-[2-bromoethoxy]benzaldehyde (3.32 g, 14.49 mmol), LiBr (2.9 g, 33.33 mmol) and NaH (0.45 g, 18.84 mmol) as base, by a similar procedure to that described in preparation 1.

$^1$H NMR (CDCl$_3$): δ9.90 (s, 1H), 7.80 (d, J=8.70 Hz, 2H), 6.98 (d, J=8.70 Hz, 2H), 6.20 (s, 1H), 4.52–4.25 (m, 4H), 3.02 (q, J=7.40 Hz, 2H), 2.30 (s, 3H), 1.40 (t, J=7.40 Hz, 3H),

Preparation 4

4-[2-[2-Butyl-4-methyl-6-oxo-1,6-dihydro-1-pyrimidinyl]ethoxy]benzaldehyde

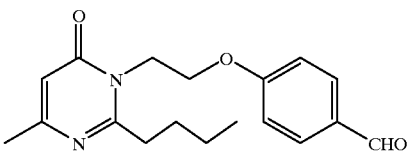

The title compound (1.1 g, 25%) was prepared from 2-butyl-4-methyl-1,6-dihydro-6-pyrimidone (2.3 g, 13.85 mmol), 4-[2-bromoethoxy]benzaldehyde (3.17 g, 13.85 mmol) in the presence of $K_2CO_3$ (3.82 g, 27.7 mmol) as base by a similar procedure to that described in preparation 1.

$^1$H NMR (CDCl$_3$): δ9.90 (s, 1H), 7.84 (d, J=8.72 Hz, 2H), 6.98 (d, J=8.72 Hz, 2H), 6.20 (s, 1H), 4.52–4.30 (m, 4H), 2.96 (t, J=7.47 Hz, 2H), 2.26 (s, 3H), 1.90–1.70 (m, 2H), 1.70–1.50 (m, 2H), 1.01 (t, J=7.47 Hz, 3H).

Preparation 5

4-[2-[2-Benzyl-4-methyl-6-oxo-1,6-dihydro-1-pyrimidinyl]ethoxy]benzaldehyde

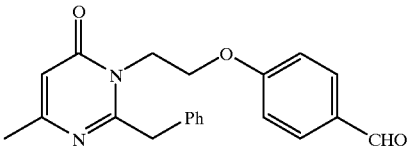

The title compound (2.0 g, 20.6%) was prepared from 2-benzyl-4-methyl-1,6-dihydro-6-pyrimidone (5.6 g, 28.0 mmol), 4-[2-bromoethoxy]benzaldehyde (17.05 g, 30.1 mmol) in the presence of 95% NaH (873 mg, 35.0 mmol) as base by a similar procedure to that described in preparation 1.

$^1$ H NMR (CDCl$_3$): δ9.89 (s, 1H), 7.83 (d, J=8.72 Hz, 2H), 7.45–7.15 (m, 5H), 6.98 (d, J=8.72 H, 2H), 6.44 (s, 1H), 4.70 (t, J=4.71 Hz, 2H), 4.30 (t, J=4.71 Hz, 2H), 4.14 (s, 2H), 2.42 (s, 3H).

Preparation 6

4-[2-[2,5-Diethyl-4-methyl-6-oxo-1,6-dihydro-1-pyrimidinyl]ethoxy]benzaldehyde

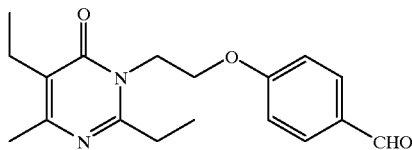

The title compound (1.42 g, 28%) was prepared from 2,5-diethyl-4-methyl-1,6-dihydro-6-pyrimidone (2.70 g, 16.26 mmol) and 4-[2-bromoethoxy]benzaldehyde (4.09 g, 17.86 mmol) in the presence of 95% NaH (508 mg, 20 mmol) as base by a similar procedure to that described in preparation 1.

$^1$H NMR (CDCl$_3$): δ9.88 (s, 1H), 7.82 (d, J=8.62 Hz, 2H), 6.97 (d, J=8.62 Hz, 2H), 4.50–4.20 (m, 4H), 2.95 (q, J=7.47 Hz, 2H), 2.52 (q, J=7.47 Hz, 2H), 2.28 (s, 3H), 1.34 (t, J=7.47 Hz, 3H), 1.09 (t, J=7.47 Hz, 3H).

Preparation 7

4-[2-[2-Ethyl-4phenyl-6-oxo-1,6-dihydro-1-pyrimidinyl]ethoxy]benzaldehyde

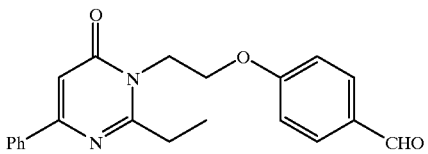

The title compound (2.0 g, 44%) was prepared from 2-ethyl-4-phenyl-1,6-dihydro-6-pyrimidone (2.6 g, 13.0 mmol), 4-[2-bromoethoxy]benzaldehyde (2.97 g, 13.0 mmol) and LiBr (2.59 g, 29.9 mmol) in the presence of NaH as base (0.4 g, 16.9 mmol) by a similar procedure to that described in preparation 1.

$^1$H NMR (CDCl$_3$) δ9.89 (s, 1H), 8.10–7.95 (m, 2H), 7.83 (d, J=8.72 Hz, 2H), 7.55–7.45 (m, 3H), 6.98 (d, J=8.72 Hz, 2H), 6.78 (s, 1H), 4.60–4.40 (m, 4H), 3.08 (q, J=7.30 Hz, 2H), 1.48 (t, J=7.30 Hz, 3H).

Preparation 8

4-[2-[4-N-Acetylamino-2-oxo-1,2-dihydro-1-pyrimidinyl]ethoxy]benzaldehyde

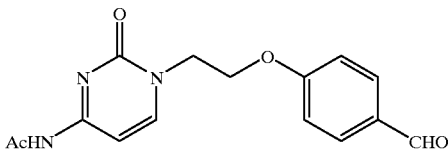

The title compound (1.8 g, 66%) was prepared from 4-acetylamino-1,2-dihydro-2-pyrimidone (1.8 g, 11.9 mmol) and 4-[2-bromoethoxy]benzaldehyde (2.72 g, 11.9 mmol) in the presence of K$_2$CO$_3$ (3.28 g, 23.8 mmol) as base by a similar procedure to that described in preparation 1.

$^1$H NMR (CDCl$_3$): δ9.90 (s, 1H), 8.70 (bs, 1H, D$_2$O exchangeable), 7.85 (d, J=8.70 Hz, 2H), 7.75 (d, J=7.80 Hz, 1H), 7.42 (d, J=7.80 Hz, 1H), 6.95 (d. J=8.70 Hz, 2H), 4.40–4.20 (m, 4H) 2.30 (s, 3H).

Preparation 9

4-[2-[4-Oxo-3,4-dihydro-3-quinazolinyl]ethoxy]benzaldehyde

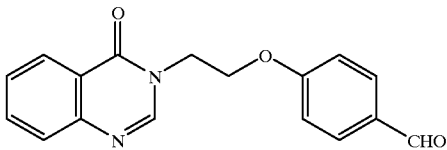

The title compound (1.5 g, 73%) was prepared from 4-oxo-3,4-dihydroquinazoline (1.03 g, 7.05 mmol) and 4-[2-bromoethoxy]benzaldehyde (1.77 g, 7.7 mmol) in the presence of K$_2$CO$_3$ (2.0 g, 14.5 mmol) as base, by a similar procedure to that described in preparation 1.

$^1$H NMR (CDCl$_3$) δ9.88 (s, 1H), 8.32 (d, J=7.88 Hz, 1H), 8.21 (s, 1H), 7.88–7.70 (m, 2H), 7.82 (d, J=8.72 Hz, 2H), 7.60–7.42 (m, 1H), 7.00 (d, J=8.72 Hz, 2H), 4.55–4.25 (m, 4H).

Preparation 10

4-[2-[2-Methyl-4-oxo-3,4-dihydro-3-quinazolinyl]ethoxy]benzaldehyde

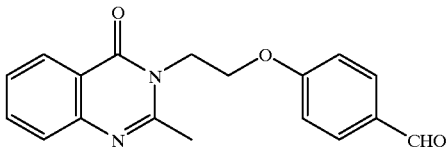

The title compound (0.6 g, 39%) was prepared from 2-methyl-4-oxo-3,4-dihydroquinazoline (0.8 g, 5 mmol) and 4-[2-bromoethoxy]benzaldehyde (1.37 g, 6 mmol) in the presence of K$_2$CO$_3$ (1.38 g, 10.0 mmol) as base, by a similar procedure to that described in preparation 1.

$^1$H NMR (CDCl$_3$): δ9.85 (s, 1H), 8.13 (d, J=8.0 Hz, 1H), 7.84–7.72 (m, 3H), 7.59–7.41 (m, 2H), 7.10 (d, J=7.0 Hz, 2H), 4.50–4.40 (m, 2H), 4.40–4.30 (m, 2H), 2.76 (s, 3H).

Preparation 11

4-[2-[2-Ethyl-4-oxo-3,4-dihydro-3-quinazolinyl]ethoxy]benzaldehyde

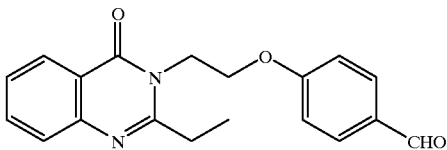

The title compound (5.0 g, 27%) was prepared from 2-ethyl-4-oxo-3,4-dihydroquinazoline (9.2 g, 57.5 mmol) and 4-(2-bromoethoxy)benzaldehyde (14.5 g, 69.0 mmol) in the presence of K$_2$CO$_3$ (14.6 g, 115.0 mmol) as base, by a similar procedure to that described in preparation 1.

$^1$H NMR (CDCl$_3$): δ9.86 (s, 1H), 8.14 (d, J=8.0 Hz, 1H), 7.87–7.76 (m, 3H), 7.65–4.45 (m, 2H), 7.13 (d, J=8.0 Hz,

2H), 4.60–4.50 (m, 2H). 4.50–4.40 (m, 2H), 3.07 (q, J=7.0 Hz, 2H), 1.35 (t, J=7.0 Hz, 3H).

Preparation 12

4-[2-[8-Aza-2-methyl-4-oxo-3,4-dihydro-3-quinazolinyl]ethoxy]benzaldehyde

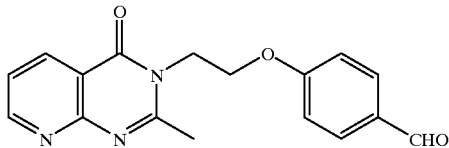

The title compound (0.26 g, 41%) was prepared from 8-aza-2-methyl-4-oxo-3 4-dihydro quinazoline (0.33 g, 2.0 mmol) 4-[2-bromoethoxy]benzaldehyde (0.52 g, 2.25 mmol) in the presence of $K_2CO_3$ (0.57 g, 4.1 mmol) as base by a similar procedure to that described in preparation 1.

$^1$H NMR (CDCl$_3$): δ9.87 (s, 1H), 9.02–8.90 (m. 1H), 8.58 (d, J=7.30 Hz, 1H), 7.82 (d, J=8.72 Hz. 2H), 7.48–7.35 (m, 1H), 6.97 (d, J=8.72 Hz 2H), 4.58 (t, J=4.72 Hz, 2H) 4.43 (t, J=4.72 Hz, 2H), 2.91 (s, 3H).

Preparation 13

4-[[3-Methyl-4-oxo-3,4-dihydro-2-quinazolinyl]methoxy]benzaldehyde

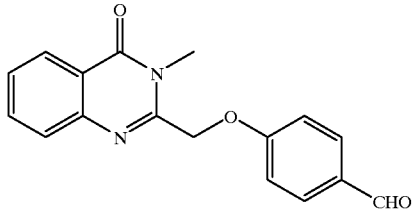

A mixture of 4-hydroxybenzaldehyde (3.21 g, 26.3 mmol) and $K_2CO_3$ (3.64 g, 26.3 mmol) in dry DMF (50 ml) was stirred for 15 min at 30° C. To the above stirred mixture a solution of 2-chloromethyl-3-methyl-4-oxo-3,4-dihydroquinazoline (5.0 g, 24.0 mmol) was added and stirred further for 90 minutes at the same temperature. The reaction mixture was diluted with EtOAc (200 ml). washed with aqueous $Na_2CO_3$ solution (3×50 ml) and then with brine, dried over anhydrous $Na_2SO_4$ and concentrated to yield the title compound (5.08 g, 72%).

$^1$H NMR (CDCl$_3$): δ9.89 (s, 1H), 8.29 (d, J=7.89 Hz, 1H), 7.85 (d, J=8.71 Hz, 2H), 7.80–7.62 (m, 2H), 7.52 (t, J=7.81 Hz, 1H), 7.19 (d, J=8.71 Hz, 2H), 5.27 (s, 2H), 3.74 (s, 3H).

Preparation 14

4-[[3-Ethyl-4-oxo-3,4-dihydro-2-quinazolinyl]methoxy]benzaldehyde

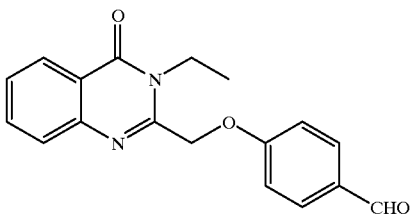

The title compound (4.24 g, 88%) was prepared from 2-chloromethyl-3-ethyl-4-oxo-3,4-dihydro-quinazoline (3,5 g, 15.7 mmol) and 4-hydroxybenzaldehyde (2.10 g, 17.21 mmol) in the presence of $K_2CO_3$ (2.38 g, 17.26 mmol) as base by a similar procedure to that described in preparation 13.

$^1$H NMR (CDCl$_3$): δ9.91 (s, 1H), 8.31 (d, J=7.89 Hz. 1H), 7.88 (d, J=8.72 Hz, 2H), 7.82–7.68 (m, 2H), 7.65–7.45 (m, 1H), 7.22 (d, J=8.72 Hz, 2H), 5.28 (s, 2H), 4.28 (q, J=7.06 Hz, 2H), 1.41 (t, J=7.06 Hz, 3H).

Preparation 15

4-[[1-methyl-4-oxo-1,4-dihydro-2-quinazolinyl]methoxy]benzaldehyde

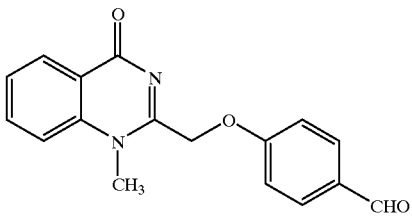

The title compound (364 mg, 65%) was prepared from 2-chloromethyl-1-methyl-4-oxo-1,4-dihydroquinazoline (416 mg, 2.0 mmol) and 4-hydroxybenzaldehyde (244 mg, 2.0 mmol) in the presence of $K_2CO_3$ (276 mg, 2.0 mmol) as base by a similar procedure to that described in preparation 13.

$^1$H NMR (CDCl$_3$): δ9.88 (s, 1H), 8.34 (d, J=7.89 Hz, 1H), 7.83 (d, J=8.71 Hz, 2H), 7.80 7.70 (m, 1H), 7.60–7.40(m, 2H), 7.22 (d, J=8.71 Hz, 2H), 5.34 (s, 2H), 3.91 (s, 3H).

Preparation 16

3-Methoxy-4-[[3-Methyl-4-oxo-3,4-dihydro-2-quinazolinyl]methoxy]benzaldehyde

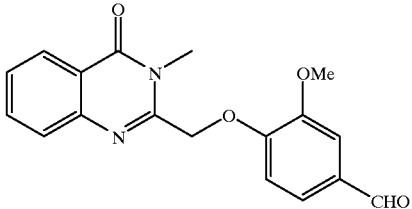

The title compound (250 mg, 77%) was obtained from 2-chloromethyl-3-methyl-4-oxo-3,4-dihydroquinazoline (209 mg, 1.0 mmol) and vanillin (167 mg, 1.1 mmol) in the presence of $K_2CO_3$ (276 mg, 2.0 mmol) as base by a similar procedure to that described in preparation 13.

$^1$H NMR (CDCl$_3$): δ9.88 (s, 1H), 8.29 (d, J=8.30 Hz, 1H), 7.80–7.62 (m, 2H), 7.58–7.39 (m, 2H), 7.26 (d, J=8.30 Hz, 2H), 5.30 (s, 2H), 3.90 (s, 3H), 3.78 (s, 3H).

Preparation 17

4-[2-[2-Ethyl-4-methyl-6-oxo-1,6-dihydro-1-pyrimidinyl]ethoxy]benzaldehyde Oxime

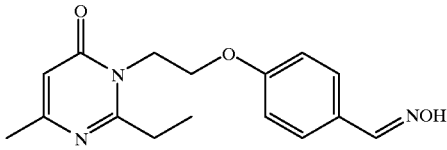

To a stirred solution of hydroxylamine hydrochloride (10.0 g, 143.0 mmol) and sodium acetate trihydrate (20.0 g, 146.9 mmol) in water (100 ml) at 30° C. was added a hot solution of 4-[2-[2-ethyl-4-methyl-6-oxo-1,6-dihydro-1-pyrimidinyl]ethoxy]benzaldehyde (5.72 g, 20.0 mmol) (obtained from preparation 3) in ethanol (100 ml). The reaction mixture was immersed in a preheated oil bath (95° C.) and refluxed for 3 h. The reaction mixture was then cooled to room temperature and concentrated to a volume where crystals of oxime started separating out and the mixture was kept aside for 30 min. to 1 h at 25° C. The resultant crystals were filtered and washed with water and dried to obtain the title compound (5.42 g, 90%).

$^1$H NMR (CDCl$_3$+DMSO-d$_6$): δ10.56 (s, 1H, OH, D$_2$O exchangeable), 8.08 (s, 1H), 7.55 (d, J=8.56 Hz, 2H) 6.88 (d, J=8.56 Hz, 2H), 6.20 (s, 1H), 4.51–4.40 (m, 2H), 4.40–4.28 (m, 2H), 3.05 (q, J=7.06 Hz, 2H), 2.30 (s, 3H), 1.40 (t, J=7.06 Hz, 3H).

Preparation 18

4-[2-[2-Ethyl-4-methyl-6-oxo-1,6-dihydro-1-pyrimidinyl]ethoxy]benzylhydroxylamine

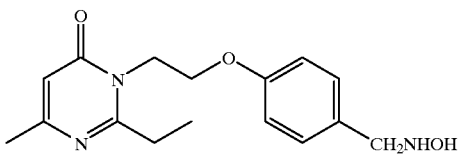

To a stirred solution of 4-[2-[2-ethyl-4-methyl-6-oxo-1,6-dihydro-1-pyrimidinyl]ethoxy]benzaldehyde oxime (301 mg, 1.0 mmol) (obtained from preparation 17) in a mixture of methanol (7 ml) and THF (3 ml) was added 4 N HCl (2 ml) in dioxane at 30° C. and stirred for 10 min. at the same temperature. The reaction mixture was basified to pH 9 with 1 N NaOH and extracted with EtOAc (3×10 ml). The combined organic layers were washed with brine and dried over anhydrous Na$_2$SO$_4$ and concentrated to yield the of title compound (272 mg, 90%).

$^1$H NMR (CDCl$_3$): δ7.23 (d, J=8.72 Hz, 2H), 6.80 (d, J=8.72 Hz, 2H), 6.18 (s, 1H), 4.45–4.35 (m, 2H), 4.35–4.20 (m, 2H), 3.98 (s, 2H), 3.01 (q, J=7.56 Hz, 2H), 2.22 (s, 3H), 1.32 (t, J=7.56 Hz, 3H).

Preparation 19

N-[4-[2-[2-Ethyl-4-methyl-6-oxo-1,6-dihydro-1-pyrimidinyl]ethoxy]benzyl]N-hydroxyurea

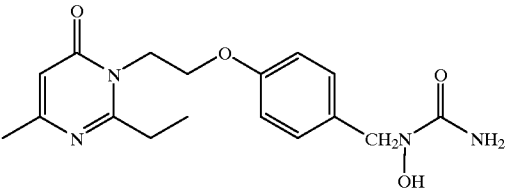

To a stirred solution of 4-[2-[2-ethyl-4-methyl-6-oxo-1,6-dihydro-1-pyrimidinyl]ethoxy]benzyl hydroxylamine (303 mg, 1.0 mmol) (obtained from preparation 18) in a mixture of water (2 ml) and acetic acid (0.5 ml) was added a solution of KOCN (343 mg, 3.0 mmol) in water (I ml) and stirred for 1 h at 30° C. The reaction mixture was diluted with water and extracted with ethyl acetate (3×10 ml). The combined organic layers were washed with brine, dried over anhydrous Na$_2$SO$_4$ and concentrated to yield the compound (295 mg, 85%).

$^1$H NMR (CDCl$_3$): δ7.18 (d, J=8.65 Hz, 2H), 6.90 (d, J=8.65 Hz, 2H), 6.60 (bs, 1H, D$_2$O exchangeable), 6.15 (s, 1H), 5.85 (bs, 1H, D$_2$O exchangeable), 4.70 (s, 2H), 4.50 (bs, 1H, D$_2$O exchangeable), 4.40–4.30 (m, 2H), 4.22–4.10 (m, 2H), 2.92 (q, J=7.56 Hz, 2H), 2.20 (s, 3H), 1.20 (t, J=7.56 Hz, 3H).

Preparation 20

4-[2-[2-Ethyl-4-methyl-6-oxo-1,6-dihydro-1-pyrimidinyl]ethoxy]nitrobenzene

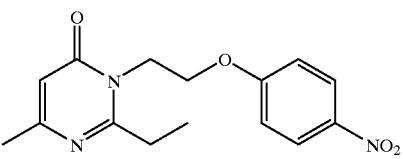

The title compound (5.2 g, 25%) was prepared from 2-ethyl-4-methyl-1,6-dihydro-6-pyrimidone (7.65 g, 55.43 mmol), 4-[2-bromoethoxy]nitrobenzene (15.0 g, 60.97 mmol), LiBr (11.09 g, 127.49 mmol) and 60% NaH (2.76 g, 72.06 mmol) as base by a similar procedure to that described in preparation 1.

$^1$H NMR (CDCl$_3$): δ8.20 (d, J=8.81 Hz, 2H), 6.94 (d, J=8.81 Hz, 2H), 6.22 (s, 1H), 4.55–4.42 (m, 2H), 4.42–4.34 (m, 2H), 2.99 (q, J=7.4 Hz, 2H), 2.27 (s, 3H), 1.38 (t, J=7.4 Hz, 3H).

Preparation 21

4-[2-[2-Ethyl-4-oxo-3,4-dihydro-3-quinazolinyl]ethoxy]nitrobenzene

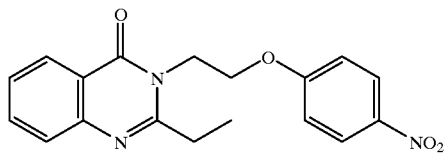

The title compound (1.246 g, 64%) was prepared from 2-ethyl-4-oxo-3,4-dihydroquinazoline (1.0 g, 5.7 mmol) and 4-[2-bromoethoxy]nitrobenzene (1.696 g, 6.8 mmol) and $K_2CO_3$ (1.58 g, 11.49 mmol) as a base by a similar procedure to that described in preparation 1.

$^1$H NMR ($CDCl_3$): δ8.24 (d, J=7.93 Hz, 1H), 8.18 (d, J=9.20 Hz, 2H), 7.82–7.61 (m, 2H), 7.46 (t, J=7.93 Hz, 1H), 6.94 (d, J=9.20 Hz, 2H), 4.58 (t, J=4.82 Hz, 2H), 4.44 (t, J=4.82 Hz, 2H), 3.09 (q, J=7.38 Hz, 2H), 1.46 (t, J=7.38 Hz, 3H).

Preparation 22

4-[2-[2-Ethyl-4-methyl-6-oxo-1,6-dihydro-1-pyrimidinyl]ethoxy]aniline

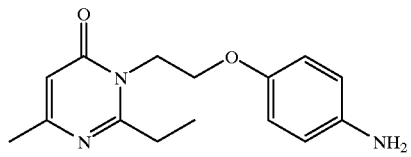

A solution of 4-[2-[2-ethyl-4-methyl-6-oxo-1,6-dihydro-1-pyrimidinyl]ethoxy]nitrobenzene (1.0 g. 3.3 mmol) (obtained from preparation 20) in 1.4-dioxane (20 ml) was reduced with hydrogen in the presence of 10% palladium on charcoal (100 mg) at 30 psi for 16 h. The mixture was filtered through a bed of celite and washed with dioxane and evaporated to dryness under reduced pressure to yield the title compound (625 mg, 70%).

$^1$H NMR ($CDCl_3$) δ6.78–6.52 (m, 4H), 6.18 (s, 1H), 4.38 (t, J=4.98 Hz, 2H), 4.19 (t, J=4.98 Hz, 2H), 2.99 (q, J=7.47 Hz, 2H), 2.24 (s, 3H), 1.33 (t, J=7.47 Hz, 3H).

Preparation 23

4-[2-[2-Ethyl-4-oxo-3,4-dihydro-3-quinazolinyl]ethoxy]aniline

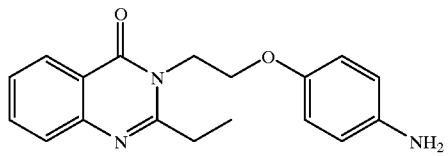

The title compound (1.107 g, 98%) was prepared from 4-[2-[2-ethyl-4-oxo-3,4-dihydro-3-quinazolinyl]ethoxy]nitrobenzene (1.246 g, 3.67 mmol) (obtained from preparation 21) by a similar procedure to that described in preparaton 22.

$^1$H NMR ($CDCl_3$): δ8.24 (d, J=7.93 Hz, 1H), 7.80–7.60 (m, 2H), 7.43 (t, J=7.93 Hz, 1H), 6.80–6.50 (m, 4H), 4.51 (t, J=5.19 Hz, 2H), 4.24 (t, J=5.19 Hz, 2H), 3.10 (q, J=7.34 Hz, 2H), 1.42 (t, J=7.34 Hz, 3H).

Preparation 24

Ethyl 2-Bromo-3-[4-[2-[2-ethyl-4-methyl-6-oxo-1,6-dihydro-1-pyrimidinyl]ethoxy]phenyl]propanoate

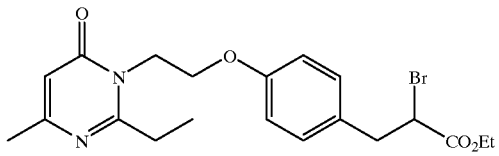

To a stirred solution of 4-[2-[2-ethyl-4-methyl-6-oxo-1,6-dihydro-1-pyrimidinyl]ethoxy]aniline (2.80 g, 10.26 mmol) (obtained from preparation 22) in acetone (10 ml) was added aqueous HBr (47%, 1 ml) and stirred for 10 min. at 0° C. To the above reaction mixture a solution of $NaNO_2$ (850 mg, 12.30 mmol) in water (1.7 ml) was added slowly dropwise at 0° C. and stirring was continued further for 30 min at the same temperature. To this reaction mixture, ethyl acrylate (6.77 ml, 62.0 mmol) was added and allowed to warm to 30° C. Catalytic amount of copper (1) iodide (20 mg) was added in one portion and the reaction mixture was stirred flier for 1 h at 30° C. Acetone was removed under reduced pressure and the resultant residue was extracted with EtOAc (3×10 ml). The combined EtOAc layers were washed with dilute NH3 solution, water, followed by brine; dried over anhydrous $Na_2SO_4$ and concentrated to afford the crude compound which was purified by flash chromatography using 40% EtOAc/petroleum ether as eluent to yield the title compound (2.47 g, 55%).

$^1$H NMR ($CDCl_3$): δ7.11 (d, J=8.63 H, 2H), 6.78 (d, J=8.63 Hz, 2H), 6.19 (s, 1H), 4.50–4.32 (m, 2H), 4.30–4.02 (m, 5H), 3.38 (dd, J=13.72, 8.31 Hz, 1H), 3.17 (dd, J=13.72, 7.06 Hz, 1H), 3.10–2.90 (m, 2H), 2.25 (s, 3H), 1.35 (t, J=7.47 Hz, 3H), 1.24 (t, J=7.05 Hz, 3H).

Preparation 25

Ethyl 2-Bromo-3-[4-[2-[2-ethyl-4-oxo-3,4-dihydro-3-quinazolinyl]ethoxy]phenyl]propanoate

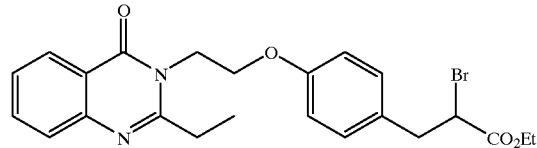

The title compound (671 mg, 55%) was prepared from 4-[2-[2-ethyl-4-oxo-3,4-dihydro-3-quinazolinyl]ethoxy]aniline (800 mg, 2.58 mmol) (obtained from preparation 23), $NaNO_2$ (214 mg, 3.1 mmol) and ethyl acrylate (1.7 ml, 1.574 g, 15.74 mmol) by a similar procedure to that described in preparation 24.

$^1$H NMR ($CDCl_3$): δ8.23 (d, J=7.88 Hz, 1H), 7.80–7.55 (m, 2H), 7.52–7.30 (m, 1H), 7.15–7.01 (m, 2H), 6.77 (d, J=8.71 Hz, 2H), 4.52 (t, J=5.03 Hz, 2H), 4.45–4.30 (m, 1H), 4.30 (t, J=5.03 Hz, 2H), 4.20–4.00 (m, 2H), 3.35 (dd, J=14.12, 8.71 Hz, 1H), 3.20–3.00 (m, 3H), 1.43 (t, J=7.34 Hz, 3H), 1.20 (t, J=7.34 Hz, 3H).

Preparation 26

5-[4-[2-[2-Ethyl-4-methyl-6-oxo-1,6-dihydro-1-pyrimidinyl]ethoxy]phenyl Methyl]-2-iminothiazolidine-4-one Hydrochloride

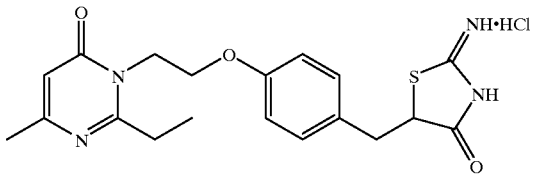

A mixture of ethyl 2-bromo-3-[4-[2-[2-ethyl-4-methyl-6-oxo-1,6-dihydro-1-pyrimidinyl]ethoxy]phenyl]propaneate (1.70 g, 3.89 mmol) (obtained from preparation 24), fused sodium acetate (637 mg, 7.78 mmol) and thiourea (592 mg, 7.78 mmol) in ethanol (10 ml) was refluxed for 12 h. The reaction mixture was cooled to room temperature and the resultant solid was filtered and dried to afford the title compound (1.35 g, 89%).

$^1$H NMR (CDCl$_3$): δ7.12 (d, J=8.59 Hz, 2H), 6.76 (d, J=8.59Hz, 2H), 6.12(s, 1H), 4.50–4.30 (m, 3H), 4.30–4.15 (m, 2H), 3.40 (dd, J=14.11, 3.74 Hz, 1H), 2.98 (q, J=7.47 Hz, 2H). 2.85 (dd, J=14.11, 9.43 Hz, 1H), 2.23 (s, 3H), 1.32 (t, J=7.47 Hz, 3H).

Preparation 27

5-[4-[2-[2-Ethyl-4-oxo-3,4-dihydro-3-quinazolinyl]ethoxy]phenyl Methyl]-2-imino thiazolidine-4-one Hydrochloride

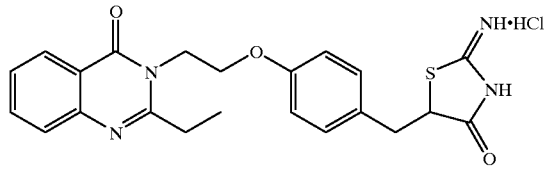

The title compound (329 mg, 78%) was prepared from ethyl 2-bromo-3-[4-[2-[2-ethyl-4-oxo-3,4-dihydro-3-quinazolinyl]ethoxy]phenyl]propanoate (473 mg, 1.0 mmol) (obtained from preparation 25), sodium acetate (164 mg, 2.0 mmol) and thiourea (152 mg, 2.0 mmol) by a similar procedure to that described in preparation 26.

$^1$H NMR (CDCl$_3$): δ8.12 (d, J=7.88 Hz, 1H), 7.80 (t, J=7.03 Hz, 1H), 7.62 (d, J=7.88 Hz, 1H), 7.49 (t, J=7.03 Hz, 1H), 7.12 (d, J=7.58 Hz, 2H), 6.84 (d, J=7.58 Hz, 2H), 4.50 (dd, J=9.43, 3.72 Hz, 1H), 4.46 (t, J=5.31 Hz, 2H), 4.25 (d, J=5.31 Hz, 2H), 3.25 (dd, J=14.11, 3.72 Hz, 1H), 3.04 (q, J=7.17 Hz, 2H), 2.81 (dd, J=14.11, 9.43 Hz, 1H), 1.31 (t, J=7.19 Hz, 3H).

Preparation 28

3-[4-[2-[2-Ethyl-4-methyl-6-oxo-1,6-dihydro-1-pyrimidinyl]ethoxy]phenyl]-2-hydroxypropanoic Acid

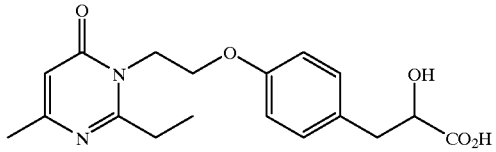

A mixture of ethyl 2-bromo-[3-[4-[2-[2-ethyl-4-methyl-6-oxo-1,6-dihydro-1-pyrimidinyl-ethoxy]phenyl]propanoate (438 mg, 1.0 mmol) (obtained from preparation 24), sodium hydroxide (44 mg, 1.1 mmol) and calcium carbonate (100 mg, 1.0 mmol) in 1,6-dioxane (2 ml) and water (3 ml) was refluxed for 10 h. The reaction mixture was cooled to room temperature and acidified to pH 4 with 2N HCl and extracted with EtOAc (2×10 ml). The combined organic layers were washed with brine, dried over Na$_2$SO$_4$ and concentrated to afford the title compound (92 mg, 27%).

$^1$H NMR (CDCl$_3$+DMSO-d$_6$): δ7.12 (d, J=8.61 Hz, 2H), 6.78 (d, J=8.61 Hz, 2H), 6.19 (s, 1H), 4.50–4.32 (m, 2H), 4.30–4.05 (m, 3H), 3.10–2.60 (m, 4H), 2.25 (s, 3H), 1.30 (t, J=7.20 Hz, 3H).

Preparation 29

Ethyl 3-[4-[2-[2-ethyl-4-methyl-6-oxo-1,6-dihydro-1-pyrimidinyl]ethoxy]phenyl]-2-hydroxypropanoate

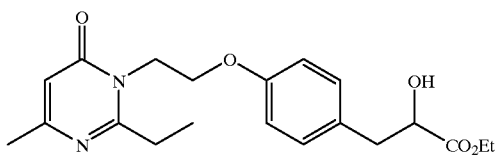

Method A

A solution of 3-[4-[2-[2-ethyl-4-methyl-6-oxo-1,6-dihydro 1-pyrimidinyl]ethoxy]phenyl]-2-hydroxypropanoic acid (346 mg, 1.0 mmol) (obtained from preparation 28) in ethanol (3 ml) containing concentrated hydrochloric acid (0.1 ml) was refluxed for 10 h. The solution was cooled to room temperature, diluted with water and extracted with EtOAc (2×10 ml). The combined organic extracts were washed with brine, dried over anhydrous Na$_2$SO$_4$ and concentrated to yield the title compound (97 mg, 26%).

Method B

A mixture of ethyl 2-bromo-3-[4-[2-[2-ethyl-4-methyl-6-oxo-1,6-dihydro-1-pyrimidinyl]ethoxy]phenyl]propanoate (1.0 g, 2.28 mmol) (obtained from preparation 24) formamide (225 μl) and water (45 μl, 45 mg, 2.5 mmol) was heated at 160° C. for 3 h. Water (45 μl) was added further and stirred for 2 h at 175° C. The reaction mixture was cooled to room temperature, diluted with EtOAc (10 ml) washed with brine, dried over anhydrous Na$_2$SO$_4$ and concentrated to yield the crude compound which was purified by flash chromatography to afford the title compound (306 mg, 36%).

$^1$H NMR (CDCl$_3$): δ7.11 (d, J=8.62 Hz, 2H), 6.77 (d, J=8.62 Hz, 2H), 6.18 (s, 1H), 4.50–4.31 (m, 2H), 4.30–4.05 (m, 5H), 3.10–2.80 (in, 4H), 2.25 (s, 3H), 1.40–1.15 (m, 6H).

Preparation 30

5-[4-[2-[2-Ethyl-4-methyl-6-oxo-1,6-dihydro-1-pyrimidinyl]ethoxy]phenyl Methylene]-2-thio-1,3-oxazolidine-4-one

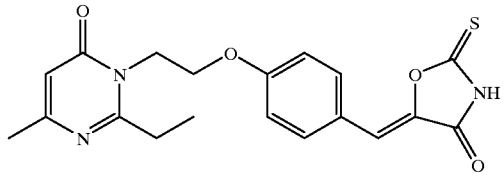

An inmate mixture of 4-[2-[2-ethyl-4-methyl-6-oxo-1,6-dihydro-1-pyrimidinyl]ethoxy]benzaldehyde (286 mg, 1.0 mmol) (obtained from preparation 3), 2-thio-1,3-oxazolidine-4-one (175 mg, 1.5 mmol) and anhydrous sodium acetate (246 mg, 3.0 mmol) was heated at 120° C. under reduced pressure (2.0 torr.) for 90 min. After cooling, the reaction mixture was poured into ethyl acetate (80 ml) and water (20 ml) and stirred for 30 min, the aqueous layer was separated and acidified to pH 4 with 2N HCl. The solid separated was filtered and dried to yield the title compound (207 mg, 54%).

$^1$H NMR (CDCl$_3$): δ7.76 (d, J=8.62 Hz, 2H), 6.93 (d, J=8.62 Hz, 2H), 6.59 (s, 1H), 6.17 (s, 1H), 4.50–4.30 (i, 4H), 2.98 (q, J=7.47 Hz, 2H), 2.27 (s, 3H), 1.35 (t, J=7.47 Hz, 3H).

Preparation 31

4-[2-[2,5,6-Trimethyl-4-oxo-3,4-dihydro-thieno-[2,3-d]pyrimidin-3yl]ethoxy]benzaldehyde

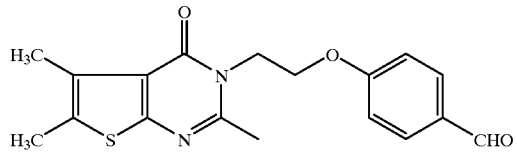

The title compound (5.04 g, 27%) was prepared from 2,5,6-trimethyl-4-oxo-thienopyrimidine (10.59 g, 54.6 mmol), 4-[2-bromoethoxy]benzaldehyde (12.82 g, 56 mmol) and K$_2$CO$_3$ (15.04 g, 109 mmol) as base by a similar procedure to that described in preparation 1.

$^1$H NMR (CDCl$_3$): δ 9.88 (s, 1H), 7.82 (d, J=8.72 Hz, 2H), 6.98 (d, J=8.72 Hz, 2H), 4.60–4.30 (m, 4H), 2.78 (s, 3H), 2.46 (s, 3H), 2.37 (s, 3H).

Preparation 32

4-[2-[2-Methyl-4-oxo-3,4-dihydro-3-quinazolinyl]ethoxy]nitrobenzene

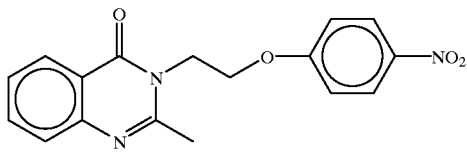

The title compound (1.2 g, 60%) was prepared from 2-methyl-4-oxo-3,4-dihydroquinazoline (1.0 g, 6.25 mmol) and 4-[2-bromoethoxy]nitrobenzene (1.69 g, 6.9 mmol) and K$_2$CO$_3$ (1.73 g, 12.5 mmol) as a base by a similar procedure to that described in preparation 1.

$^1$ NMR (CDCl$_3$): 8.24 (d, J=7.5 Hz, 1H), 8.18 (d, J=9.22 Hz, 2H), 7.75 (t, J=7.50 Hz, 1H), 7.63 (d, J=7.50 Hz, 1H), 7.46 (t, J=7.50, 1H), 6.94 (d, J=9.22 Hz, 2H), 4.58 (t, J=4.98 Hz, 2H), 4.46 (t, J=4.98 Hz, 2H), 2.82 (s, 3H).

Preparation 33

4-[2-[2-Methyl-4-oxo-3,4-dihydro-3-quinazolinyl]ethoxy]aniline

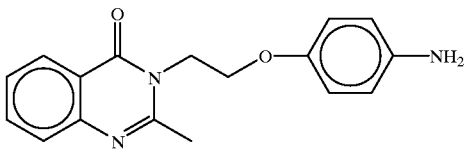

The title compound (9.07 mg, 99%) was prepared from 4-[2-[2-methyl-4-oxo-3,4-dihydro-3-quinazolinyl]ethoxy]nitrobenzene (1.0 g, 3.1 mmol) (obtained from preparation 32) by a similar procedure to that described in preparation 22.

$^1$H NMR (CDCl$_3$) δ: 8.24 (d, =7.50 Hz, 1H), 7.69 (t, J=4.13 Hz, 1H), 7.62 (d, J=7.50 Hz, 1H), 7.43 (t, J=7.50 Hz, 1H), 6.64 (d, J=8.8 Hz, 2H), 6.60 (d, J=8.80 Hz, 2H), 4.49 (t, J=4.98 Hz, 2H), 4.26 (t, J=4.98 Hz, 2H), 2.81 (s, 3H).

Preparation 34

Ethyl 2-Bromo-3-[4-[2-[2-methyl-4-oxo-3,4-dihydro-3-quinazolinyl]ethoxy]phenyl]propanoate

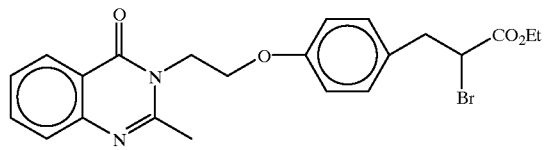

The title compound (3.4 g, 58%) was prepared from 4-[2-[2-methyl-4-oxo-3,4-dihydro-3-quinazolinyl]ethoxy]aniline (3.75 g, 12.7 mmol) (obtained from preparation 33, NaNO$_2$ (955 mg, 13.8 mmol) and ethyl acrylate (8.2 mL, 7.62 g, 76.2 mmol) by a similar procedure to that described in preparation 24.

$^1$H NMR (CDCl$_3$): δ8.23 (d, J=7.50 Hz, 1H), 7.80–7.60 (m, 2H), 7.43 (t, J=7.50 Hz, 1H), 7.31 (d, J=7.50 Hz, 1H), 7.10 (d, J=7.50 Hz, 1H), 6.85–6.70 (m, 2H), 4.53 (t, J=4.98 Hz, 2H), 4.33 (t, J=4.98 Hz, 2H), 4.31 (dd, J=8.71, 3.83 Hz, 1H), 4.12 (q, J=5.80 Hz, 2H), 3.35 (dd, J=14.12, 8.71 Hz, 1H), 3.13 (dd, J=14.12, 3.83 Hz, 1H), 2.80 (s, 3H), 1.22 (t, J=5.8 Hz, 3H).

Preparation 35

5-[4-[2-[2-Methyl-4-oxo-3,4-dihydro-3-quinazolinyl]ethoxy]phenyl Methyl]-2imino thiazolidine-4-one Hydrochloride

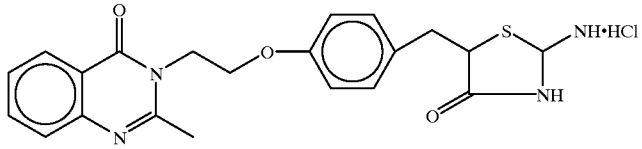

The title compound (1.8 g, 60%) was obtained from ethyl 2-bromo-3-[4-[2-[2-methyl-4-oxo-3,4-dihydro-3-quinazolinyl]ethoxy]phenyl propanoate [3,4 g, 7.4 mmol) (obtained from preparation 34), sodium acetate (2.0 g, 14.8 mmol) and thiourea (1.13 g, 14.8 mmol) by a similar procedure to that described in preparation 26.

$^1$H NMR (CDCl$_3$) δ: 8.79 (bs, 1H, D$_2$O exchangeable), 8.11 (d, J=7.50 Hz, 1H), 7.80 (t, J 7.50 Hz, 1H), 7.59 (d, J=7.50 Hz, 1H), 7.48 (t, J=7.50 Hz, 1H), 7.12 (d, J=8.48 Hz, 2H), 6.86 (d, J=8.48 Hz, 2H), 4.51 (dd, J=9.54, 3.91 Hz, 1H), 4.44 (t, J=4.98 Hz, 2H), 4.26 (t, J 4.98 Hz, 2H), 3.22 (dd, J=14.11, 3.91 Hz, 1H), 2.82 (dd, J=14.11, 9.54 Hz, 1H), 2.71 (s, 3H).

Preparation 36

4-[2-[2-Ethyl-4-trifluoromethyl-6-oxo-1,6-dihydro-1-pyrimidinyl]ethoxy]benzaldehyde

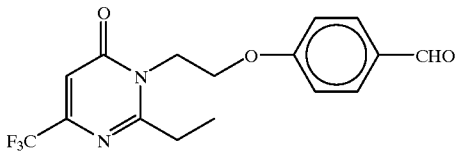

The title compound (138 mg, 40%) was prepared from 2-ethyl-4-trifluoromethyl-(1,6-dihydro-6-pyrimidone (200 mg, 1.04 mmol) and 4-[2-bromoethoxy]benzaldehyde (238.5 mg, 1.04 mmol) in presence of K$_2$C$_{O3}$ (287.5 mg, 2.08 mmol) as base by a similar procedure to that described in preparation 1.

$^1$H NMR (CDCl$_3$): δ9.89 (s, 1H), 7.83 (d, J=8.67 Hz, 2H), 6.95 (d, J=8.67 Hz, 2H), 6.70 (s, 1H), 4.50 (t, J=4.66 Hz, 2H), 4.39 (t, J=4.66 Hz, 21), 3.1 (q, J=7.4 Hz, 2H), 1.4 (t, J=7.4 Hz, 3H).

Preparation 37

Ethyl [4-[[2,4-dioxo-1,3-thiazolidine-5yl]methyl] phenoxy]acetate

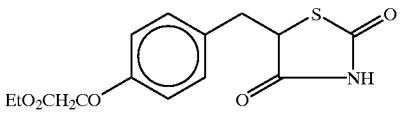

Method A

A solution of ethyl [4-[[2,4-dioxo-1,3-thiazolidine-5-yl]methylene]phenoxy]acetate (10 g) in 1,4-dioxane (200 mL) was reduced with hydrogen in the presence of 5% palladium on charcoal (15 g) at 40 psi pressure for 24 h. The mixture was filtered through a bed of celite. The filtrate was evaporated to dryness under reduced pressure to afford the title compound (9.5 g, 95%).

Method B

To magnesium turnings (6.6 g, 0.277 mol) in methanol (150 mL) was added a solution of ethyl [4-[[2,4--dioxo-1,3-thiazolidine-5-yl]methylene]phenoxy]acetate (5 g, 16.3 mmol) in methanol (50 mL) and stirred for 12 h, maintaining the temperature below 50° C., when the reaction initiates as evidenced by hydrogen evolution and heat generation. The reaction mixture was poured into iced water (150 mL), neutralised with 10% aqueous hydrochloric acid, and the solution was extracted with ethyl acetate (3×100 mL). The combined organic extracts were washed with water (150 mL) brine (100 mL) and dried (MgSO$_4$), and the solvent was removed under reduced pressure. The residue was chromatographed on silica gel in 2% methanol in dichloromethane to give the title compound (2.3 g, 46%. mp: 107° C.

$^1$H NMR (CDCl$_3$): δ8.5 (bs, 1H, D$_2$O exchangeable), 7.20 (d, J=8.50 Hz, 2H), 7.06 (d, J=8.50 Hz, 2H), 4.65 (s, 2H), 4.53 (dd, J=9.39, 3.74 Hz, 1H), 4.32 (q, J=7.20 Hz, 2H), 3.50 (dd, J=14.12, 3.74 Hz, 1H), 3.14 (dd, J=14.12, 9.39 Hz, 1H), 1.34 (t, J=7.17 Hz, 3H).

Preparation 38

[4-[[2,4-Dioxo-1,3-thiazolidine-5yl]methyl] phenoxy]acetic Acid

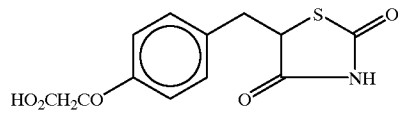

To a stirred solution of ethyl [4-[[2,4-dioxo-1,3-thiazolidine-5-yl]methyl]phenoxy]acetate (110 g, 0.36 mol) in methanol (0.65 L) was added as solution of Na$_2$CO$_3$ (200 g, 1.88 mol) in water (0.65 L) and stirred for 5 h at 25 to 30° C. After completion of the reaction, methanol was removed under reduced pressure; water was added to the residue and was acidified with hydrochlori acid. The precipitated white solid was filtered and dired to yield the title compound (80 g, 80%). mp: 181–183° C.

1H NMR (DMSO-d$_6$): δ12.40 (bs, 1H, D$_2$O exchangeable), 8.60 (bs, 1H, D$_2$O exchangeable)., 7.16 (d, J=8.40 Hz, 2H), 6.50 (d, J=8.40 Hz, 2H), 4.87 (dd, J=9.14, 4.20 Hz, 1H), 4.65 (s, 2H), 3.32 (dd, J=14.12, 4.20 Hz, 1H), 3.05 (dd, J=14.12, 9.14 Hz, 1H).

Preparation 39

5-[[4-[N-[Methyl Benzamide-2-yl]aminocarbonyl]methoxy]phenyl Methyl]thiazolidine-2,4-dione

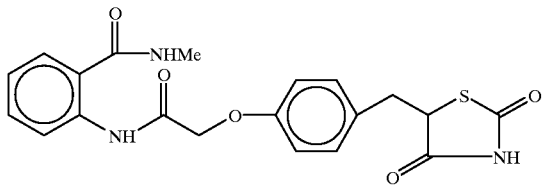

Method A

To a stirred solution of 14-[[2,4-dioxo-1,3-thiazolidine-5-yl]methyl]phenoxy]acetic acid (1.9 g, 6.75 mmol) in dichloromethane (15 mL) was added triethyl amine (1.876 mL, 1.36 g, 13.48 mmol) followed by pivaloyl chloride (0.913 mL, 899 mg, 5.46 mmol) at 0° C. and was furthe stirred for 1 h at 0° C. The reaction mixture was added to a solution of 2-amino-N-methyl benzamide (920 mg, 6.13 mmol) in acetic acid (10 mL) and xylene (10 mL) and the reaction mixture was stirred for 30 min at 250C. The solvents were removed under reduced pressure and the product was purified to yield the title compound (2.51 g, 91%). mp =201–203° C.

Method B

To a stirred solution of [4-[[2,4-dioxo-1,3-thiazolidine-5-yl]methyl]phenoxy]acetic acid (1.9 g, 6.75 mmol) in xylene (15 mL) was added thionyl chloride (2.46 mL, 4.02 g, 33.75 mmol) and refluxed for 1 h. The reaction mixture was cooled to room temperature and excess thionyl chloride was removed under reduced pressure. The residue was added to a solution of 2-amino-N-methyl benzamide (920 mg, 6.13 mmol) in acetic acid (10 mL) and xylene (10 mL) and stirred for 1 h at 25° C. The solvents were removed under reduced pressure and the product was purified to yield the title compound (2.4 g, 86%).

$^1$H NMR (CDCl$_3$, 200 MHz) δ: 12.21 (s, 1H, D$_2$O exchangeable), 11.7 (bs, 1H, D$_2$O exchangeable), 8.63 (d, J=8.30 Hz, 1H), 7.96 (bs, 1H, D$_2$O exchangeable), 7.65 (d, J=7.80 Hz, 1H), 7.47 (t, J=7.80 Hz, 1H), 7.30–6.96 (m, 5H), 4.60 (s, 2H), 4.48 (dd, J=9.6, 3.70 Hz, 1H), 3.45 (dd, J=13.70, 3.70 Hz, 1H), 3.05 (dd, J=13.70, 9.60 Hz, 1H), 2.94 (d, J=3.74 Hz, 3H).

EXAMPLE 1

5-[4-[2-[1Methyl-2-propyl-6-oxo-1,6-dihydro-1-pyrimidinyl]ethoxy]phenyl Methylene]thiazolidine-2,4-dione

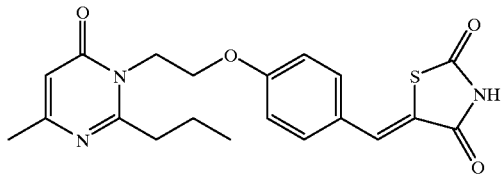

A mixture of 4-[2-[4-methyl-2-propyl-6-oxo-1,6-dihydro-1-pyrimidinyl]ethoxy]benzaldehyde (10 g, 24.5 mmol) (obtained from preparation 1), thiazolidine-2,4-dione (3,5 g, 30 mmol), benzoic acid (388 mg, 3.18 mmol) and piperidine (352 μl, 303 mg, 3.68 mmol) in toluene (50 ml) was refluxed for 1 h with continuous removal of water. The reaction mixture was cooled to room temperature and the resultant crystalline compound was filtered and washed with water and dried to afford the title compound (12.3 g, 99%), mp 240–242° C.

$^1$H NMR (DMSO-d$_6$): δ12.40 (bs, 1H, D$_2$O exchangeable), 7.75 (s, 1H), 7.54 (d, J=8.72 Hz, 2H), 7.02 (d, J=8.72 Hz, 2H), 6.15 (s, 1H), 4.45–4.15 (m, 4H), 2.91 (t, J=7.65 Hz, 2H), 2.20 (s, 3H), 1.90–1.65 (m, 2H), 1.06 (t, J 7.65 Hz, 3H).

EXAMPLE 2

5-[4-[2-[2,4-Dimethyl-6-oxo-1,6-dihydro-1-pyrimidinyl]ethoxy]phenyl Methylene]thiazolidine-2,4-dione

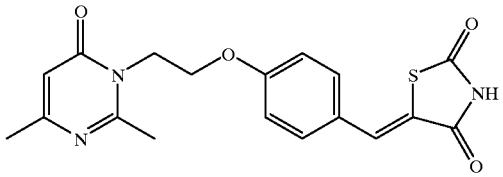

The title compound (0.98 g, 95%) was obtained from 4-[2-[2,4-dimethyl-6-oxo-1,6-dihydro-1-pyrimidinyl]ethoxy]benzaldehyde (0.8 g, 2.8 mmol) (obtained from preparation 2) and thiazolidine-2,4-dione (0.344 g, 2.8 mmol) by a similar procedure to that described in example 1, mp 235° C.

$^1$H NMR (CDCl$_3$): δ8.50 (bs, 1H, D$_2$O exchangeable), 7.80 (s, 1H), 7.48 (d, J=8.40 Hz, 2H), 6.98 (d, J=8.40 Hz, 2H), 6.21 (s, 1H), 4.52–4.30 (m, 4H), 2.70 (s, 3H), 2.25 (s, 3H).

EXAMPLE 3

5-[4-[2-[2-Ethyl-4-methyl-6-oxo-1,6-dihydro-1-pyrimidinyl]ethoxy]phenyl Methylene]thiazolidine-2,4-dione

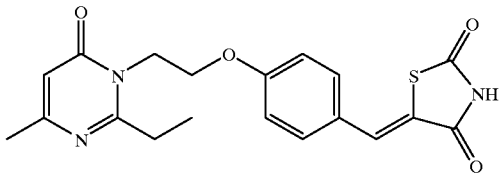

The title compound (2.13 g, 92%) was obtained from 4-[2-[2-ethyl-4-methyl-6-oxo-1,6-dihydro-1-pyrimidinyl]ethoxy]benzaldehyde (1.7 g, 5.94 mmol) (obtained from preparation 3) and thiazolidine-2,4-dione (0.695 g, 5.94 mmol) by a similar procedure to that described in example 1, mp248–250° C.

$^1$H NMR (CDCl$_3$+DMSO-d$_6$): δ12.25 (bs, 1H, D$_2$O exchangeable), 7.78 (s, 1H), 7.40 (d, J=7.40 Hz, 2), 7.0 (d, J=7.40 Hz, 2H), 6.20 (s, 1H), 4.48–4.24 (m, 4H), 3.0 (q, J=6.4 Hz, 2H), 2.20 (s, 3H), 1.28 (t, J=6.4 Hz, 3H).

EXAMPLE 4

5-[4-[2-[2-Butyl-4-methyl-6-oxo-1,6-dihydro-1-pyrimidinyl]ethoxy]phenyl Methylene]thiazolidine-2,4-dione

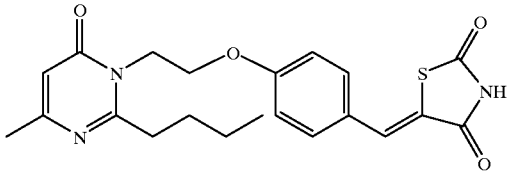

The title compound (1.2 g, 83%) was obtained from 4-[2-[2-butyl-4-methyl-6-oxo-1,6 dihydro-1-pyrimidinyl]ethoxy]benzaldehyde (1.1 g, 3,5 mmol) (obtained from preparation 4) and thiazolidine-2,4-dione (410 mg, 3,5 mmol) by a similar procedure to that described in example 1, mp 209° C.

$^1$H NMR (CDCl$_3$): δ7.80 (s, 1H), 7.40 (d, J=8.63 Hz, 2H), 6.95 (d, J=8.63 Hz, 2H), 6.21 (s, 1H), 4.55–4.22 (m, 4H), 2.95 (t, J=7.47 Hz, 2H), 2.25 (s, 3H), 1.85–1.60 (m, 2H), 1.60–1.40) (m, 2H), 0.99 (t, J=7.10 Hz, 3H).

EXAMPLE 5

5-[4-[2-[2-Benzyl-4-methyl-6-oxo-1,6-dihydro-1-pyrimidinyl]ethoxy]phenyl Methylene]thiazolidine-2,4-dione

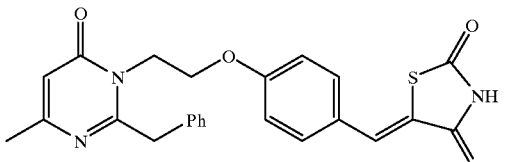

The title compound (1.70 g, 66%) was obtained from 4-[2-[2-benzyl-4-methyl-6-oxo-1,6-dihydro-1-pyrimidinyl]ethoxy]benzaldehyde (2.0 g, 5.74 mmol) (obtained from preparation 5) and thiazolidine-2,4-dione (0.74 g, 6.4 mmol) by a similar procedure to that described in example 1, mp 223° C.

$^1$H NMR (CDCl$_3$+DMSO-d$_6$): δ7.74 (s, 1H), 7.44 (d, J=8.71 Hz, 2H), 7.40–7.10 (m, 5H), 6.95 (d, J=8.71 Hz, 2H), 6.26 (s, 1H), 4.38 (s, 2H), 4.35–4.10 (m, 4H), 2.32 (s, 3H).

EXAMPLE 6

5-[4-[2-2,5-Diethyl-4-methyl-6-oxo-1,6-dihydro-1-pyrimidinyl]ethoxy]phenyl Methylene]thiazolidine2,4-dione

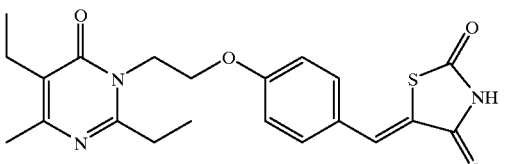

The title compound (881 mg, 92%) was obtained from 4-[2-[2,5-diethyl-4-methyl-6-oxo-1,6-dihydro-1-pyrimidinyl]ethoxy]benzaldehyde (730 mg, 2.32 mmol) (obtained from preparation 6) and thiazolidine-2,4-dione (451 mg, 2.55 mmol) by a similar procedure to that described in example 1, mp 252–254° C.

$^1$H NMR (CDCl$_3$+DMSO-d$_6$): δ12.08 (bs, 1H, D$_2$O exchangeable), 7.69 (s, 1H), 7.44 (d, J=8.58 Hz, 2H), 6.97 (d, J=8.58 Hz, 2H), 4.50–4.20 (m, 4H), 2.93 (q, J=7.43 Hz, 2H), 2.50 (q, J=7.43 Hz, 2H), 2.26 (s, 3H), 1.33 (t, J=7.43 Hz, 3H), 1.07 (t, J=7.43 Hz, 3H).

EXAMPLE 7

5-[4-[2-[2-Ethyl-4-phenyl-6-oxo-1,6-dihydro-1-pyrimidinyl]ethoxy]phenyl Methylene]thiazolidine-2,4-dione

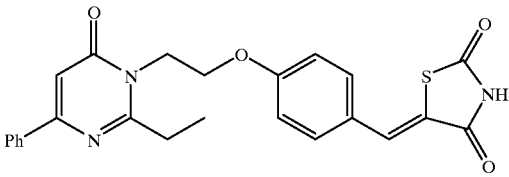

The title compound (2.2 g, 88%) was obtained from 4-[2-[2-ethyl-4phenyl-6-oxo-1-dihydro-1-pyrimidinyl]ethoxy]benzaldehyde (2.09 g, 6.0 mmol) (obtained from preparation 7) and thiazolidine-2,4-dione (0.702 g, 6.0 mmol) by a similar procedure to that described in example 1, mp 234° C.

$^1$H NMR (DMSO-d$_6$): 12.58 (bs, 1H, D$_2$O exchangeable), 8.22–8.05 (m, 2H), 7.74 (s, 1H), 7.66–7.38 (m, 5H), 7.11 (d, J=8.30 Hz, 2H), 6..92 (s, 1H), 4.48–4.20 (m, 4H), 3.06 (q, J=7.06 Hz, 2H), 1.35 (t, J=7.06 Hz, 3H).

EXAMPLE 8

5-[4-[2-[4-Oxo-3,4-dihydro-3-quinazolinyl]ethoxy]phenyl Methylene]thiazolidine-2,4-dione

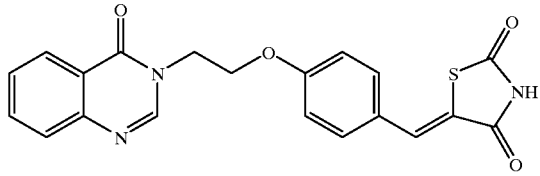

The title compound (1.91 g, 84%) was obtained from 4-[2-4-oxo-3,4-dihydro-3-quinazolinyl]ethoxy]benzaldehyde (1.7 g, 5.78 mmol) (obtained from preparation 9) and thiazolidine-2,4-dione (678 mg, 5.79 mmol) by a similar procedure to that described in example 1, mp 242–244° C.

$^1$H NMR (CDCl$_3$+DMSO-d$_6$): δ12.56 (bs, 1H, D$_2$O exchangeable), 8.42 (s, 1H), 8.18 (d, J=7.89 Hz, 1H), 7.84 (t, J=7.47 Hz, 1H), 7.72 (s, 1H), 7.72–7.50 (m, 2H), 7.54 (d, J=8.72 Hz, 2H), 7.11 (d, J=8.72 Hz, 2H), 4.40 (s, 4H).

EXAMPLE 9

5-[4-[2-[2-Methyl-4-oxo-3,4-dihydro-3-quinazolinyl]ethoxy]phenyl Methylene]thiazolidine-2,4-dione

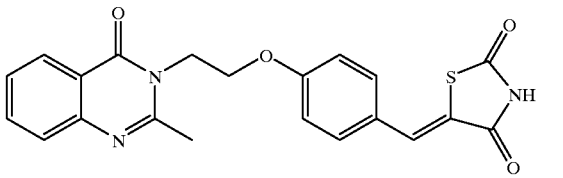

The title compound (4.28, 93%) was obtained from 4-[2-[2-methyl-4-oxo-3,4-dihydro-3-quinazolinyl]ethoxy]benzaldehyde (3,4 g, 11.04 mmol) (obtained from preparation 10) and thiazolidine-2,4-dione (1,6 g, 13.8 mmol) by a similar procedure to that described in example 1, mp 278° C.

$^1$H NMR (DMSO-$d_6$): δ12.58 (bs, 1H, $D_2O$ exchangeable), 8.19 (d, J=8.0 Hz, 1H), 7.89–7.44 (m, 6H), 7.03 (d, J=8.7 Hz, 2H), 4.58–4.42 (m, 2H), 4.42–4.25 (m, 2H), 2.81 (s, 3H).

EXAMPLE 10

5-[4-[2-[2-Ethyl-4-oxo-3,4-dihydro-3-quinazolinyl]ethoxy]phenyl Methylene]thiazolidine 2,4-dione

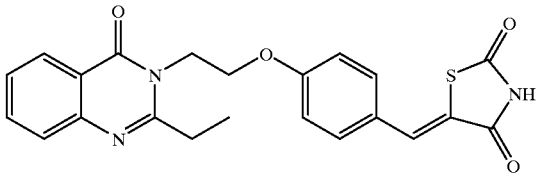

The title compound (0.42 g, 92%) was obtained from 4-[2-[2-ethyl-4-oxo3,4-dihydro-3-quinazolinyl]ethoxy]benzaldehyde (0.35 g, 1.08 mmol) (obtained from preparation 11) and thiazolidine-2,4-dione (0.16 g, 1.4 mmol) by a similar procedure to that described in example 1, mp 257° C.

$^1$H NMR (DMSO-$d_6$): δ12.58 (bs, 1H, $D_2O$ exchangeable), 8.15 (d, J=8.0 Hz, 1H), 7.82–7.44 (m, 6H), 7.08 (d, =8.0 Hz, 2H), 4.47–4.40 (,2H), 4.40–4.30 (m, 2H), 3.08 (q, J=7.0 Hz, 2H), 1.37 (t, J=7.0 Hz, 3H).

EXAMPLE 11

5-[4-2-[8-Aza-2-methyl-4-oxo-3,4-dihydro-3-quinazolinyl]ethoxy]phenyl Methylene]thiazolidine2,4-dione

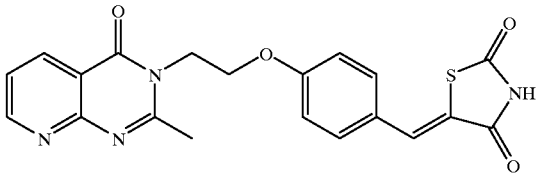

The title compound (0.25 g, 68%) was obtained from 4-[2-[8-Aza-2-methyl-4-oxo-3,4-dihydro-3-quinazolinyl]ethoxy]benzaldehyde (0.28 g, 0.9 mmol) (obtained from preparation 12) and thiazolidine-2,4-dione (0.106 g, 0.9 mmol) by a similar procedure to that described in example 1, mp 276° C.

$^1$H NMR (CDCl$_3$+DMSO-$d_6$): δ9.00–8.90 (m, 1H), 8.51 (d, J=7.30 Hz, 1H), 7.72 (s, 1H), 7.51 (d, J=8.72 Hz, 2H), 7.55–7.45 (m, 1H), 7.05 (d, J=8.72 Hz, 2H), 4.60–4.50 (m, 2H), 4.50–4.38 (m, 2H), 2.85 (s, 3H).

EXAMPLE 12

5-[4-[[3-Methyl-4-oxo-3,4-dihydro-2-quinazolinyl]methoxy]phenyl Methylene]thiazolidine-2,4-dione

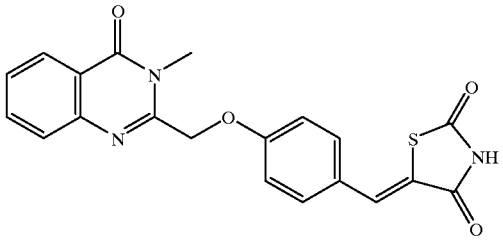

The title compound (11.10 g, 96%) was obtained from 4-[[3-methyl-4-oxo3,4-dihydro-2-quinazolinyl]methoxy]benzaldehyde (9.0 g, 30.61 mmol) (obtained from preparation 13) and thiazolidine-2,4-dione (3.6 g, 30.61 mmol) by a similar procedure to that described in example 1, mp 280° C.

$^1$H NMR (CDCl$_3$+DMSO-$d_6$): δ12.38 (bs, 1H, $D_2O$ exchangeable), 8.19 (d, J=7.47 Hz, 1H), 7.82–7.60 (m, 2H), 7.72 (s, 1H), 7.53 (d, J=8.7 Hz, 2H), 7.60–7.48 (m, 1H), 7.23 (d, J=8.72 Hz, 2H), 5.35 (s, 2H), 3.68 (s, 3H).

EXAMPLE 13

5-[4-[[3-Ethyl-4-oxo-3,4-dihydro-2-quinazolinyl]methoxy]phenyl Methylene]thiazolidine-2,4-dione

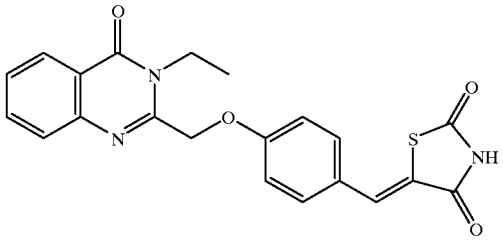

The title compound (3.3 g, 83%) was obtained from 4-[[3-ethyl-4-oxo-3,4-dihydro-2-quinazolinyl]methoxy]benzaldehyde (3.0 g, 9.74 mmol) (obtained from preparation 14) and thiazolidine-2,4-dione (1.14 g, 9.74 mmol) by a similar procedure to that described in example 1, mp 260–261° C.

$^1$H NMR (CDCl$_3$+DMSO-$d_6$): δ12.58 (bs, 1H, $D_2O$ exchangeable), 8.18 (d, J=7.88 Hz, 1H), 7.92–7.74 (m, 1H), 7.78 (s, 1H), 7.74–7.54 (m, 2H), 7.61 (d, J=8.72 Hz, 2H), 7.29 (d, J=8.72 Hz, 2H), 5.40 (s, 2H), 4.14 (q, J=6.84 Hz, 2H), 1.34 (t, J=6.84 Hz, 3H).

EXAMPLE 14

5-[4-[[1-Methyl-4-oxo-1,4-dihydro-2-quinazolinyl]methoxy]phenyl Methylene]thiazolidine-2,4-dione

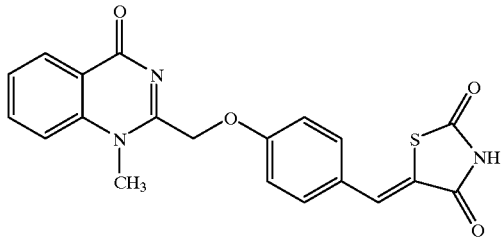

The title compound (310 mg, 79%) was obtained from 4-[[1-methyl-4-oxo-1,4-dihydro-2-quinazolinyl]methoxy]benzaldehyde (294 mg, 1.0 mmol) (obtained from preparation 15) and thiazolidine-2,4-dione (117 mg, 1.0 mmol) by a similar procedure to that described in example 1.

$^1$H NMR (DMSO-$d_6$): δ8.09 (d, J=7.88 Hz, 1H), 8.00–7.04 (m, 4H), 7.58 (d, J 8.72 Hz, 2H), 7.24 (d, J=8.72 Hz, 2H), 5.41 (s, 2H), 3.86 (s, 3H).

EXAMPLE 15

5-[3-Methoxy-4-[[3-methyl-4-oxo-3,4-dihydro-2-quinazolinyl]methoxy]phenyl Methylene] thiazolidine-2,4-dione

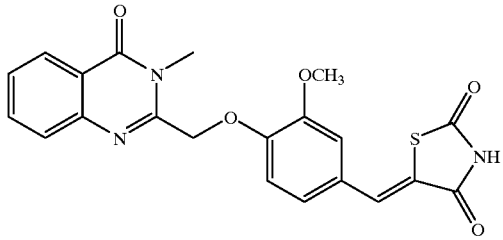

The title compound (235 mg, 90%) was obtained from 3-methoxy-4-[[3-methyl-4-oxo-3,4-dihydroquinazolinyl]methoxy]benzaldehyde (200 mg, 0.62 mmol) (obtained from preparation 16) and thiazolidine-2,4-dione (79 mg, 0.68 mmol) by a similar procedure to that described in example 1, mp 244–246° C.

$^1$H NMR (DMSO-$d_6$+CDCl$_3$) δ12.25 (bs, 1H, D$_2$O exchangeable) 8.02 (d, J=7.20 Hz, 1H), 7.82–7.60 (m, 2H), 7.66 (s, 1H), 7.51 (t, J=7.20 Hz, 1H), 7.38–7.03 (m, 3H), 5.52 (s, 2H), 3.91 (s, 3H), 3.68 (s, 3H).

EXAMPLE 16

5-[4-[2-[4-Acetylamino-2-oxo-1,2-dihydro-1-pyrimidinyl]ethoxy]phenyl Methylene]thiazolidine-2,4-dione

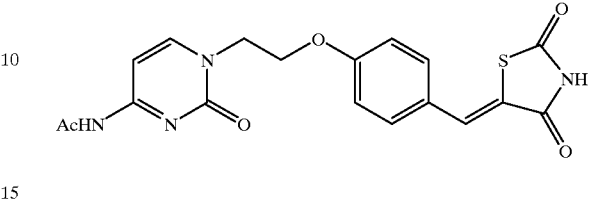

The title compound (1.8 g, 81%) was obtained from 4-[2-[4-acetylamino-2-oxo-1,2-dihydro-1-pyrimidinyl]ethoxy]benzaldehyde (1.7 g, 5.65 mmol) (obtained from preparation 8) and thiazolidine-2,4-dione (0.661 g, 5.65 mmol) by a similar procedure to that described in example 1, mp 274° C.

$^1$H NMR (CDCl$_3$+DMSO-$d_6$): δ 12.56 (bs, 1H, D$_2$O exchangeable), 10.85 (s, 1H, D$_2$O exchangeable), 8.11 (d, J=7.2 Hz, 1H), 7.74 (s, 1H), 7.55 (d, J=S.30 Hz, 2H), 7.17 (d, J=7.20 Hz, 1H), 7.11 (d, J=8.30 Hz, 2H), 4.40–4.05 (m, 4H), 2.08 (s, 3H).

EXAMPLE 17

5-[4-[2-[4-methyl-2-Propyl-6-oxo-1,6-dihydro-1-pyrimidinyl]ethoxy]phenyl methyl] thiazolidine-2,4-dione

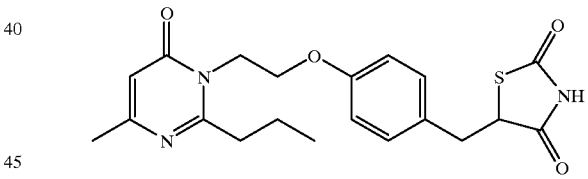

A solution of 5-[4-[2-[4-methyl-2-propyl-6-oxo 1,6-dihydro-1-pyrimidinyl]ethoxy]phenyl methylene] thiazolidine-2,4-dione (5.0 g, 12.46 mmol) obtained from example 1 in 1,4-dioxane (75 ml) was reduced with hydrogen in the presence of 10% palladium on charcoal (12.0 g) at 60 psi pressure for 40 h. The mixture was filtered through a bed of celite. The filtrate was evaporated to dryness under reduced pressure, purified by column chromatography (2:1 EtOAc/petroleum ether as eluent) followed by crystallisation (CH$_2$C$_{12}$) to afford the title compound (4.6 g, 92%), mp 144–146° C.

$^1$H NMR (CDCl$_3$): δ8.25 (bs, 1H, D$_2$O exchangeable) 7.12 (d, J=8.48 Hz, 2H), 6.79 (d, J=7.48 Hz, 2H), 6.21 (s, 1H), 4.47 (dd, J=9.36, 4.06 Hz, 1H), 4.41 (t, J=4.47 Hz, 2H), 4.26 (t, J=4.47 Hz, 2H), 3.41 (dd, J=14.11, 4.06 Hz, 1H), 3.10 (dd, J=14.11 9.36 Hz, 1H), 2.92 (t, J=7.63 Hz, 2H), 2.24 (s, 3H), 1.90–1.60 (m, 2H), 1.05 (t, J=7.65 Hz, 3H).

EXAMPLE 18

5-[4-[2-[2,4-Dimethyl-6-oxo-1,6-dihydro-1-pyrimidinyl]ethoxy]phenyl Methyl]thiazolidine-2,4-dione

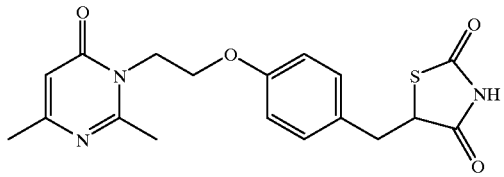

The title compound (850 mg, 85%) was obtained from 5-[[2-[2,4-dimethyl-6-oxo-1,6-dihydro 1-pyrimidinyl] ethoxy]phenyl methylene]thiazolidine-2,4-dione (1.0 g) (obtained from example 2) by a similar procedure to that described in example 17, mp 170° C.

$^1$H NMR (CDCl$_3$): δ8.15 (bs, 1H, D$_2$O exchangeable), 7.14 (d, J=8.30 Hz, 2H), 6.80 (d, J=8.30, 2H), 6.21 (s, 1H), 4.50 (dd, J=9.13, 3.73 Hz, 1H), 4.48–4.20 (n, 4H), 3.41 (dd, J=14.12, 3.73 Hz, 1H), 3.13 (dd, J=14.12, 9.13 Hz, 1H), 2.70 (s, 3H), 2.25 (s, 3H).

EXAMPLE 19

5-[4-[2-[2-Ethyl-4-methyl-6-oxo-1,6-dihydro-1-pyrimidinyl]ethoxy]phenyl Methyl]thiazolidine2,4-dione

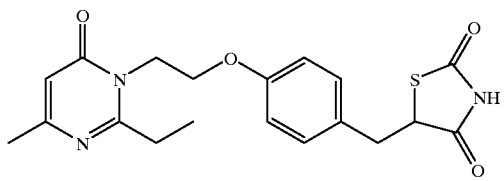

Method A

The title compound (820 mg, 82%) was obtained from 5-[4-[2-[2-ethyl-4-methyl-6-oxo1,6-dihydro-1-pyrimidinyl] ethoxy]phenyl methylene]thiazolidine-2,4-dione (1.0 g, 2.6 mmol) (obtained from example 3) by a similar procedure to that described in example 17.

Method B

To a stirred solution of 5-[4-[2-[2-ethyl-4-methyl-6-oxo-1,6-dihydro1-pyrimidinyl]ethoxy]phenyl methyl]-2-iminothiazolidine-4-one (1.93 g, 5.0 mmol) (obtained from preparation 26) in ethanol (15 ml) was added 2N HCl (10 ml) and refluxed for 12 h. The reaction mixture was cooled to room temperature and ethanol was removed under reduced pressure. The aqueous layer was neutralised with saturated aqueous NaHCO$_3$ solution and extracted with EtOAc (3×20 ml). The combined organic layer was washed with brine, dried over anhydrous Na$_2$SO$_4$ and concentrated to yield the title compound (1.63 g, 84%) which was crystallised from CH$_2$Cl$_2$-pet. ether, mp 148° C. The title compound upon crystallisation from MeOH provided another polymorph, mp 155° C.

$^1$H NMR (CDCl$_3$) δ8.65 (bs, 1H, D$_2$O exchangeable), 7.12 (d, J=8.51 Hz, 2H), 6.79 (d, J=8.51 Hz, 2H), 6.21 (s, 1H), 4.43 (dd, J=9.27, 3.83 Hz, 1H), 4.42 (t, J=4.57 Hz, 2H), 4.26 (t, J=4.57 Hz, 2H), 3.41 (dd, J=14.11, 3.83 Hz, 1H), 3.11 (dd, J=14.11, 9.27 Hz, 1H), 2.99 (q, J=7.47 Hz, 2H), 2.25 (s, 3H), 1.34 (t, J=7.47 Hz, 3H).

EXAMPLE 20

5-[4-[2-[2-Butyl-4-methyl-6-oxo-1,6-dihydro-1-pyrimidinyl]ethoxy] Phenyl Methyl]thiazolidine-2,4-dione

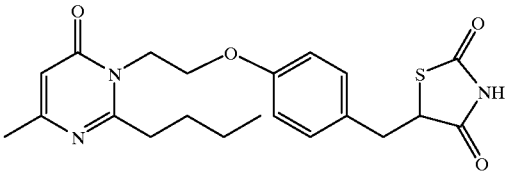

The title compound (780 mg, 78%) was obtained from 5-[4-[2-[2-Butyl-4-methyl-6-oxo-1,6-dihydro-1-pyrimidinyl]ethoxy]phenyl Methylene]thiazolidine-2,4-dione (1.0 g) (obtained from example 4) by a similar procedure to that described in example 17, mp 150–152° C.

$^1$H NMR (CDCl$_3$): δ9.53 (bs, 1H, D$_2$O exchangeable), 7.13 (d, J=8.40 Hz, 2H), 6.79 (d, J=8.40 Hz, 2H), 6.22 (s, 1H), 4.45 (dd, J=9.22, 3.83 Hz, 1H), 4.42 (t, J=4.57 Hz, 2H), 4.26 (t, J=4.57 Hz, 2H), 3.42 (dd, J=14.12, 3.83 Hz, 1H), 3.09 (dd, J=14.12, 9.22 Hz, 1H), 2.95 (t, J=7.47 Hz, 2H), 2.24 (s, 3H), 1.85–1.65 (m, 2H), 1.58–1.32 (m, 2H), 0.98 (t, J=7.38 Hz, 3H).

EXAMPLE 21

5-[4-[2-[2-Ethyl-4-phenyl-6-oxo-1,6-dihydro-1-pyrimidinyl]ethoxy]phenyl Methyl]thiazolidine-2,4-dione

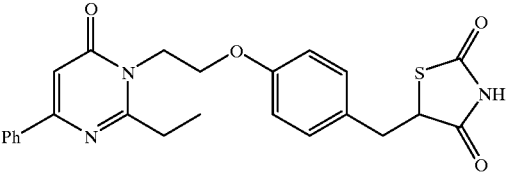

The title compound (300 mg, 50%) was obtained from 5-[4-[2-[2-ethyl-4-phenyl-6-oxo-1,6-dihydro-1-pyrimidinyl]ethoxy]phenyl methylene]thiazolidine-2,4-dione (600 mg, 1.38 mmol) (obtained from example 7) by a similar procedure to that described in example 17, mp 178° C.

$^1$H NMR (CDCl$_3$): δ8.20–7.95 (m, 2H), 7.55–7.35 (m, 3H), 7.12 (d, J=8.30 Hz, 2H), 6.80 (d, J=8.30 Hz, 2H), 6.80 (s, 1H), 4.60–4.40 (m, 3H), 4.40–4.20 (m, 2H), 3.41 (dd, J=14.1, 3.65 Hz, 1H), 3.09 (dd and q overlap, 3H), 1.46 (t, J=7.30 Hz, 3H).

EXAMPLE 22

5-[4-[[3-Methyl-4-oxo-3,4-dihydro-2-quinazolinyl]methoxy]phenyl Methyl]thiazolidine-2,4-dione

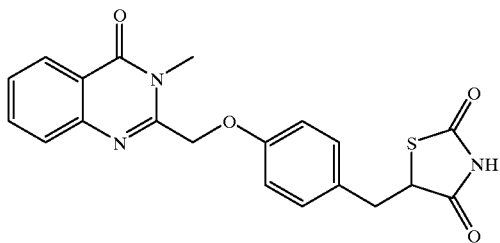

Method A

The title compound (750 mg, 75%) was obtained from 5-[4-[[3-methyl-4-oxo-3,4-dihydro-2-quinazolinyl]methoxy]phenyl methylene]thiazolidine-2,4-dione (1.0 g) (obtained from example 12) by a similar procedure to that described in example 17.

Method B

To a stirred solution of [4-[[2,4-dioxo-1,3-thiazolidine-5-yl]methyl]phenoxy]acetic acid (1.9 g, 6.75 mmol) (obtained form preparation 38) in dichloromethane (15 ml) was added triethyl amine (1.876 ml, 1.36 g, 13.48 mmol) followed by pivaloyl chloride (0.913 ml, 899 mg, 5.46 mmol) at 0° C. and stirring was continued for 1 h at 0° C. The above reaction mixture was added to a solution of 2-amino-N-methyl benzamide (920 mg, 6.13 mmol) in acetic acid (20 ml) and refluxed for 24 h. The reaction mixture was cooled to room temperature and acetic acid was removed under reduced pressure. To the residue water (50 ml) was added and extracted with $CHCl_3$ (3×25 ml). The combined $CHCl_3$ extracts were washed with brine, dried over anhydrous $Na_2SO_4$ and concentrated to yield the title compound (2.16 g, 81%), mp 190° C.

Method C

To a stirred solution of [4-[[2,4-dioxo-1,3-thiazolidine-5-yl]methyl]phenoxy]acetic acid (33 g, 0.117 mol) in dichloromethane (300 mL) was added triethyl amine (35.4 mL, 0.254 mol) followed by pivaloyl chloride (17.3 mL, 0.127 mol) at 0° C. and stirred for 1 h at 0° C. The reaction mixture was added to a solution of 2-amino-N-methyl benzamide (16 g, 0.106 mol) in a mixture of acetic acid (300 mL) and xylene (300 mL) and refluxed for 18 h. The reaction mixture was cooled to room temperature and solvents were removed under reduced pressure. The product was purified to yield the title compound (35.5 g, 85%).

Method D

To a stirred solution of [4-[[2,4-dioxo-1,3-thiazolidine-5-yl]methyl]phenoxy]acetic acid (1.9 g, 6.75 mmol) in dichloromethane (15 mL) was added triethy lamine (1.876 mL, 1.36 g, 13.48 mmol) followed by pivaloyl chloride (0.913 mL, 899 mg, 5.46 mmol) at 0° C. and stirring was continued for 1 h at 0° C. The above reaction mixture was added to a solution of 2-amino-N-methyl benzamide (920 mg, 6.13 mmol) in xylene (20 mL) containing $pTsOH.H_2O$ (646 mg, 3.4 mmol) and refluxed for 24 h. The reaction mixture was cooled to room temperature and xylene was removed under reduced pressure. Water (50 mL) was added to the residue and extracted with $CHCl_3$ (3×25 mL). The combined $CHCl_3$ extracts were washed with brine, dried over anhydrous $Na_2SO_4$ and concentrated to yield the title compound (1.79 g, 58%).

Method E

To a stirred solution of [4-[[2,4-dioxo-1,3-thiazolidine-5-yl]methyl]phenoxy]acetic acid (1.0 g, 3.56 mmol) in xylene (10 mL) was added thionyl chloride (1,6 mL, 2.12 g, 17.8 mmol) and refluxed for 1 h. The reaction mixture was cooled to 25° C. and excess thionyl chloride was removed and then was added to a solution of 2-amino-N-methyl benzamide (534 mg, 3.56 mmol) in a mixture of acetic acid (10 mL) and xylene (5 mL) and refluxed for 20 h. The reaction mixture was cooled to room temperature and the solvents were removed under reduced pressure. To the residue water (20 mL) was added and extracted with $CHCl_3$ (3×25 mL). The combined $CHCl_3$ extracts were washed with brine, dried over anhydrous $Na_2SO_4$ and concentrated to yield the title compound (750 mg, 54%).

Method F

[5-[[4-[N-Methyl benzamide-2-yl]aminocarbonyl]methoxy]phenyl methyl]thiazolidine2,4-dione (1.0 g) (obtained in preparation 39) was heated at 180° C. for 8 h. The reaction mixture was cooled to room temperature diluted with water and extracted with EtOAc (3×20 mL). The combined organic layers were washed with brine, dried over anhydrous $Na_2SO_4$ and concentrated.

Method G

The title compound (345 mg, 34%) was prepared from 5-[4-[[3-methyl-4-oxo-3,4-dihydro-2-quinazolinyl]methoxy]phenyl methylene]thiazolidine-2,4-dione (1.0 g) (obtained from example 12) by a similar procedure to that described in preparation 37, method B.

Polymorphs

Polymorph I

5-[4-[[3-[methyl-4-oxo-3,4-dihydro-2-quinazolinyl]methoxy]phenyl methyl]thiazolidine-2,4-dione (10 g) obtained from any one of the above methods was dissolved in dioxane (200 mL) by warming upto 60° C. The solution was concentrated to 30–50 ml to which methanol was added and stirred for 15–30 min. The white solid precipitated out was filtered and dried to yield the polymorph I, which is having DSC endotherm at 198° C.

Polymorph II

5-[4[-[[3-methyl-4-oxo-3,4-dihydro-2-quinazolinyl]mehoxy]phenyl methyl]thiazolidine-2,4-dione (10 g) obtained from any one of the methods, was dissolved in acetone (300 mL). The solution was concentrated to 30–50 ml and methanol was added. After stirring for 15–30 min, the precipitated white solid was filtered and dried to yield the polymorph II, which is having DSC endotherm at 180° C.

$^1$H NMR (CDCl$_3$): δ8.70 (bs, 1H, D$_2$O exchangeable), 8.31 (d, J=7.89 Hz, 1H), 7.88–7.68 (m, 2H), 7.60–7.45 (m, 1H), 7.19 (d, J=8.46 Hz, 2H), 7.02 (d, J=8.46 Hz, 2H), 5.18 (s, 2H), 4.50 (dd, J=9.22, 3.90 Hz, 1H), 3.75 (s, 3H), 3.45 (dd, J=14.11, 3.90 Hz, 1H), 3.13 (dd, J 14.11, 9.22Hz, 1H).

EXAMPLE 23

5-[4-[[3-Ethyl-4Oxo-3,4-dihydro-2-quinazolinyl]methoxy]phenyl Methyl]thiazolidine-2,4-dione

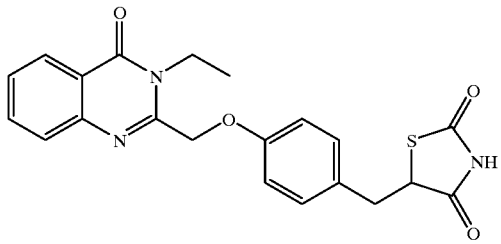

Method A

The title compound (1.186 g, 58%) was obtained from 5-[4-[[3-ethyl-4-oxo-3,4-dihydro-2-quinazolinyl]methoxy]phenyl Methylene]thiazolidine-2,4-dione (2.035 g, 5.0 mmol) (obtained from example 13) by a similar procedure to that described in example 17.

Method B

The title compound (278 mg, 68%) was obtained from 4-[[2,4-2,4-dioxo-1,3-thiazolidine-5-yl]methyl]phenoxy]acetic acid (281 mg, 1.0 mmol) (obtained from preparation 38) and 2-amino-N-methyl benzamide (164 mg, 1.0 mmol) by a similar procedure to that described in example 22 in method B. mp=218° C.

$^1$H NMR (CDCl$_3$): δ9.20 (bs, 1H, D$_2$O exchangeable) 8.30 (d, J=7.84 Hz, 1H), 7.84–7.64 (m, 2H), 7.60–7.48 (m, 1H), 7.19 (d, J=8.46 Hz, 2H), 7.02 (d, J=8.46 Hz, 2H), 5.25 (s, 2H)., 4.51 (dd, J=9.30, 3.95 Hz, 1H), 3.94 (q, J=6.92 Hz, 2H), 3.42 (dd, J=14.12, 3.95 Hz, 1H), 3.11 (dd, J=14.2, 9.30 Hz, 1H), 1.35 (t, J=6.92 Hz, 3H).

EXAMPLE 24

5-[4-[2-[2-Ethyl-4-oxo-3,4-dihydro-3-quinazolinyl]ethoxy]phenyl Methyl]thiazolidine-2,4-dione

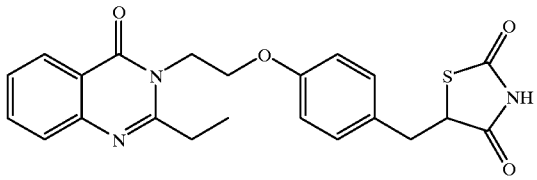

The title compound (173 mg, 82%) was obtained from 5-[4-[2-[2-ethyl-4-oxo-3,4-dihydro-3-quinazolinyl]ethoxy]phenyl methyl]-2-iminothiazolidine-4-one (211 mg, 0.5 mmol) (obtained from preparation 27) by a similar procedure to that described in example 19 (Method B), mp 178–180° C.

$^1$H NMR (CDCl$_3$): δ8.24 (d, J=7.88 Hz, 1H), 7.80–7.60 (m, 2H), 7.43 (t, J=7.56 Hz, 1H), 7.10 (d, J=8.63 Hz, 2H), 6.80 (d, J=8.63 Hz, 2H), 4.54 (t, J=5.03 Hz, 2H), 4.46 (dd, J=9.22, 3.83 Hz, 1H), 4.32 (t, J=5.03 Hz, 2H), 3.40 (dd, J=14.35, 3.83 Hz, 1H), 3.20–2.90 (m, 3H), 1.43 (t, J=7.48 Hz, 3H).

EXAMPLE 25

2-[4-[2-[2-Ethyl-4-methyl-6-oxo-1,6-dihydro-1-pyrimidinyl]ethoxy]phenyl Methyl]-1,2,4-oxadiazolidine-3,5-dione

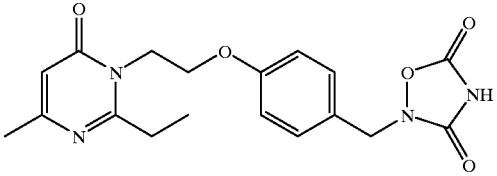

Method A

To a stirred solution of N-[4-[2-[2-ethyl-4-methyl-6-oxo-1,6-dihydro-1-pyrimidinyl]ethoxy]benzyl]-N-hydroxyurea (346 mg, 1.0 mmol) (obtained from preparation 19) in water (2 ml) was added 1N NaOH (3 ml) followed by ethyl chloroformate (191 µl, 217 mg, 2.0 mmol) and stirred for 1 h at 30° C. The reaction mixture was diluted with water, acidified to pH 3.0 and extracted with EtOAc (3×10 ml). The combined organic layers were washed with brine, dried over anhydrous Na$_2$SO$_4$ and concentrated to yield the title compound (283 mg, 76%).

Method B

To a cold (−5° C.) solution of 4-[2-[2-ethyl-4-methyl-6-oxo-1,4-dihydro-1-pyrimidinyl]ethoxy]benzyl hydroxylamine (304 mg, 1.0 mmol) (obtained from preparation 18) in anhydrous THF (4.0 ml) was added N-(chlorocarbonyl) isocyanate (88 µl, 116 mg, 1.1 mmol) dropwise. The mixture was stirred for 30 min. and poured into 2N HCl followed by extraction with EtOAc (3×10 ml). The combined organic extracts were washed with brine, dried over anhydrous Na$_2$SO$_4$ and concentrated to yield the title compound (264 mg, 71%). $^1$H NMR (CDCl$_3$+DMSO-d$_6$): δ12.40 (bs, 1H, D$_2$O exchangeable), 7.25 (d, J=8.72 Hz, 2H), 6.90 (d, J=8.72 Hz, 2H), 6.15 (s, 1H), 4.70 (s, 2H), 4.40–4.25 (m, 2H), 4.25–4.12 (m,2H), 2.91 (q, J=7.56 Hz, 2H), 2.12 (s, 3H), 1.20 (t, J=7.56 Hz, 3H).

EXAMPLE 26

5-[4-[2-2-Ethyl-4-methyl-6-oxo-1,6-dihydro-1-pyrimidinyl]ethoxy]phenyl Methylene]oxazolidine-2,4-dione

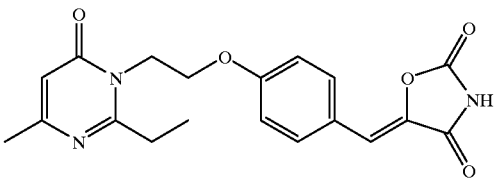

To a stirred solution of 5-[4-[2-[2-ethyl-4-methyl-6-oxo-1,6-dihydro-1-pyrimidinyl]ethoxy]phenyl methylene]-2-thio-1,3-oxazolidine-one (100 mg, 0.259 mmol) (obtained from preparation 30) in dry DMF (2 ml) was added 3-chloroperbenzoic acid (179 mg, 0.68 mmol 65%) at 0° C. and stirred for 30 min at 0° C. to 10° C. and then at 30° C. for 5 h. The reaction mixture was diluted with ethyl acetate (10 ml), washed with water (5 ml) and then with brine (5 ml); dried over anhydrous Na$_2$SO$_4$ and concentrated. The crude product was purified by flash chromatography to yield the title compound (72 mg, 75%).

$^1$H NMR (CDCl$_3$+DMSO-d$_6$): δ7.68 (d, J=8.72 Hz, 2H), 6.91 (d, J=8.72 Hz, 2H), 6.61 (s, 1H), 6.16 (s, 1H), 4.50–4.38 (m, 2H), 4.38–4.00 (m, 2H), 3.12 (q, J=7.47 Hz, 2H), 2.24 (s, 3H), 1.35 (t, J=7.47 Hz, 3H).

EXAMPLE 27

5-[4-[2-[2-Ethyl-4-methyl-6-oxo-1,6-dihydro-1-pyrimidinyl]ethoxy]phenyl Methyl]oxazolidine-2,4-dione

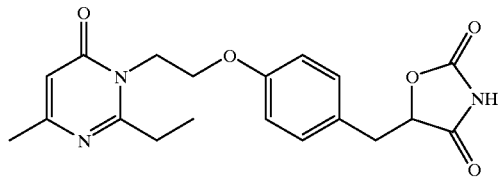

Method A

A solution of 5-[4-[2-[2-ethyl-4-methyl-6-oxo-1,6-dihydro-1-pyrimidinyl]ethoxy]phenyl methylene]oxazolidine-2,4-dione (100 mg) (obtained from example 26) in 1,4-dioxane (10 ml) was reduced with hydrogen in the presence of 10% palladium on charcoal (20 mg) at 50 psi for 24 h. The mixture was filtered through a bed of celite. The filtrate was evaporated to dryness under reduced pressure, purified by column chromatography (2:1 EtOAc/petroleum ether as eluent) to afford the title compound (90 mg, 90%).

Method B

A solution of ethyl 3-[4-[2-[2-ethyl-4-methyl-6-oxo-1,6-dihydro-1-pyrimidinyl]ethoxy]phenyl]-2-hydroxy propanoate (93 mg, 0.25 mmol) (obtained from preparation 29), urea (30 mg, 0.5 mmol) and sodium methoxide (22 mg, 0.4 mmol) in a mixture of methanol (0.5 ml) and ethanol (2.0 ml) was stirred for 2 h at 30° C., followed by reflux for 2 h. The reaction mixture was cooled to room temperature and acidified with 2N HCl to pH 4 and extracted with ethyl acetate (2×10 ml). The combined organic extracts were washed with water (5 mL), brine (5 mL), dried over anhydrous Na$_2$SO$_4$ and concentrated to yield the title compound (35 mg, 38%).

$^1$H NMR (CDCl$_3$+DMSO-d$_6$): δ7.14 (d, J=8.51 Hz, 2H), 6.77 (d, J=8.5 Hz, 2H), 6.17 (s, 1H), 4.95 (t, J=4.82 Hz, 1H), 4.42 (t, J=4.94 Hz, 2H), 4.24 (t, J=4.94 Hz, 2H), 3.38–3.00 (m, 2H), 3.00 (q, J=7.42 Hz, 2H), 2.25 (s, 3H), 1.34 (t, J=7.42 Hz, 3H).

EXAMPLE 28

5-[4-[[3-Methyl-4-oxo-3,4-dihydro-2-quinazolinyl]methoxy]phenyl Methyl]thiazolidine-2,4-dione Sodium Salt

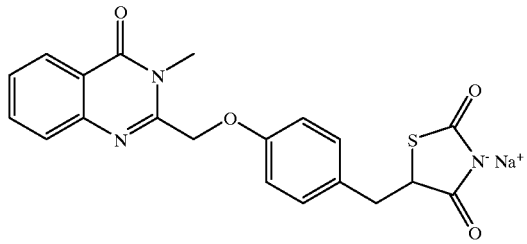

To a stirred suspension of 5-[4-[[3-methyl-4-oxo-3,4-dihydro-2-quinazolinyl]methoxy]phenyl methyl]thiazolidine-2,4-dione (21.0 g, 53.2 mmol) (obtained from example 22) in methanol (200 ml) was added a solution of sodium methoxide (11.45 g, 212 mmol) in methanol (25 ml) dropwise at 30° C. During this period the suspension slowly dissolved completely and a white solid precipitated out which was stirred further for 1 h. The solid was filtered and washed with methanol (20 ml) and dried to afford the title compound (20.6 g, 93%), mp 235° C.

$^1$H NMR (DMSO-d$_6$): δ8.16 (d, J=7.47 Hz, 1H), 7.84 (t, J=7.47 Hz, 11H), 7.69 (d, J=7.47 Hz, 1H), 7.56 (t, J=7.47 Hz, 1H), 7.15 (d, J=8.72 Hz, 2H), 7.00 (d, J=8.72 Hz, 2H), 5.25 (s, 2H), 4.09 (dd, J=10.34, 3.36 Hz, 1H), 3.61 (s, 3H), 3.30 (dd, J=13.82, 3.36 Hz, 1H), 2.62 (dd, J=13.82, 10.34 Hz, 1H).

Polymorphs

The reactions were carried out in variety of solvents, using different equivalents of base and different amounts of solvents.

Different polymorphs were observed depending on conditions used, which has shown in the following table:

| | | CONDITIONS | | | |
|---|---|---|---|---|---|
| S. No. | Polymorphs | Free Acid | Solvent/mL | eq. of NaOMe | DSC endotherm |
| 1. | Form I | 1 g | Isopropanol-10 mL | 1.5 eq | 280° C. |
| 2. | Form II | 1 g | Methanol-15 mL | 2.0 eq | 276° C. |
| 3. | Form III | 1 g | Methanol-10 mL | 2.0 eq | 272° C. |
| 4. | Form IV | 1 g | Ether-5 mL | 1.5 eq | 263° C. |
| 5. | Form V | 1 g | Ethanol-10 mL | 1.1 eq | 185° C. |

EXAMPLE 29

5-[4-[2-[2,5,6-Trimethyl-4-oxo-3,4-dihydro-thieno-[2,3-d]-pyrimidin-3-yl]ethoxy]phenyl Methylene]thiazolidine-2,4,-dione

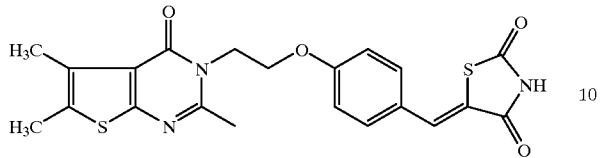

The title compound (550 mg, 85%) was obtained from 4-[2-[2,5,6-trimethyl-4-oxo-thieno-3-pyrimidinyl]ethoxy] benzaldehyde (500 mg, 1.46 mmol) (obtained from preparation 31) and thiazolidine-2,4-dione (257 mg, 2.2 mmol) by a similar procedure to that described in example 1, mp 280° C.

$^1$H NMR (DMSO-$d_6$): δ12.52 (bs, 1H, $D_2O$ exchangeable), 7.71 (s, 1H), 7.52 (d, J=8.39 Hz, 2H), 7.10 (d, J=8.39 Hz, 2H), 4.50–4.20 (m, 4H), 2.66 (s, 3H), 2.36 (s, 3H), 2.32 (s, 3H).

EXAMPLE 30

5-[4-[2-[2-Methyl-4-oxo-3,4-dihydro-3-quinazolinyl]ethoxy]phenyl Methylene]thiazolidine-2,4-dione, Sodium Salt

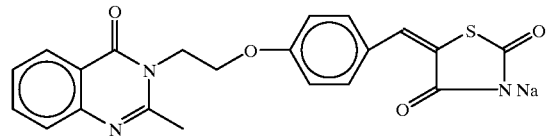

The title compound (385 mg, 90%) was obtained from 5-[4-[2-[2-methyl-4-oxo-3,4-dihydro-3-quinazolinyl]ethoxy]phenyl methylene]thiazolidine-2,4-dione (obtained from example 9) (407 mg, 1.0 mmol) by a similar procedure to that described in example 28. mp 280° C. (decomposes)

$^1$H NMR (DMSO-$d_6$+CDCl$_3$): δ8.12 (d, J=8.0 Hz, 1H), 7.78 (t, J=8.0 Hz, 1H), 7.58 (d, J=8.0 Hz, 1H), 7.46 (t, J 8.0 Hz, 1), 7.45 (d, J=8.7 Hz, 2), 7.25 (s, 1), 6.98 (d, =8.7 Hz, 2H), 4.55–4.40 (m, 2H), 4.40–4.25 (m, 2H), 2.75 (s, 3H).

EXAMPLE 31

5-[4-[2-[2-Ethyl-4-oxo-3,4-dihydro-3-quinazolinyl]ethoxy]phenyl methylene] Thiazolidine-2,4-dione, Sodium Salt

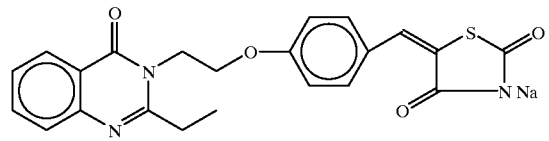

The title compound (405 mg, 91%) was obtained from S-[4-[2-[2-ethyl-4-oxo-3,4-dihydro-3-quinazolinyl]ethoxy] phenyl methylene]thiazolidine-2,4-dione (obtained from example 10) (421 mg, 1.0 mmol), by a similar procedure to that described in example 28. mp: 250° C. (decomposes).

$^1$H NMR (DMSO-$d_6$+CDCl$_3$): δ8.15 (d, J=8.0 Hz, 1H), 7.79 (t, J=8.0 Hz, 1H), 7.65 (s, 1H), 7.60–7.45 (m, 4H), 7.10 (d, J=8.7 Hz, 2H), 4.60–4.45 (m, 2H), 4.45–4.32 (m, 2H), 3.10 (q, J=7.5 Hz, 2H), 1.35 (t, J=7.5 Hz, 3H).

EXAMPLE 32

5-[4-[2-[4-Methyl-2-propyl-6-oxo-1,6-dihydro-1-pyrimidinyl]ethoxy]phenyl Methyl]thiazolidine-2,4-dione, Sodium Salt

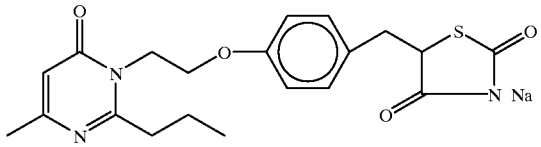

The title compound (460 mg, 88.5%) was obtained from 5-[4-[2-[2-ethyl-2-propyl-6-oxo-1,6 dihydro-1-pyrimidinyl] ethoxy]phenyl methyl]thiazolidine-2,4-dione (obtained from example 17) (560 mg, 1.21 mmol) by a similar procedure to that described in example 28, mp : 230° C.

$^1$H NMR (DMSO-$d_6$): δ7.09 (d, J=8.53 Hz, 2H), 6.78 (d, J=8.53 Hz, 2H), 6.15 (s, 1H), 4.38–4.25 (m, 2H), 4.25–4.10 (m, 2H), 4.06 (dd, J=10.47, 3.42 Hz, 1H), 3.28 (dd, J=13.69, 10.47 Hz, 1H), 2.85 (t, J=7.4 Hz, 2H), 2.62 (dd, J=13.69, 3.42 Hz, 1H), 2.15 (s, 3H), 1.71 (q, J=7.47 Hz, 2H), 0.96 (t, J=7.47 Hz, 3H).

EXAMPLE 33

5-[4-[2-[2-Ethyl-4-methyl-6-oxo-1,6-dihydro-1-pyrimidinyl]ethoxy]phenyl Methyl]thiazolidine-2,4-dione, Sodium Salt

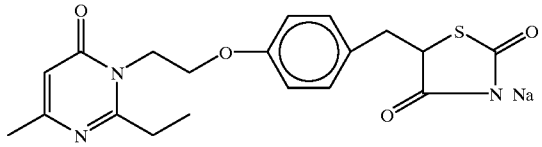

The title compound (0.6 g, 94.6%) was obtained from 5-[4-[2-[2-ethyl-4-methyl-6-oxo-1,6-dihydro-1-pyrimidinyl]ethoxy]phenyl methyl]thiazolidine-2,4-dione (0.6 g, 1.55 mmol) (obtained from example 19) by a similar procedure to that described in example 28. mp : 258–260° C.

$^1$H NMR (DMSO-$d_6$): δ7.10 (d, J=7.53 Hz, 2H), 6.80 (d, J=7.53 Hz, 2H), 6.16 (s, 1H), 4.32 (t, J=5.26 Hz, 2H), 4.16 (t, J=5.26 Hz, 2H), 4.10 (dd, J=9.6, 3,4 Hz, 1H), 3.4–3.25 (dd, J=13.6, 9.62 Hz, 1H), 2.91 (q, J=7.3 Hz, 2H), 2.59 (dd, J=13.6, 3,4 Hz, 1H), 2.66 (s, 3H), 1.25 (t, J=7.3 Hz, 3H).

EXAMPLE 34

5-[4-[2-[2-Ethyl-4-trifluoromethyl-6-oxo-1,6-dihydro-1-pyrimidinyl]ethoxy]phenyl Methyl]thiazolidine-2,4-dione

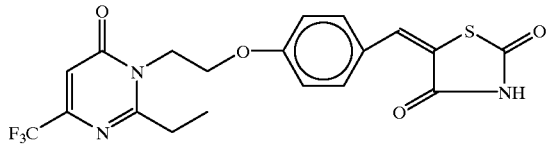

The title compound (550 mg) was obtained from [4-[2-[2-ethyl-4-trifluoromethyl-6-oxo-1,6-dihydro-1-pyrimidinyl]ethoxy]benzaldehyde (700 mg, 2.05 mmol) (obtained from preparation 36) and thiazolidine-2,4-dione (240 mg, 2.05 mmol) by a similar procedure to that described in example 1. mp: >250° C.

$^1$H NMR (CDCl$_3$+DMSO-d$_6$): δ 7.70 (s, 1H), 7.45 (d, J=8.3 Hz, 2H), 6.95 (d, J=8.3 Hz, 2H), 6.69 (s, 1H), 4.50 (t, J=4.5 Hz, 2H), 4.35 (t, J=4.5 Hz, 2H), 3.11 (q, J=7.2 Hz, 2H), 1.38 (t, J=7.2 Hz, 3H).

EXAMPLE 35

5-[4-[2-[2-Ethyl-4-trifluoromethyl-6-oxo-1,6-dihydro-1-pyrimidinyl]ethoxy]phenyl Methyl]thiazolidine-2,4-dione

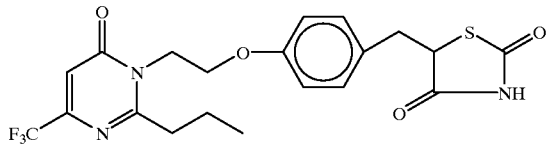

The title compound (0.3 g, 66%) was obtained from 5-[4-[2-[2-ethyl-4-trifluoromethyl-6-oxo-1,6-dihydro-1-pyrimidinyl]ethoxy]phenyl methyl]thiazolidine-2,4-dione (0.45 g, 1.025 mmol) obtained from example 34 by a similar procedure to that described in example 17. p: 135° C.

$^1$H NMR (DMSO-d$_6$): δ7.11 (d, J 8.53 Hz, 2H), 6.77 (d, J=8.53 Hz, 2H), 6.70 (s, 1H), 4.52–4.38 (m, 1H), 4.46 (t, =4.68 Hz, 2H), 4.28 (t, =4.68 Hz, 2H), 3,4 (dd, J=14.21, 3.83 Hz, 1H), 3.20–2.98 (m, 3H), 1.38 (t, J=7.33 Hz, 3H).

EXAMPLE 36

5-[4-[2-[2-Methyl-4-oxo-3,4-dihydro-3-quinazolinyl]ethoxy]phenyl Methyl]thiazolidine-2,4-dione

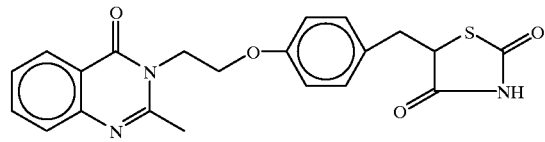

The title compound (1.6 g, 89%) was obtained from 5-[4-[2-[2-methyl-4-oxo-3,4-dihydro-3-quinazolinyl]ethoxy]phenyl methyl]-2-iminothiazolidine-4-one (1.8g, 4.4 mmol) (obtained from preparation 35) by a similar procedure to that described in example 19 (method B), 242–2444° C.

$^1$H NMR (DMSO-d$_6$): δ11.98 (bs, 1H, D$_2$O exchangeable), 8.11 (d, J=7.50 Hz, 1H), 7.80 (t, J=7.50 Hz, 1H), 7.59 (d, J=7.50 Hz, 1H), 7.48 (t, J=7.50 Hz, 1H), 7.14 (d, J=8.35 Hz, 2H), 6.89 (d, J=8.35 Hz, 2H), 4.85 (dd, J=9.03, 4.20 Hz, 1H), 4.45 (t, J=5.14 Hz, 2H), 4.27 (t, J=5.14 Hz, 2H), 3.28 (dd, J=14.12, 4.20 Hz, 1H), 3.04 (dd, J=14.12, 9.03 Hz, 1H), 2.71 (s, 3H).

EXAMPLE 37

5-[4-[2-[2-Methyl-4-oxo-3,4-dihydro-3-quinazolinyl]ethoxy]phenyl Methyl]thiazolidine-2,4-dione, Sodium Salt

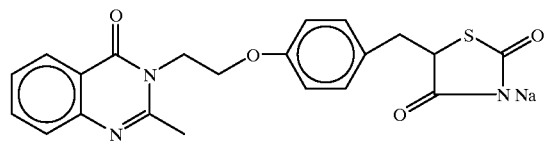

The title compound (348 mg, 81%) was obtained from 5-[4-[2-[2-methyl-4-oxo-3,4-dihydro-3-quinazolinyl]ethoxy]phenyl methyl]thiazolidine2,4-dione (409 mg, 1 mmol) (obtained from example 36) by a similar procedure to that described in example 28. mp: 317° C.

$^1$H NMR (DMSO-d$_6$) δ 8.11 (d, J=7.88 Hz, 1H), 7.79 (t, J=7.05 Hz, 1H), 7.59 (d, J=7.88 Hz, 1H), 7.48 (t, J=7.05 Hz, 1H), 7.08 (d, J=8.40 Hz, 2H), 6.83 (d, J=8.40 Hz, 2H), 4.44 (t, J=5.40 Hz, 2H), 4.26 (t, J=5.40 Hz, 2H), 4.06 (dd, J=10.43, 3.42 Hz, 1H), 3.28 (dd, J=13.8, 3.42 Hz, 1H), 2.62 (dd, J=13.8, 10.43 Hz, 1H), 2.71 (s, 3H).

EXAMPLE 38

5-[4-[2-[2-Ethyl-4-oxo-3,4-dihydro-3-quinazolinyl]ethoxy]phenyl Methyl]thiazolidine-2,4-dione, Sodium Salt

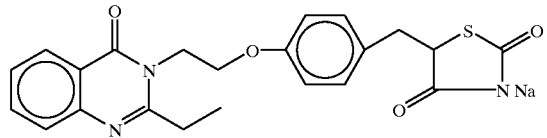

The title compound (700 mg, 68%) was obtained from 5-[4-[2-[2-methyl-4-oxo-3,4-dihydro-3-quinazolinyl]ethoxy]phenyl methyl]thiazolidine-2,4-dione (978 mg, 2.3 mmol) (obtained from example 24) by a similar procedure to that described in example 28. mp: 280° C.

¹H NMR (DMSO-d₆) δ: 8.15 (d, J=7.89 Hz, 1H), 7.82 (t, J=7.89 Hz, 1H), 7.65 (d, J=7.89 Hz, 1H), 7.51 (t, J=7.89 Hz, 1H), 7.11 (d, J=8.40 Hz, 2H), 6.83 (d, J=8.40 Hz, 2H), 4.48 (t, J=5.4 Hz, 2H), 4.27 (t, J=5.40 Hz, 2H), 4.08 (dd, J=10.39, 3.12 Hz, 1H), 3.25 (dd, J=10.39, 3.12 Hz, 1H), 3.06 (q, J=7.15 Hz, 2H), 2.64 (dd, J=13.82, 10.39 Hz, 1H), 1.34 (t, J=7.15 Hz, 3H).

EXAMPLE 39

5-[4-[[6,7-Dimethoxy-3-methyl-4-oxo-3,4-dihydro-2-quinazolinyl]methoxy]phenyl Methyl]thiazolidine-2,4-dione

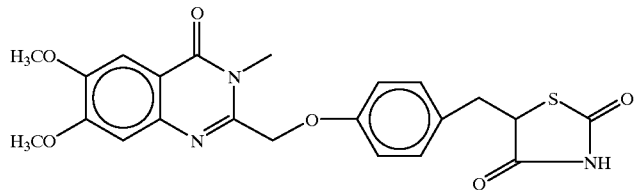

The title compound (1.0 g, 44%) was obtained from 4-[[2,4-dioxo-1,3-thiazolidine-5-yl]methyl]phenoxy]acetic acid (1.05 g, 5.0 mmol) 2-amino-N-methyl benzamide (1.5 g, 5.34 mmol) by a similar procedure to that described in example 22, method B; mp: 252° C.

¹H NMR (CDCl₃): δ7.61 (s, 1H), 7.46 (s, 1H), 7.14 (d, J=8.72 Hz, 2H), 6.98 (d, J=8.72 Hz, 2H), 5.15 (s, 2H), 4.5 (dd, J=10.20, 3.30 Hz, 1H), 4.0 (s, 6H), 3.74 (s, 3H), 3.45 (dd, J=14.3, 3.30 Hz, 1H), 3.16 (dd, J=14.3, 10.20 Hz, 1H).

EXAMPLE 40

5-[4-[[6,7-Dimethoxy-3-methyl-4-oxo-3,4-dihydro-2quinazolinyl]methoxy]phenyl Methyl]thiazolidine-2,4-dione, Sodium Salt

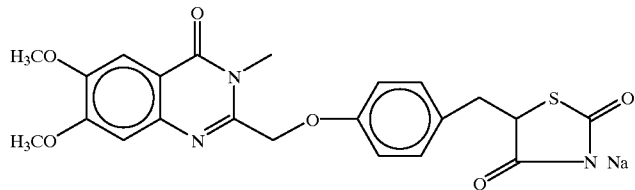

The title compound (140 mg, 64%) was obtained from 5-[4-[[(6,7-dimethoxy-3-methyl-4-oxo-3,4-dihydro-2-quinazolinyl]methoxy]phenyl methyl]thiazolidine-2,4-dione (210 mg, 0.46 mmol) (obtained from example 39) by a similar procedure to that described in example 28. mp : 275° C.

¹H NMR (DMSO-d₆): δ7.46 (s, 1H), 7.16 (s, 1H), 7.14 (d, J=7.50 Hz, 2H), 6.98 (d, J=7.50 Hz, 2H), 5.19 (s, 2H), 4.20 (dd, J=10.50, 3.50 Hz, 1H), 3.90 (5, 3H), 3.88 (5, 3H), 3.60 (s, 3H), 3.32 (dd, J=13.70 Hz, 3.50 Hz, 1H), 2.67 (dd, J=13.7, 10.0 Hz, 1H).

EXAMPLE 41

5-[4-[[3-Methyl-4-oxo-3,4-dihydro-2-quinazolinyl]methoxy]phenyl Methyl]thiazolidine-2,4-dione, Potassium Salt

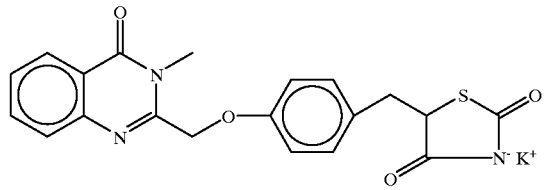

To a stirred solution of 5-[4-[[3-methyl-4-oxo-3,4-dihydro-2-quinazolinyl]methoxy]phenyl methyl]

thiazolidine-2,4-dione (10.0 g, 25.3 mmol) (obtained from example 22) in methanol (100 mL) was added a solution of tBuOK (3.40 g, 30.3 mmol) in methanol (50 mL) dropwise at 30° C. During this period the suspension slowly dissolved completely and a white solid precipitated out which was stirred further for 1 h. The solid was filtered and washed with methanol (20 mL) and dried to afford the title compound (9.8 g, 90%). mp: 302° C.

$^1$H N (DMSO-d$_6$): δ8.17 (d, J=7.89 Hz, 1H), 7.85 (t, J=7.52 Hz, 1H), 7.7 (d, J=7.89 Hz, 1H), 7.58 (t, J=7.52 Hz, 1H), 7.16 (d, J=8.63 Hz, 2H),7.01 (d, J=8.63 Hz, 2H), 5.25 (s, 2H), 4.12 (dd, J=10.47, 3.56 Hz, 1H), 3.62 (s, 3H), 3.32 (dd, J=13.70, 3.56 Hz, 1H), 2.65 (dd, J=13.70, 10.47 Hz, 1H).

EXAMPLE 42

5-[4-[[3-Methyl-4-oxo-3,4-dihydro-2-quinazolinyl] methoxy]phenyl methyl]thiazolidine-2,4-dione, Calcium Salt

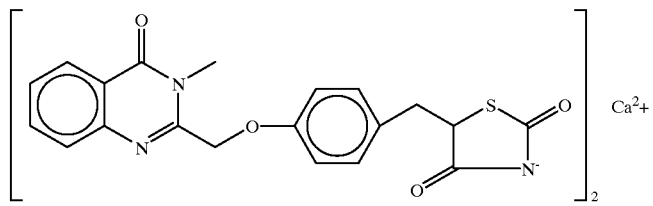

A mixture of 5-[4-[[3-[methyl-4-oxo-3,4-dihydro-2-quinazolinyl]methoxy]phenyl]methyl]thiazolidine-2,4-dione (1.0 g, 2.53 mmol) (obtained from example 22) and Ca(OH)$_2$ (94 mg, 1.27 mmol) in methanol (40 mL) was immersed in preheated oil bath at 100° C. and refluxed for 4h. The reaction mixture was cooled to room temperature and methanol was completely removed under reduced pressure at 40–50° C. The resultant foamy solid was triturated with ether. The white crystalline compound obtained was filtered and washed with ether (5–10 mL) and dried to afford the title compound (1.025 g, 94%) mp : 225° C.

$^1$H NMR (DMSO-d$_6$): δ 8.15 (d, J=7.89 Hz, 1H), 7.83 (t, J=7.89 Hz, 1H), 7.68 (d, J=7.89 Hz, 1H), 7.56 (t, J=7.89 Hz, 1H), 7.16 (d, J=8.35 Hz, 2H), 7.01 (d, J=8.35 Hz, 2H), 5.24 (s, 2H), 4.23 (dd, J=10.38, 3.23 Hz, 1H), 3.61 (s, 3H), 3.33 (dd, J=13.70, 3.23 Hz, 1H), 2.70 (dd, J=13.7, 10.38 Hz, 1H).

EXAMPLE 43

5-[4-[[3-Methyl-4-oxo-3,4-dihydro-2-quinazolinyl] methoxy]phenyl methylene]thiazolidine-2,4-dione, Sodium Salt

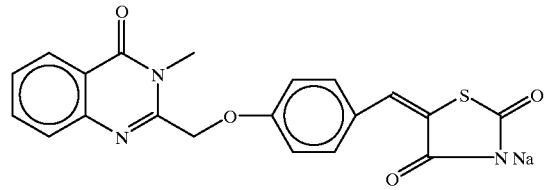

The title compound (1.89 g, 90%) was obtained from 5-[4-[[3-methyl-4-oxo-3,4-dihydro-2-quinazolinyl] methoxy]phenyl methylene]thiazolidine-2,4-dione (2.0 g, 5.09 mmol) (obtained from example 12) by a similar procedure to that described in example 28. mp : 299° C.

$^1$H NMR (DMSO-d$_6$) δ: 8.18 (d, J=7.89 Hz, 1H), 7.86 (t, J=7.89 Hz, 1H), 7.69 (d, J=7.89 Hz, 1H), 7.59 (t, J=7.89 Hz, 1H), 7.52 (d, J=8.72 Hz, 2H), 7.28 (s, 1H), 7.21 (d, J=8.72 Hz, 2H), 5.35 (s, 2H), 3.64 (s, 3H).

Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa and zucker rats have been developed by the various laboratories for understanding the pathophysiology of disease and testing the efficacy of new antidiabetic compounds (Diabetes, (1983) 32: 830–838; Annu. Rep. Sankyo Res. Lab. (1994) 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled The state of pancreas and its course vary according to the models. Since this model resembles that of type II diabetes mellitus, the compounds of the present invention were tested for blood sugar and triglycerides lowering activities.

The compounds of the present invention showed blood sugar and triglycerides lowering activites through improved insulin resistance. This was demonstrated by the following in vivo experiments.

Male C57BL/KsJ-db/db mice of 8 to 14 weeks age, having body weight range of 35 to 60 grams, procured from the Jackson Laboaotory, USA, were used in the experiment. The mice were provided with standard feed (National Institute of Nutrition, Hyderabad, India) and acidified water, ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in tubes containing EDTA which was centrifuged to obtain plasma. The plasma glucose and triglycerides levels were measured spectrometrically, by glucose oxidase and glycerol-3-PO$_4$ oxidase/peroxidase enzyme (Dr. Reddy's Lab. Diagnostic Division Kits, Hyderabad, India) methods respectively. On 6th day the blood samples were collected one hour after administration of test compounds/vehicle for assessing the biological activity.

Test compounds were suspended on 0.25% carboxymethyl cellulose and administered to test group at a dose of 10 mg to 100 mg/kg through oral gavage daily for 6 days. The control group received vehicle (dose 10 ml/kg). Troglitazone (100 mg/kg, daily dose) was used as a standard drug which showed 28% reduction in random blood sugar level on 6th day.

The blood sugar and triglycerides lowering activities of the test compound was calculated according to the formula:

$$\text{Blood sugar/triglycerides lowering activity (\%)} = 1 - \frac{DT/DC}{TC/ZC} \times 100$$

ZC=Zero day control group value
DC=Zero day treated group value
TC=Control group value on test day
DT=Treated group value on the test day No adverse effects were observed for any of the mentioned compounds of invention in the above test.

The compounds of the present invention also showed cholesterol lowering activity in the experimental animals used.

| Compound | Dose mg/kg/da | Days treated | Maximum reduction in blood glucose level (%) | Triglyceride lowering (%) |
|---|---|---|---|---|
| Example 3 | 100 | 6 | 67 | 12 |
| Example 6 | 100 | 6 | 41 | 31 |
| Example 7 | 100 | 6 | 66 | 35 |
| Example 9 | 30 | 6 | 46 | 35 |
| Example 12 | 100 | 6 | 71 | 57 |
| Example 13 | 100 | 6 | 52 | 57 |
| Example 17 | 30 | 6 | 65 | 45 |
| Example 19 | 30 | 6 | 73 | 70 |
| Example 21 | 30 | 6 | 64 | 76 |
| Example 22 | 30 | 6 | 55 | 41 |
| Example 24 | 10 | 6 | 63 | 17 |
| Example 11 | 30 | 6 | 32 | 42 |
| Example 28 | 10 | 6 | 63 | 57 |

The experimental results from the db/db mice suggest that the novel compounds of the present invention also possess therapeutic utility as a prophylactic or regular treatment for obesity, cardiovascular disorders such as hypertension, hyperlipidaemia and other diseases; as it is known from the literature that such diseases are interrelated to each other.

What is claimed is:

1. A process for the preparation of compound of formula (I)

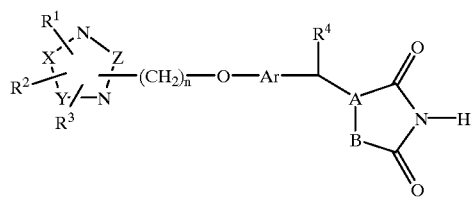

(I)

where one of X, Y and Z represents C=O or C=S and one of the remaining of X, Y and Z represents a group C= and the other of the remaining X, Y and Z represents C=C; $R^1$, $R^2$ and $R^3$ are substituents either on X, Y or Z or on a nitrogen atom and may be the same or different and represent hydrogen, halogen, hydroxy or nitro, or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, thioalkyl, alkylthio or carboxylic acid or its derivatives or sulfonic acid or its derivatives with the provision that when $R^1$, $R^2$ or $R^3$ is on a nitrogen atom it does not represent hydrogen, halogen, nitro, carboxylic or sulfonic acid groups; or any two of $R^1$, $R^2$ and $R^3$ along with the adjacent atoms to which they are attached may also form a substituted or unsubstituted cyclic structure of 4 to 7 atoms with one or more double bonds, the cyclic structure may be carbocyclic or may contain one or more heteroatoms selected from oxygen, nitrogen and sulfur; the linking group represented by —$(CH_2)_n$—O— may be attached either through nitrogen or through X, Y or Z and n is an integer ranging from 1–4: Ar represents an optionally substituted divalent aromatic or heterocyclic group; $R^4$ represents hydrogen, halogen or lower alkyl group or forms a bond together with the adjacent group A; A represents a nitrogen atom or a group $CR^5$ where $R^5$ represents hydrogen, halogen or lower alkyl group or $R^5$ forms a bond together with $R^4$; B represents an oxygen or a sulfur atom when A is $CR^5$ and B represents an oxygen atom when A is a nitrogen atom, comprising:

a) reacting a compound of formula (XVII)

(XVII)

where $R^1$, $R^2$ and $R^3$ are as defined earlier, X represent, C=O or C=S and Y represents C=C; or $R^2$ and $R^3$ together with Y form a cyclic structure as defined earlier where X represents C=O or C=S, Y represents C=C and $R^1$ is as defined earlier, with a compound of formula (XVIII)

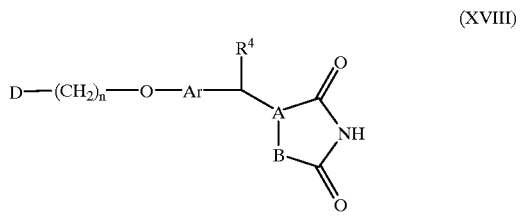

(XVIII)

where Ar, $R^4$, A, B and n are as defined earlier, D is —CN or —$C(OR^7)_3$ where $R^7$ is $(C_1–C_4)$alkyl, or —$C(=O)$—$R^8$ where $R^8$ is selected from —OH, Cl, Br, I, —$NH_2$, —NHR, and OR where R is a lower alkyl group; or $R^8$ is O—(C=O)—$R_9$, where $R^9$ is a linear or branched $(C_1–C_5)$ alkyl group and (b) converting a compound of formula (I) into its pharmaceutically acceptable salts, polymorphs, or solvates.

2. A process according to claim 1 where the compound of formula (I) is formed through the intermediate formation of compound of formula (XIX),

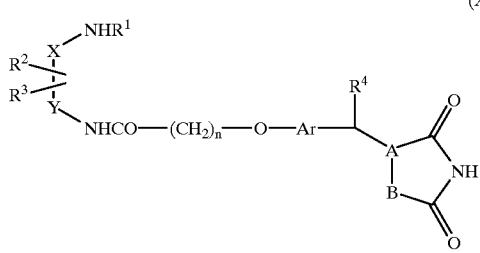

where $R^1$, $R^2$, $R^3$, n, Ar, $R^4$, A and B are as defined in claim 1 and X represents C=O or C=S and Y represents C=C or Y together with $R^2$ and $R^3$ form a cyclic structure as defined in claim 1.

3. A process according to claim 2 wherein the intermediate of formula (XIX)

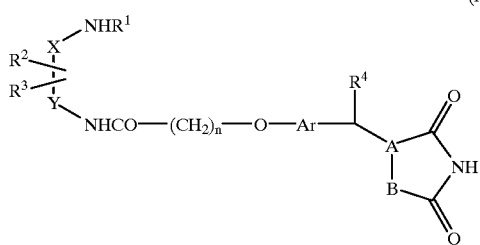

where X, Y, $R^1$, $R^2$, $R^3$, n, Ar, $R^4$, A and B are as defined in claim 2 is cyclised to form the compound of formula (I).

4. A process according to claim 1, to prepare a compound of formula (I) where X represents C=O, Y represents C=C, Z represents =C, n represents the integer 1, $R^1$ represents methyl group, B represents sulfur atom, $R^2$ and $R^3$ together with Y form a phenyl ring and is represented by formula (XX)

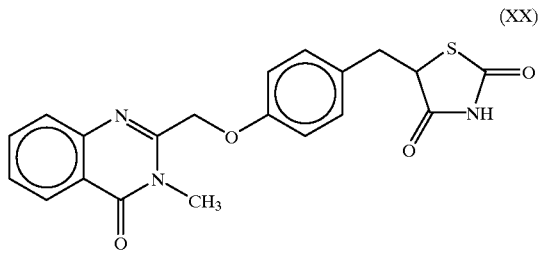

which comprises:

a) reducing a compound of formula (XXI)

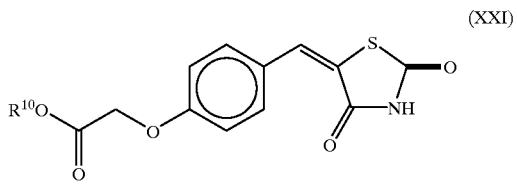

where $R^{10}$ is a lower alkyl group to yield a compound of formula (XXII)

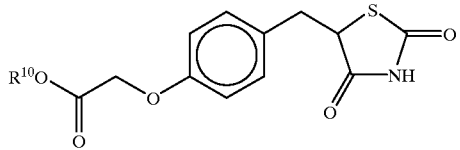

where $R^{10}$ is as defined above, b) hydrolysis of compound of formula (XXII) to yield a compound of formula (XXIII)

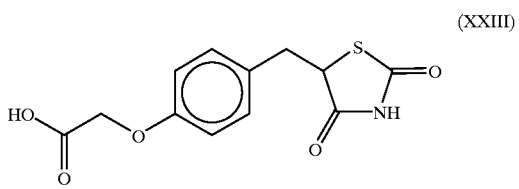

c) reacting a compound of formula (XXIII) with acid halide or halogenating agent to obtain a compound of formula (XXIV)

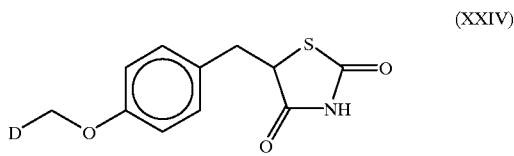

where D represents COCl, COBr or —C(=O)—O—(C=O)—$R^9$, where $R^9$ represents methyl or t-butyl group, d) reacting a compound of formula (XXIV) with a compound of formula (XXV)

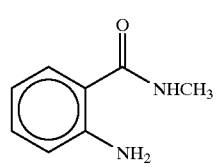

to yield a compound of formula (XX) defined above through the intermediate formation of compound of formula (XXVI) and optionally

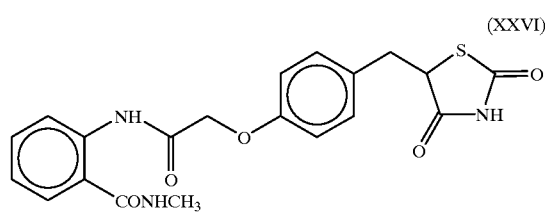

e) converting a compound of formula (XX) into its pharmaceutically acceptable salts, polymorphs, or solvates.

5. A process according to claim 4, wherein the compound of formula (XXVI)
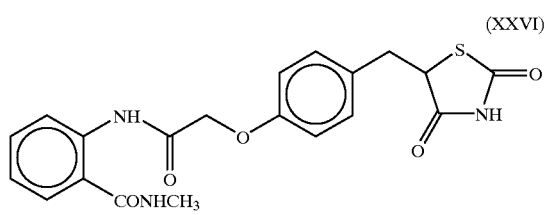
is cyclised to obtain a compound of formula (XX)
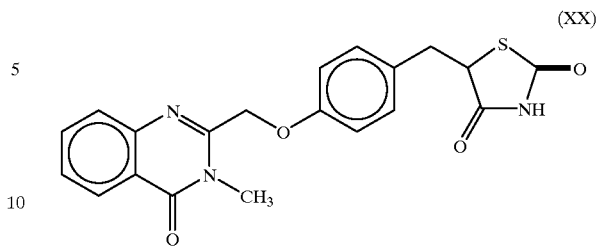
* * * * *

UNITED STATES PATENT AND TRADEMARK OFFICE

CERTIFICATE OF CORRECTION

PATENT NO. : 6,114,526

DATED : September 5, 2000

INVENTOR(S) : Vidya Bhushan LOHRAY, et al.

It is certified that error appears in the above-identified patent and that said Letters Patent are hereby corrected as shown below:

On title page, item 63, delete "Continuation of application No. 08/777,627, Dec. 31, 1996, Pat. No. 5, 885,997, and a"; "division" should read -- Division -- and after "1997" insert -- which is a continuation-in-part of application No. 08/777,627, Dec. 31, 1996, Pat. No. 5,885,997 --.

Col. 1, lines 8-9, delete "continuation of Ser. No. 08/777,627 filed Dec. 31, 1996 now U.S. Pat. No. 5,885,997, and a" and after "1997" insert -- which is a continuation-in-part of Ser. No. 08/777,627 filed Dec. 31, 1996 now U.S. Pat. No. 5,885,997. --

Signed and Sealed this

Seventeenth Day of April, 2001

Attest:

NICHOLAS P. GODICI

Attesting Officer     *Acting Director of the United States Patent and Trademark Office*